US011311228B1

(12) United States Patent
Oakley et al.

(10) Patent No.: US 11,311,228 B1
(45) Date of Patent: Apr. 26, 2022

(54) MULTI-FUNCTION APPARATUS, SYSTEMS AND METHODS FOR RECEIVING SIGNALS FROM A HUMAN SUBJECT'S HEAD

(71) Applicant: WAVi Co., Boulder, CO (US)

(72) Inventors: David Oakley, Boulder, CO (US); Edward Altshuler, Dacono, CO (US); Scott Seamans, Newport Beach, CA (US); David Joffe, Louisville, CO (US); Francis Palermo, Boulder, CO (US); Andre Joffe, Louisville, CO (US); Hunter Velds, Boulder, CO (US)

(73) Assignee: WAVI Co., Boulder, CO (US)

( * ) Notice: Subject to any disclaimer, the term of this patent is extended or adjusted under 35 U.S.C. 154(b) by 533 days.

(21) Appl. No.: 15/834,789

(22) Filed: Dec. 7, 2017

Related U.S. Application Data

(63) Continuation-in-part of application No. 15/163,292, filed on May 24, 2016, now Pat. No. 9,854,988.

(60) Provisional application No. 62/196,066, filed on Jul. 23, 2015, provisional application No. 62/170,104, filed on Jun. 2, 2015.

(51) Int. Cl.
*A61B 5/291* (2021.01)
*A61B 5/00* (2006.01)
*A61B 5/024* (2006.01)
*A61B 5/0205* (2006.01)

(52) U.S. Cl.
CPC ............ *A61B 5/291* (2021.01); *A61B 5/0006* (2013.01); *A61B 5/0205* (2013.01); *A61B 5/6803* (2013.01); *A61B 5/02416* (2013.01); *A61B 5/02438* (2013.01); *A61B 2562/0209* (2013.01); *A61B 2562/046* (2013.01); *A61B 2562/06* (2013.01)

(58) Field of Classification Search
CPC ........ A61B 2562/0209; A61B 2562/06; A61B 5/6816; A61B 5/6838; A61B 5/02416; A61B 5/0261; A61B 5/0478; A61B 5/0006; A61B 5/6803; A61B 5/0205; A61B 5/02438; A61B 2562/046
USPC ................................................. 600/323, 383
See application file for complete search history.

(56) References Cited

U.S. PATENT DOCUMENTS

| | | |
|---|---|---|
| 3,508,541 A | 4/1970 | Westbrook |
| 4,632,122 A | 12/1986 | Johansson et al. |
| 4,923,469 A | 5/1990 | Frachet |
| 5,479,934 A | 1/1996 | Imran |
| 6,161,030 A | 12/2000 | Levandowski |
| 6,167,298 A | 12/2000 | Levin |
| 6,195,576 B1 | 2/2001 | John |
| 6,381,481 B1 | 4/2002 | Levandowski et al. |

(Continued)

FOREIGN PATENT DOCUMENTS

| | | |
|---|---|---|
| JP | 2013078419 A | 5/2013 |
| WO | 0051028 A1 | 8/2000 |
| WO | 2009079377 A2 | 6/2009 |

*Primary Examiner* — Linda C Dvorak
*Assistant Examiner* — Christine A Dedoulis
(74) *Attorney, Agent, or Firm* — E. Randall Smith; E. Randall Smith, P.C.

(57) ABSTRACT

Apparatus, systems and methods for receiving signals from a human subject's head includes a headset having a plurality of electroencephalographic "(EEG)" electrodes associated therewith for facilitating receiving EEG signals from the subject's head and at least one ear clip configured to be releasably secured to the subject's ear(s).

40 Claims, 26 Drawing Sheets

(56) References Cited

U.S. PATENT DOCUMENTS

| | | | |
|---|---|---|---|
| 6,574,513 B1 | 6/2003 | Collura | |
| 6,912,414 B2 | 6/2005 | Tong | |
| 7,155,276 B2 * | 12/2006 | Lamont | A61N 1/0472 600/545 |
| 8,348,678 B2 * | 1/2013 | Hardisty | H01R 13/6205 439/39 |
| 8,924,230 B2 | 12/2014 | Oakley et al. | |
| 8,930,212 B2 | 1/2015 | Oakley et al. | |
| 8,930,218 B1 | 1/2015 | Oakley et al. | |
| 2002/0188216 A1 | 12/2002 | Kayyali et al. | |
| 2003/0233250 A1 | 12/2003 | Joffe et al. | |
| 2004/0236226 A1 | 11/2004 | Maki | |
| 2005/0107716 A1 | 5/2005 | Eaton et al. | |
| 2007/0004978 A1 | 1/2007 | Ponton | |
| 2007/0093706 A1 | 4/2007 | Gevins et al. | |
| 2007/0225585 A1 * | 9/2007 | Washbon | A61B 5/0478 600/393 |
| 2007/0260131 A1 * | 11/2007 | Chin | A61B 5/6838 600/323 |
| 2008/0027345 A1 * | 1/2008 | Kumada | A61B 5/0478 600/383 |
| 2009/0030298 A1 | 1/2009 | Matthews | |
| 2009/0088619 A1 | 4/2009 | Turner et al. | |
| 2009/0156925 A1 | 6/2009 | Jin | |
| 2010/0017225 A1 | 1/2010 | Oakley et al. | |
| 2010/0125190 A1 | 5/2010 | Fadem | |
| 2011/0015503 A1 | 1/2011 | Joffe et al. | |
| 2012/0083673 A1 * | 4/2012 | Al-Ali | A61B 5/0006 600/301 |
| 2012/0330125 A1 | 12/2012 | Wilson | |
| 2013/0172722 A1 | 7/2013 | Ninane et al. | |
| 2013/0253300 A1 | 9/2013 | Fadem | |
| 2014/0213874 A1 | 7/2014 | Tong | |
| 2014/0257073 A1 * | 9/2014 | Machon | A61B 5/6803 600/383 |
| 2014/0276183 A1 * | 9/2014 | Badower | A61B 5/0476 600/544 |
| 2015/0038808 A1 * | 2/2015 | Shimuta | A61B 5/0245 600/301 |
| 2015/0282760 A1 * | 10/2015 | Badower | A61B 5/04012 600/383 |
| 2016/0354005 A1 | 12/2016 | Oakley et al. | |
| 2018/0014741 A1 * | 1/2018 | Chou | A61B 5/0408 |

\* cited by examiner

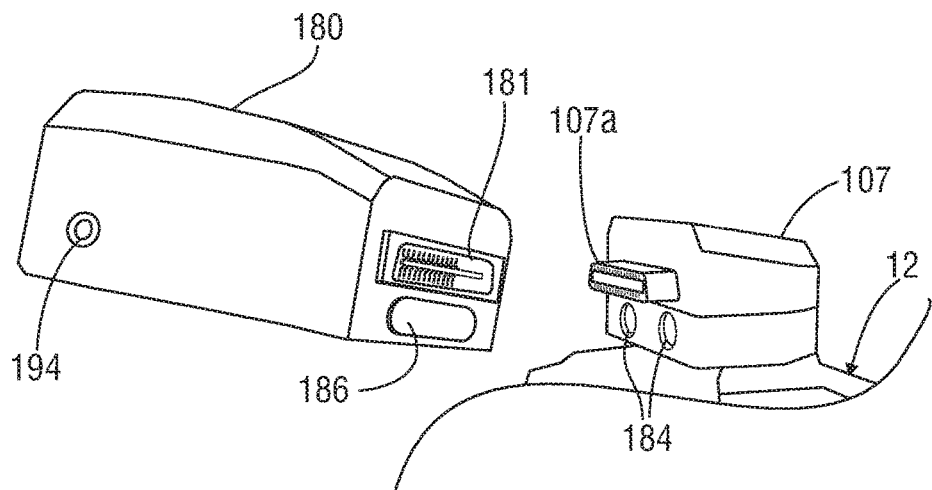
FIG. 30
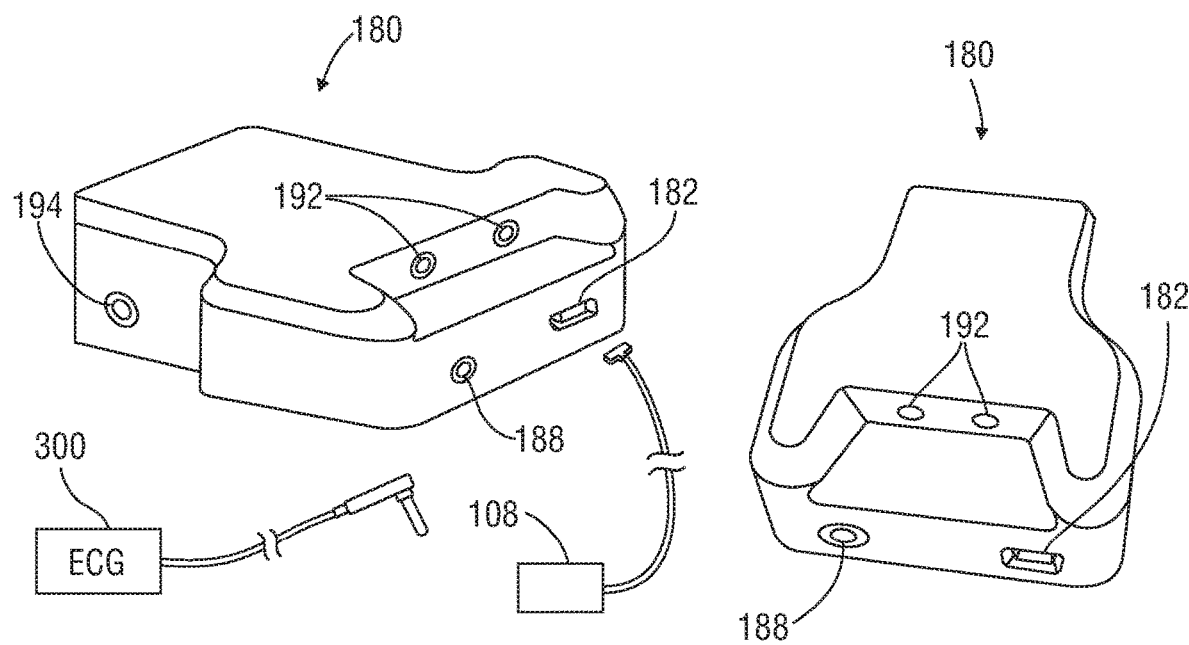
FIG. 31A
FIG. 31B

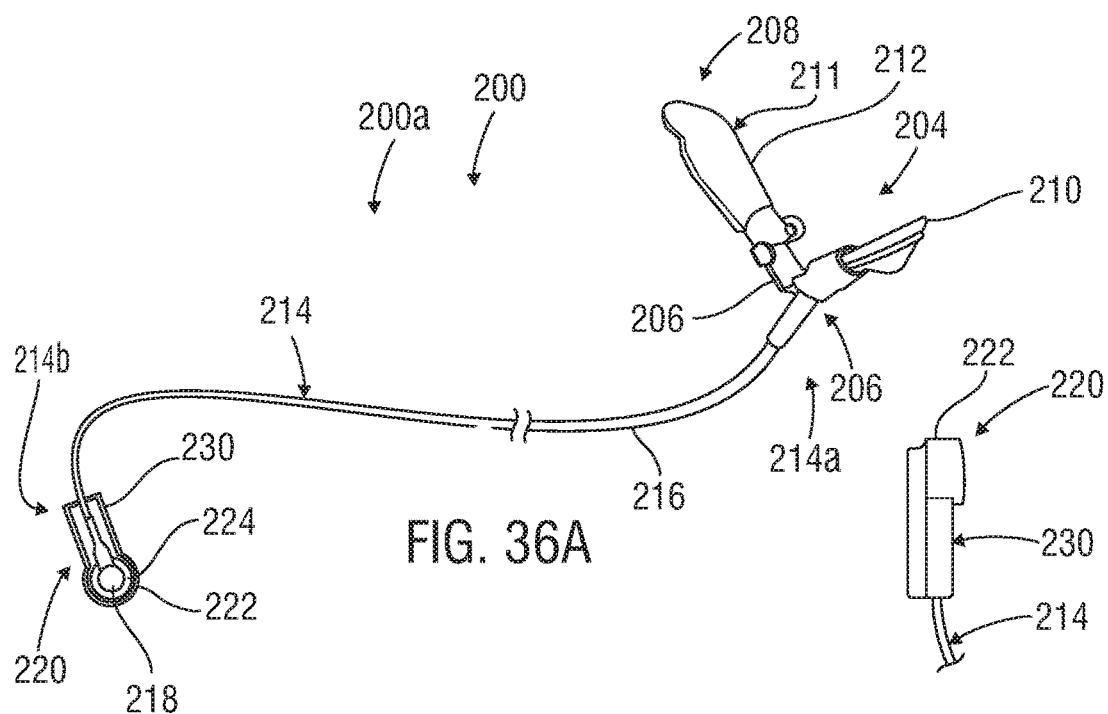
FIG. 36A
FIG. 36B
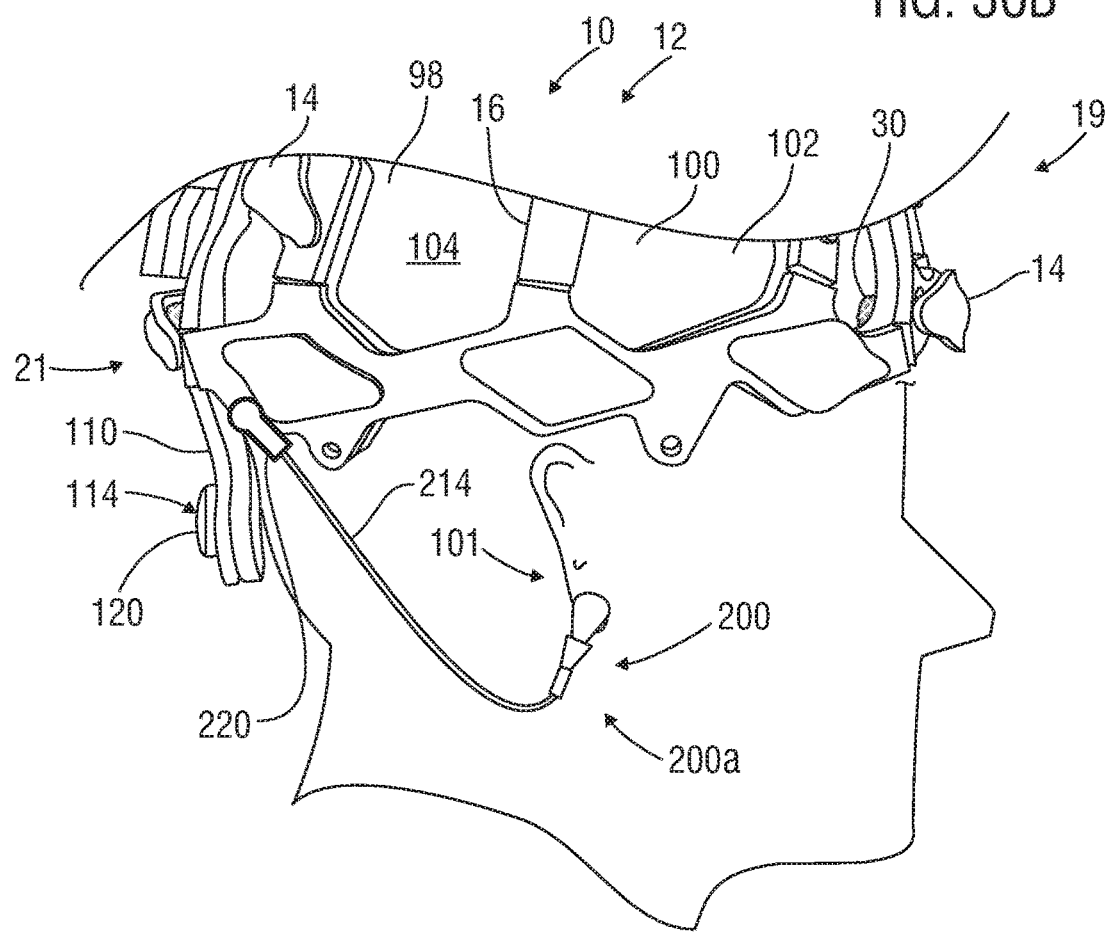
FIG. 37

US 11,311,228 B1

MULTI-FUNCTION APPARATUS, SYSTEMS AND METHODS FOR RECEIVING SIGNALS FROM A HUMAN SUBJECT'S HEAD

This application is a continuation-in-part application of and claims priority to U.S. patent application Ser. No. 15/163,292 filed on May 24, 2016 and entitled "Apparatus, Systems and Methods for Receiving Signals from a Human Subject's Brain", which claims priority to U.S. Provisional Patent Application Ser. No. 62/170,104 filed on Jun. 2, 2015 and entitled "Electrode Headset System", and U.S. Provisional Patent Application Ser. No. 62/196,066 filed on Jul. 23, 2015 and entitled "Electrode Headset System and Related Apparatus, Systems, Methods, Compositions and Articles of Manufacture", the entire contents of which are hereby incorporated by reference herein in their entireties.

FIELD OF THE DISCLOSURE

The present disclosure relates generally to apparatus, systems and methods for human medical diagnosis and/or physiological testing, and in some embodiments, apparatus, systems and methods useful for receiving signals from a human subject's head.

BACKGROUND

Taking brain activity data, brainwave measurements or the like, such as with known electroencephalographic ("EEG") technology, historically required attaching electrodes to shaved portions of a subject's scalp area and customizing the placement of each electrode for high conductivity in order to receive useful signals during the test. One solution to shaving a patient's head was to sew electrodes to an elastic cap that is fit tightly onto the subject's head, each electrode terminating permanently in a wire that is bundled with other wires and routed to an electrical connector.

Existing technology for receiving signals from a subject's brain are believed to possess one or more potential disadvantages. For example, in some instances with the use of known EEG headsets, an electrode positioned over an uneven, or indented, portion of the subject's head may not abut or conform thereto sufficient to conduct an electrical signal (e.g. EEG signal) from the scalp to a measuring device that is useful for the test. For another example, the hair style of the subject (e.g. cornrows) may not allow sufficient electrical conductivity from the scalp to each electrode. For still a further example, the solid cap typically covers the entire scalp area of the subject and therefore does not allow the administrator of the test to visually inspect or adjust the position of the cap or individual electrodes to make meaningful, timely adjustments to achieve sufficient electrical contact. In many cases, the caps fit tightly over the subject's hair and scalp and become soiled with dirt, oil, germs, etc., which may be transferred to subsequent subjects using the same headset. For still another possible example, the sewn-in electrodes may not be rotated or moved for improved contact and may not be easily replaced with a different size or style that better matches a subject's physiology. For yet another examples, known brain wave measurement technology, such as EEG headsets, do not incorporate other forms of medical diagnostic or physiological testing (other than taking brainwave measurements), such as for measuring or calculating vascular or cardiac parameters (e.g. pulse, heart rate, heart rate variability, pulse rate variability, pulse transit time, blood pressure, pulse wave amplitude, and the like). Yet other potential disadvantages of known technology will be apparent from the description below.

It should be understood that the above-described features, capabilities and disadvantages are provided for illustrative purposes only and are not intended to limit the scope or subject matter of the appended claims or those of any related patent application or patent. Thus, none of the appended claims or claims of any related application or patent should be limited by the above discussion or construed to address, include or exclude each or any of the above-cited features, capabilities or disadvantages merely because of the mention thereof herein.

Accordingly, there exists a need for improved apparatus, systems and methods useful for human medical diagnosis and/or physiological testing having one or more of the attributes or capabilities described or shown in, or as may be apparent from, the other portions of this disclosure.

BRIEF SUMMARY OF THE DISCLOSURE

In some embodiments, systems for use in connection with receiving electroencephalographic (EEG) signals from a human subject's head and taking one or more photoplethysmograms (PPG) of the subject includes a removable headset arranged and adapted to extend at least partially around the subject's head over at least part of the subject's scalp. The headset includes a plurality of electrode stations and at least one electrical signal transmission wire. A plurality of EEG electrodes is engageable with the electrode stations of the headset. During use of the headset, the EEG electrodes extend between the headset and the subject's scalp and are electrically coupled to at least one electrical signal transmission wire. At least one ear clip is releasably engageable with one of the subject's earlobes and includes at least one light transmitter and at least one light receiver positioned on opposite respective sides of the earlobe when the ear clip is engaged with the earlobe.

In various embodiments, a method of receiving electroencephalographic (EEG) signals from a human subject's head and taking one or more photoplethysmograms (PPG) of the subject includes placing a removable headset onto the subject's head so that the headset will extend at least partially around the subject's head over at least part of the subject's scalp. At least one non-conductive electrode biasing flap biases at least one EEG electrode between the headset and the subject's head. At least one EEG electrode facilitates the transmission of one or more EEG signals from the subject's head to at least one electrical signal transmission wire of the headset. An ear clip is releasably clamped to one of the subject's earlobes to take one or more PPG measurements of the subject.

This disclosure includes embodiments of systems for use in connection with receiving electroencephalographic (EEG) signals from a human subject's head through the scalp thereof with the use of a removable headset arranged and adapted to extend at least partially around the subject's head over at least part of the subject's scalp. A plurality of removable EEG electrodes are releasably engageable with the headset. During use of the headset, the EEG electrodes extend between the headset and the subject's scalp and are electrically coupled to the headset. At least one electrode biasing flap is constructed at least partially of flexible material and associated with each EEG electrode. At least one ear clip is releasably engageable with one of the subject's earlobes and includes an at least partially metallic EEG reference electrode electrically coupled to the headset during use of the ear clip.

In the present disclosure, there are embodiments of methods of using the immediately aforementioned system that include placing the headset onto the subject's head so that the headset will extend at least partially around the subject's head over at least part of the subject's scalp. At least some EEG electrodes in the headset facilitate the transmission of EEG signals from the subject's head to the headset.

In various embodiments, systems for use in connection with receiving electroencephalographic (EEG) signals from a human subject's head include a removable headset arranged and adapted to extend at least partially around the subject's head over at least part of the subject's scalp. A plurality of removable EEG electrodes are releasably engageable with the headset. During use of the headset, the EEG electrodes extend between the headset and the subject's scalp and are electrically coupled to at least one electrical signal transmission wire of the headset. A plurality of non-conductive electrode biasing flaps are separate and distinct from, and releasably engageable, with the headset and are each associated with at least one of the EEG electrodes. At least one ear clip is electrically coupled to at least one electrical signal transmission wire of the headset and releasably engaged with one of the subject's earlobes to serve as an EEG reference electrode as desired during use of the ear clip.

The present disclosure includes embodiments of methods of using the immediately aforementioned system involving placing the headset onto the subject's head so that the headset will extend at least partially around the subject's head over at least part of the subject's scalp. At least one electrode biasing flap biases at least one EEG electrode between the headset and the subject's head. At least some of the EEG electrodes facilitate the transmission of EEG signals from the subject's head to at least one electrical signal transmission wire of the headset. At least one ear clip is releasably engaged with at least one of the subject's earlobes and receives at least one electrical EEG reference signal from the earlobe and transmits it to at least one electrical signal transmission wire of headset.

In many embodiments, the present disclosure involves systems for use in connection with receiving electroencephalographic (EEG) signals from a human subject's head that include a removable headset arranged and adapted to extend at least partially around the subject's head over at least part of the subject's scalp. A plurality of removable EEG electrodes are releasably engageable with the headset and, during use of the headset, extend between the headset and the subject's scalp and are electrically coupled to the headset. A plurality of non-conductive electrode biasing flaps are associated with the EEG electrodes and are directly engaged with the headset separate from the associated EEG electrode(s). At least one ear clip is electrically coupled to the headset and releasably engaged with one of the subject's ear to receive electrical signals from the ear during use of the ear clip(s).

In various embodiments, methods of using the immediately aforementioned system include placing the headset onto the subject's head so that the headset will extend at least partially around the subject's head over at least part of the subject's scalp. At least one electrode biasing flap at least one EEG electrode between the headset and the subject's head. At least some of the EEG electrodes receiving electrical signals from the subject's head.

The present disclosure also includes embodiments of an apparatus for use in connection with receiving electroencephalographic (EEG) signals from a human subject's head through the scalp thereof. A removable headset is arranged and adapted to extend at least partially around the subject's head over at least part of the subject's scalp. The headset includes an inner side and an outer side, the inner side being closest to the subject's scalp when the headset is positioned least partially around the subject's head. The headset includes a plurality of electrode stations and a plurality of intermediate portions extending between the electrode stations and shaped and sized to form open spaces therebetween. Each electrode station has an electrode aperture extending therethrough from the outer side to the inner side of the headset. The headset further includes a plurality of biasing flaps, each biasing flap being coupled to the headset and at least partially aligned over one of the electrode apertures. The headset further includes at least one EEG signal transmission wire associated with the electrode stations for receiving EEG signals.

In these embodiments, a plurality of removable electrodes releasably are engageable with the headset and useful to facilitate the transmission of EEG signals from the subject's head to at least one the EEG signal transmission wire of the headset during use of the headset. Each electrode includes a top end, bottom end, at least one side extending therebetween and at least one protrusion extending outwardly from at least one side. The protrusion is arranged and adapted to selectively position the associated electrode relative to the associated electrode aperture. Each electrode is configured to be releasably suspended within one of the electrode apertures and biased towards the subject's head by the associated biasing flap. Each biasing flap includes a flap hole at least partially aligned over the associated electrode aperture. Each flap hole includes at least one groove configured to selectively retain at least one the protrusion of the associated electrode. When at least one protrusion is selectively secured in the groove of its associated biasing flap, the electrode is configured to be moveable with the biasing flap relative to the electrode aperture during use of the headset.

The present disclosure also includes embodiments of apparatus for use in connection with receiving electroencephalographic (EEG) signals from a human subject's head through the scalp thereof. A removable headset is arranged and adapted to extend at least partially around the subject's head over at least part of the subject's scalp. The headset includes an inner side and an outer side. The inner side is closest to the subject's scalp when the headset is positioned least partially around the subject's head. The headset includes a plurality of electrode stations and a plurality of intermediate portions extending between the electrode stations and shaped and sized to form open spaces therebetween. Each electrode station includes an electrode aperture extending therethrough from the outer side to the inner side of the headset.

In these embodiments, the headset further includes a plurality of biasing flaps. Each biasing flap is directly coupled to the headset and at least partially aligned over one of the electrode apertures. The headset further includes at least one EEG signal transmission wire associated with the electrode stations for receiving EEG signals. A plurality of removable electrodes are releasably engageable with the headset and useful to facilitate the transmission of EEG signals from the subject's head to at least one the EEG signal transmission wire of the headset during use of the headset. Each electrode includes a top end, bottom end and at least one side extending therebetween. Each electrode is configured to be releasably suspended within one of the electrode apertures and biased between the headset and the subject's head by the associated biasing flap. A plurality of electrode covers constructed at least partially of flexible, liquid-absorbing material are arranged and adapted to be electrically-conductive, receive EEG signals from the subject's head and transmit such signals to at least one the EEG signal transmission wire of the headset during use of the headset. Each electrode cover at least partially encapsulates an electrode and is laden with electrically-conductive liquid during use of the headset. Each biasing flap is configured to bias the associated electrode cover into contact with the subject's head to allow the associated cover to receive EEG signals from the subject's head.

In at least one embodiment, a method of using the immediately above-referenced apparatus includes releasably suspending the plurality of electrodes along with their associated electrically-conductive, liquid laden, electrode covers within the respective associated electrode apertures in the headset. The headset is placed on the subject's head. At least some of the biasing flaps bias their associated electrodes in the direction of the subject's head independent of the other electrodes in the headset. At least some of the electrode covers receive useful signals from the subject's head and transmit the received signals to at least one EEG signal transmission wire in the headset.

In some embodiments, the present disclosure involves apparatus for use in connection with receiving electroencephalographic (EEG) signals from a human subject's head through the scalp thereof. A removable headset is arranged and adapted to extend at least partially around the subject's head over at least part of the subject's scalp. The headset includes an inner side and an outer side, the inner side being closest to the subject's scalp when the headset is positioned least partially around the subject's head. The headset further includes a plurality of electrode stations and a plurality of intermediate portions extending between the electrode stations and shaped and sized to form open spaces therebetween. Each electrode station includes an electrode aperture extending therethrough from the outer side to the inner side of the headset. The headset further includes a plurality of biasing flaps and at least first and second flap fasteners associated with each biasing flap. Each biasing flap is coupled to the headset and at least partially aligned over one of the electrode apertures. The flap fasteners are adapted to secure the associated biasing flap to the headset on opposite sides of the associated electrode aperture. The headset further includes at least one EEG signal transmission wire associated with the electrode stations for receiving EEG signals.

In these embodiments, a plurality of removable electrodes are releasably engageable with the headset and useful to facilitate the transmission of EEG signals from the subject's head to at least one the EEG signal transmission wire of the headset during use of the headset. Each electrode includes a top end, bottom end and at least one side extending therebetween. Each electrode is configured to be releasably suspended within one of the electrode apertures and biased between the headset and the subject's head by the associated biasing flap. A plurality of electrode covers constructed at least partially of flexible, liquid-absorbing material is arranged and adapted to be electrically-conductive, receive EEG signals from the subject's head and transmit such signals to at least one the EEG signal transmission wire of the headset during use of the headset. Each electrode cover at least partially encapsulates an electrode and is laden with electrically-conductive liquid during use of the headset. Each biasing flap is configured to bias the associated electrode cover into contact with the subject's head to allow the associated cover to receive EEG signals from the subject's head.

In at least one embodiment, a method of using the immediately above-referenced apparatus includes releasably suspending the plurality of electrodes along with their associated electrically-conductive, liquid laden, electrode covers within the respective associated electrode apertures in the headset. The headset is placed on the subject's head. At least some of the biasing flaps bias their associated electrodes in the direction of the subject's head independent of the other electrodes in the headset. At least some of the electrode covers receive useful signals from the subject's head and transmit the received signals to at least one EEG signal transmission wire in the headset.

In certain embodiments, the present disclosure involves apparatus for use in connection with receiving electroencephalographic (EEG) signals from a human subject's head through the scalp thereof. A removable headset is arranged and adapted to extend at least partially around the subject's head over at least part of the subject's scalp. The headset includes an inner side and an outer side, the inner side being closest to the subject's scalp when the headset is positioned least partially around the subject's head. The headset also includes a plurality of electrode stations and a plurality of intermediate portions extending between the electrode stations and shaped and sized to form open spaces therebetween. Each electrode station includes an electrode aperture extending therethrough from the outer side to the inner side of the headset. The headset further includes a plurality of biasing flaps, each biasing flap being directly coupled to the headset and at least partially aligned over one of the electrode apertures. The headset further includes at least one EEG signal transmission wire associated with the electrode stations for receiving EEG signals.

In these embodiments, a plurality of removable electrodes is releasably engageable with the headset and useful to facilitate the transmission of EEG signals from the subject's head to at least one the EEG signal transmission wire of the headset during use of the headset. Each electrode includes a top end, bottom end, at least one side extending therebetween and at least one protrusion extending outwardly from at least one side. Each protrusion is arranged and adapted to selectively position the associated electrode relative to the associated electrode aperture. Each electrode is configured to be releasably suspended within one of the electrode apertures and biased towards the subject's head by the associated biasing flap.

In at least one embodiment, a method of using the immediately above-referenced apparatus includes releasably suspending the plurality of electrodes within the respective associated electrode apertures in the headset and placing the headset on the subject's head. At least some of the biasing flaps bias their associated electrodes in the direction of the subject's head independent of the other electrodes in the headset.

The present disclosure also includes embodiments involving apparatus for use in connection with receiving electroencephalographic (EEG) signals from a human subject's head through the scalp thereof. A removable headset is arranged and adapted to extend at least partially around the subject's head over at least part of the subject's scalp. The headset includes an inner side and an outer side, the inner side being closest to the subject's scalp when the headset is positioned least partially around the subject's head. The headset also includes a plurality of electrode stations and a plurality of intermediate portions extending between the electrode stations and shaped and sized to form open spaces therebetween. Each electrode station includes an electrode aperture extending therethrough from the outer side to the inner side of the headset. The headset further includes a plurality of biasing flaps and at least first and second flap fasteners associated with each biasing flap. Each biasing flap is coupled to the headset and at least partially aligned over one of the electrode apertures. The flap fasteners are adapted to secure the associated biasing flap to the headset on opposite sides of the associated electrode aperture. The headset further includes at least one EEG signal transmission wire associated with the electrode stations for receiving EEG signals.

In these embodiments, a plurality of removable electrodes are releasably engageable with the headset and useful to facilitate the transmission of EEG signals from the subject's head to at least one the EEG signal transmission wire of the headset during use of the headset. Each electrode includes a top end, bottom end, at least one side extending therebetween and at least one protrusion extending outwardly from at least one side. The protrusion is arranged and adapted to selectively position the associated electrode relative to the associated electrode aperture. Each electrode is configured to be releasably suspended within one of the electrode apertures and biased towards the subject's head by the associated biasing flap.

In at least one embodiment, a method of using the immediately above-referenced apparatus includes releasably suspending the plurality of electrodes within the respective associated electrode apertures in the headset and placing the headset on the subject's head. At least some of the biasing flaps bias their associated electrodes in the direction of the subject's head independent of the other electrodes in the headset.

Accordingly, the present disclosure includes features and advantages which are believed to enable it to advance the art of human medical diagnosis and/or physiological testing. Characteristics and advantages of the present disclosure described above and additional features and benefits will be readily apparent to those skilled in the art upon consideration of the following detailed description of various embodiments, the accompanying drawings and appended claims.

BRIEF DESCRIPTION OF THE DRAWINGS

The following figures are part of the present specification, included to demonstrate certain aspects of various embodiments of this disclosure and referenced in the detailed description herein:

FIG. 30 is an exploded perspective view of the exemplary connection unit of the headset system shown in FIG. 27 and an exemplary electronic processing unit ("EPU") useful therewith in accordance with an embodiment of the present disclosure;

FIG. 31A is another exploded perspective view of the exemplary EPU of FIG. 30;

FIG. 31B is yet another exploded perspective view of the exemplary EPU of FIG. 30;

FIG. 36A is a perspective view of an embodiment of an ear-clip assembly useful with headset systems in accordance with one or more embodiments herein;

FIG. 36B is a side view of part of the exemplary ear-clip assembly of FIG. 36A;

FIG. 37 is a partial side of the exemplary headset system of FIG. 27 with the exemplary ear-clip assembly of FIG. 36A coupled thereto;

DETAILED DESCRIPTION OF PRESENTLY PREFERRED EMBODIMENTS

Figure 1:
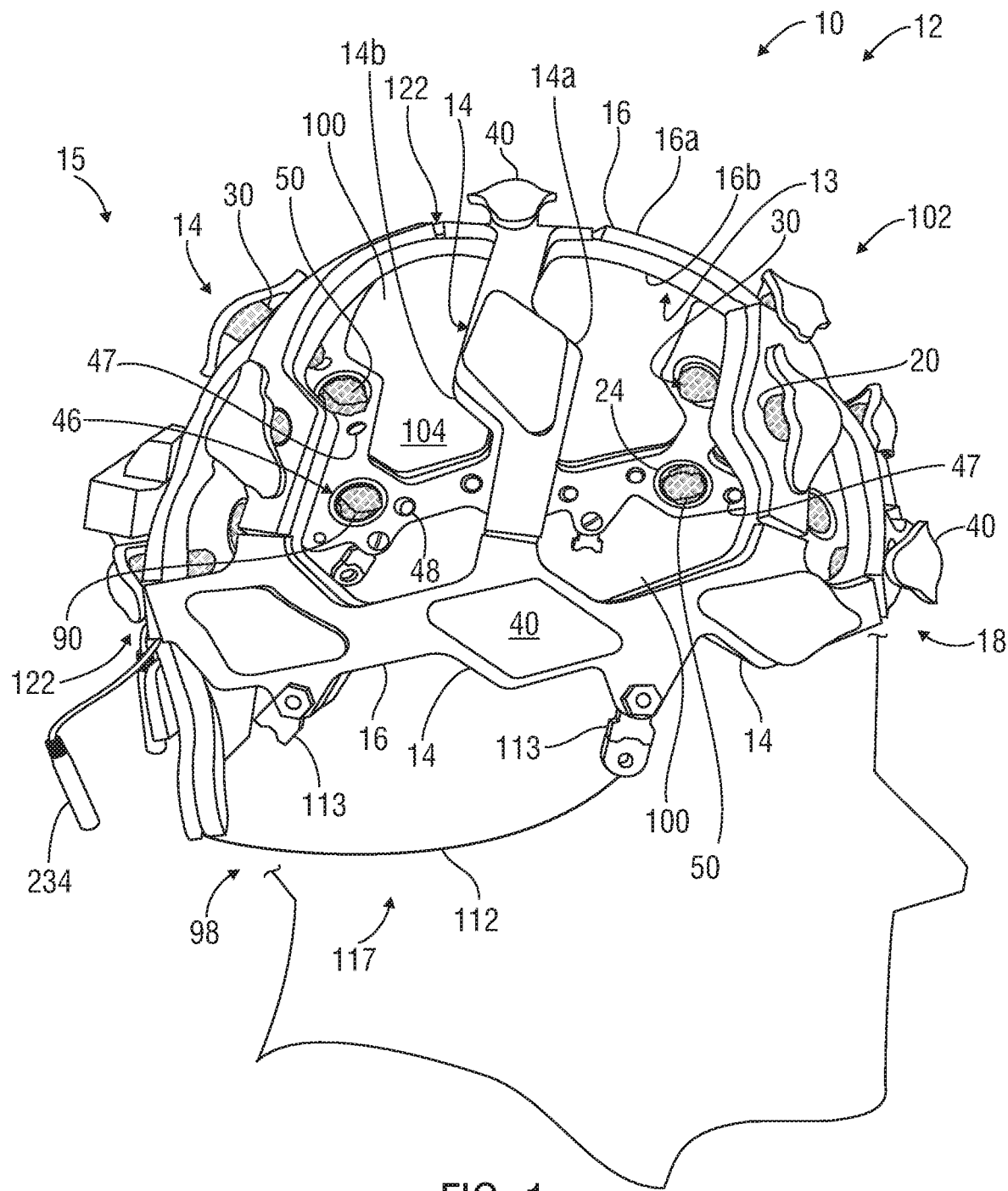
FIG. 1 is a side view of an exemplary signal receiving headset system shown as it would be positioned on a human subject's head in accordance with an embodiment of the present disclosure.

Characteristics and advantages of the present disclosure and additional features and benefits will be readily apparent to those skilled in the art upon consideration of the following detailed description of exemplary embodiments of the present disclosure and referring to the accompanying figures. It should be understood that the description herein and appended drawings, being of example embodiments, are not intended to limit the claims of this patent application or any patent or patent application claiming priority hereto. On the contrary, the intention is to cover all modifications, equivalents and alternatives falling within the spirit and scope of the claims. Many changes may be made to the particular embodiments and details disclosed herein without departing from such spirit and scope.

In showing and describing preferred embodiments in the appended figures, common or similar elements are referenced with like or identical reference numerals or are apparent from the figures and/or the description herein. When multiple figures refer to a component or feature with the same reference numeral, any description herein of the component or feature with respect to any of the figures applies equally to the other figures to the extent such description does not conflict with a description herein of the other figure(s). The embodiments shown in the figures are illustrated for simplicity and clarity and have not necessarily been drawn to scale. Also, common but well-understood components useful or necessary in the illustrated embodiments may not be depicted in the appended figures in order to facilitate a less obstructed view of other depicted features. Certain features and certain views of the figures may be shown exaggerated in scale or in schematic in the interest of clarity and conciseness.

As used herein and throughout various portions (and headings) of this patent application, the terms "invention", "present invention" and variations thereof are not intended to mean every possible embodiment encompassed by this disclosure or any particular claim(s). Thus, the subject matter of each such reference should not be considered as necessary for, or part of, every embodiment hereof, or of any particular claim(s) merely because of such reference. The terms "coupled", "connected", "engaged" and the like, and variations thereof, as used herein and in the appended claims are intended to mean either an indirect or direct connection or engagement. Thus, if a first device couples to a second device, that connection may be through a direct connection, or through an indirect connection via one or more other devices and/or connections.

Certain terms are used herein and in the appended claims to refer to particular components. As one skilled in the art will appreciate, different persons may refer to a component by different names. The use of a particular or known term of art as the name of a component herein is not intended to limit that component to only the known or defined meaning of such term (e.g. nut). Further, this document does not intend to distinguish between components that differ in name but not function. Also, the terms "including" and "comprising" are used herein and in the appended claims in an open-ended fashion, and thus should be interpreted to mean "including, but not limited to . . . ." Further, reference herein and in the appended claims to components and aspects in a singular tense does not necessarily limit the present disclosure or appended claims to only one such component or aspect, but should be interpreted generally to mean one or more, as may be suitable and desirable in each particular instance.

As used herein, the terms "substantially", "generally" and variations thereof means and includes (i) completely, or 100%, of the referenced parameter, variable or value and (ii) a range of values less than 100% based upon the typical, normal or expected degree of variation or error for the referenced parameter, variable or value in the context of the particular embodiment or use thereof, such as, for example, 90-100%, 95-100% or 98-100%. However, in some instances of the use of the terms "generally", "substantially" and variations thereof herein, the above definition may not apply, as should be apparent from the context of such use. It is also to be noted that the terms "comprising," "including," and "having" may be used interchangeably. As used herein and in the appended claims, the terms "elongated" and variations thereof mean having an overall length that is greater than its average width.

The following description is not to be taken in a limiting sense, but is made merely for the purpose of describing the general principles of exemplary embodiments; many additional embodiments of this disclosure are possible. The described features, structures, characteristics and other details of the present disclosure may be combined in any suitable manner in one or more embodiments. One skilled in the relevant art will recognize that the embodiments of the present disclosure may be practiced with our without one or more of the exemplary details provided herein, or with other methods, components, materials, and so forth.

Further, all numbers expressing dimensions, physical characteristics and so forth used in the specification and claims are to be understood as being modified in all instances by the term "about". Accordingly, unless explicitly indicated to the contrary, the numerical values set forth in the following specification and claims may vary depending upon the desired properties sought to be obtained by the practice of one or more embodiments of the disclosure. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.3, or 5.5 to 10, or 2.7 to 6.1.

For the purposes of promoting an understanding of the principles of the present disclosure, reference will now be made to the embodiments illustrated in the drawings.

Figure 2:
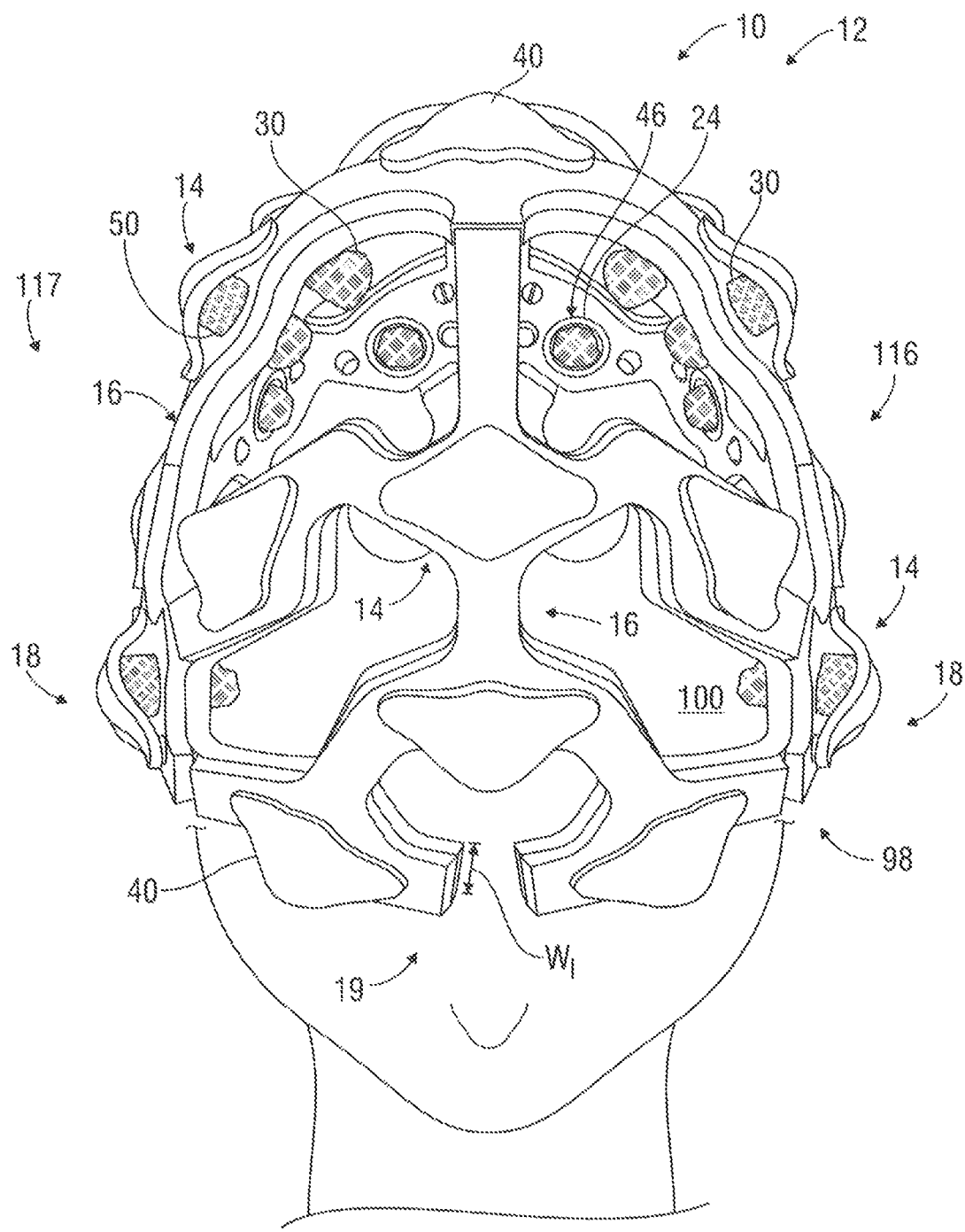
FIG. 2 is a front view of the exemplary headset system shown in FIG. 1.
Figure 3:
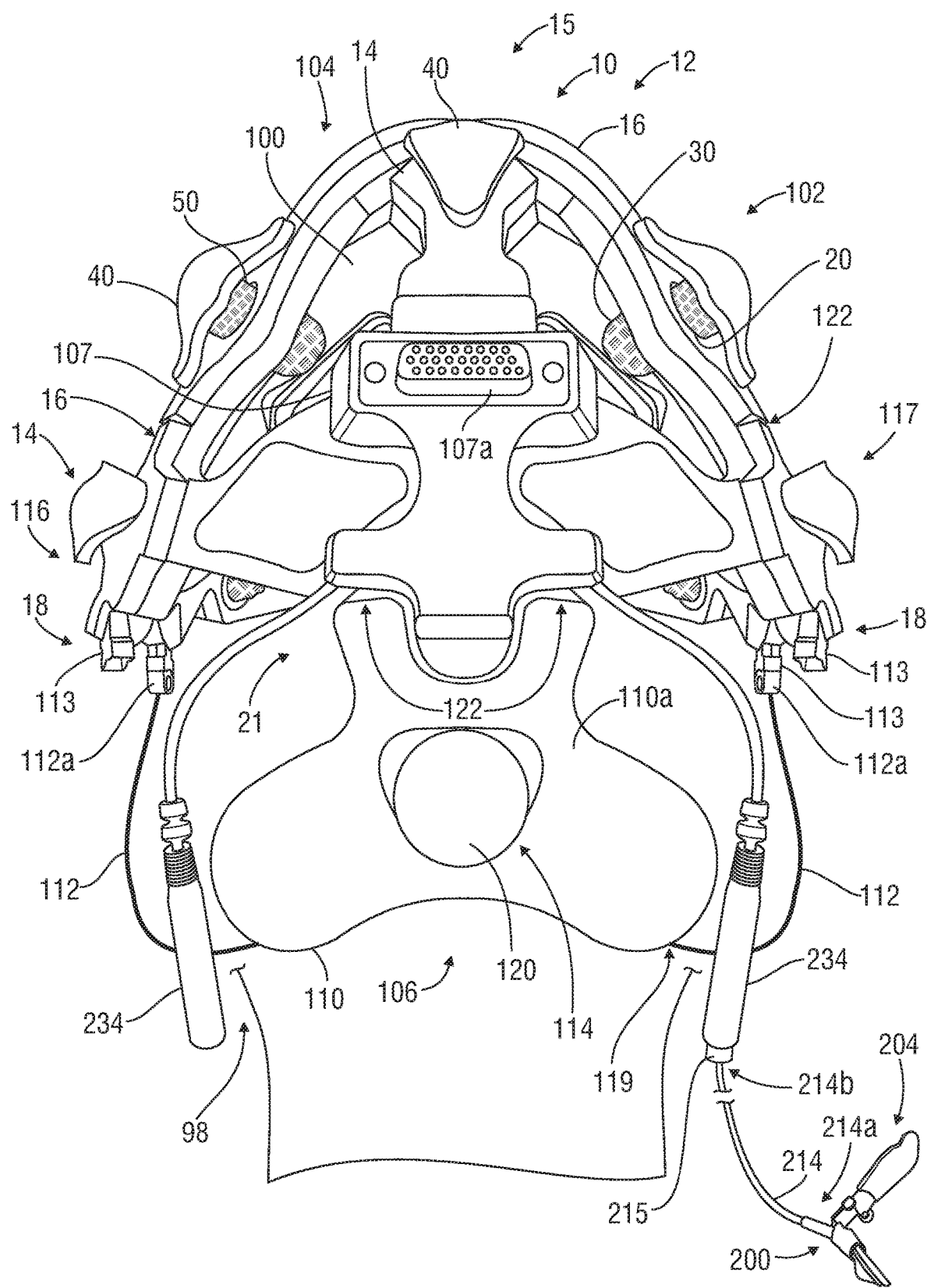
FIG. 3 is a rear view of the exemplary headset system shown in FIG. 1.

Referring initially to FIGS. 1-3, in an independent aspect of the present disclosure, an embodiment of a removable, re-suable signal receiving headset system 10 for receiving EEG signals (and/or other signals) from a human subject is shown. The exemplary system 10 includes a headset, or cap, 12 that is releasably securable at least partially around the subject's head 98 over at least part of the subject's scalp 102. As used herein, the terms "head", "cranium" and the like are used interchangeably. The exemplary headset 12 has an inner side 13 closest to the subject's scalp 102 when the headset 12 is positioned on the subject's head 98 and an outer side 15 that faces away from the scalp 102.

The cap 12 may have any suitable form, construction, configuration, components and operation. In this example, the cap 12 is a "webbed" cap and includes a plurality of electrode stations 14 and a plurality of intermediate portions, or strips, 16, for capping the area 104 of the subject's scalp 102 to be tested or measured (the "scalp test area" 104). The exemplary electrode stations 14 are associated with at least one signal transmission wire, or wire lead, 70 (e.g. FIG. 4) carried by the cap 12. Each illustrated electrode station 14 includes an electrode aperture 20 and an electrode biasing flap 40. Each exemplary electrode aperture 20 extends through the headset 12 from the outer side 15 to the inner side 13 thereof and is configured to suspend or carry a removable electrode 30 useful for facilitating the transmission of signals (e.g. EEG signals) from the subject's brain to one or more of the signal transmission wires 70. Typically, for EEG testing, the electrode apertures 20 are positioned at predetermined locations in the cap 12 for positioning the electrodes 30 at specific locations relative to the subject's brain. The illustrated biasing flap 40 is coupled to the outer side 15 of the headset 12, at least partially aligned over the associated electrode aperture 20 and configured to abut, or grip, and bias the associated electrode 30 in the direction of the subject's head 98.

The illustrated intermediate portions 16 generally extend between the electrode stations 14. While the portions 16 are also referred to herein as "strips" and may, in some instances, be elongated in shape, the portions 16 need not each take the shape of an elongated strip. Thus, as used herein, the terms "strip", "intermediate portion" and variations thereof generally means a section of the cap 12 disposed between, or adjacent to, one or more stations 14.

Figure 4:
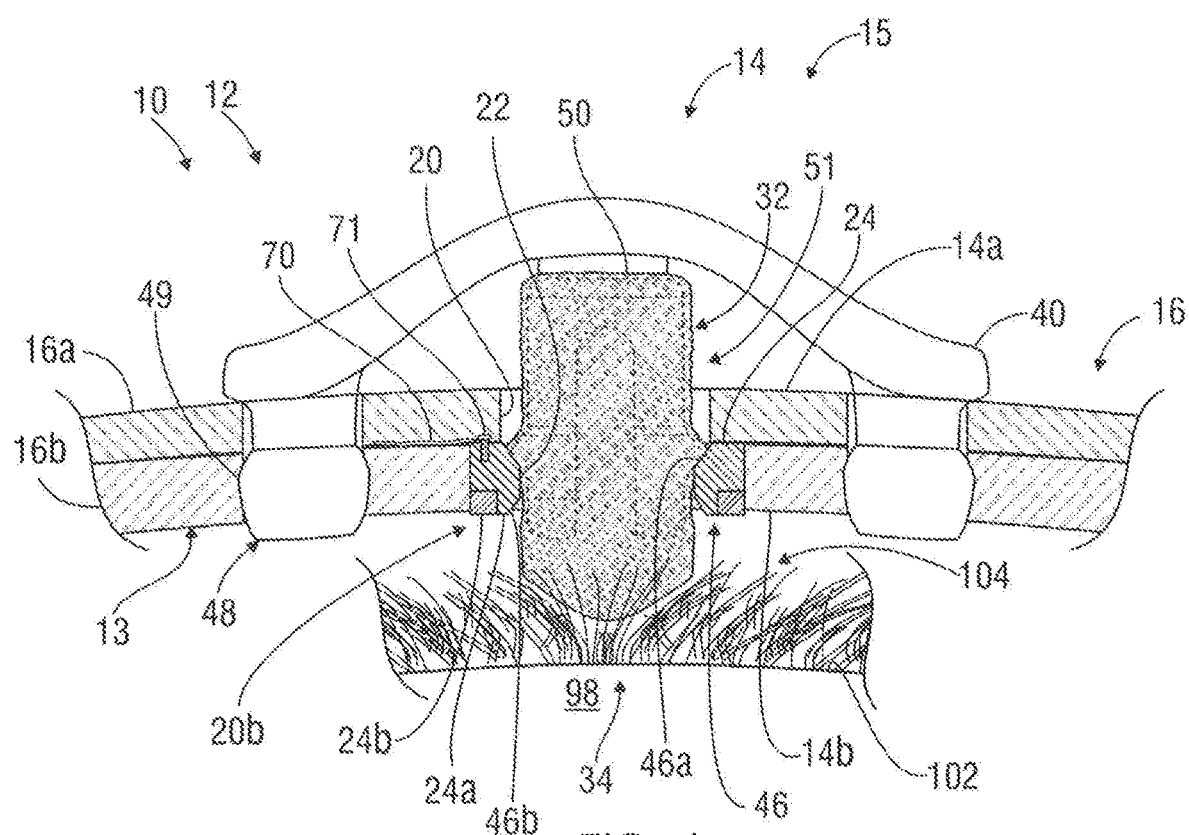
FIG. 4 is a partial cross-sectional view of part of the exemplary headset system of FIG. 1 showing an exemplary electrode is an exemplary retracted position relative to the illustrated exemplary electrode aperture.
Figure 5:
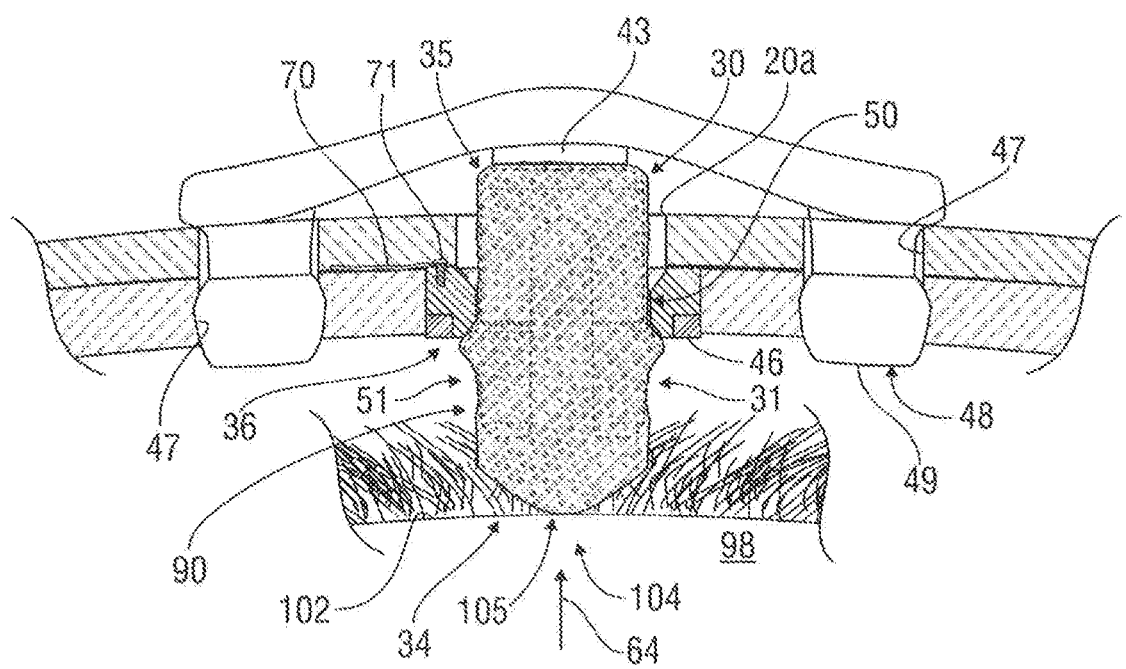
FIG. 5 is a partial cross-sectional view of part of the exemplary headset system of FIG. 1 showing the exemplary electrode of FIG. 4 in an exemplary extended position relative the illustrated exemplary electrode aperture.

Referring now to FIGS. 4-5, one of the exemplary electrodes 30 is configured to be releasably suspended in each electrode aperture 20 during use of the system 10. In this embodiment, the electrodes 30 are not glued or bonded to the headset 12. Each illustrated electrode 30 includes a top end 35, a bottom end 34, at least one side 31 extending therebetween and at least one outer side surface 32 extending at least partially along the side 31(s). The exemplary electrode 30 is configured to be biased between the headset 12 and the subject's head 98 by its associated biasing flap 30. The electrode 30 and/or one or more components related thereto are configured to receive signals (e.g. EEG signals) from the subject's brain and transmit such signals to at least one of the wire leads 70 of the headset 12.

In this embodiment, each electrode 30 is at least partially encapsulated by an electrode sock, or cover, 50 constructed at least partially of flexible, electrically-conductive liquid absorbing material. During use of the illustrated headset 12, each cover 50 is adapted to be laden with electrically-conductive liquid 90, electrically-conductive, at least partially sandwiched (by its associated biasing flap 40) between its associated electrode 30 and the subject's head 98 into contact with the subject's scalp test area 104 to receive signals (e.g. EEG signals) from the subject's head 98 and transmit them to at least one wire lead 70 of the headset 12. As used herein, the terms "laden" and variations thereof means sufficiently covered, soaked, saturated or near-saturated with one or more electrode wetting agents to allow the laden component to receive useful signals from the subject's brain through the head 98 and scalp 102 thereof. A useful signal is one that may be meaningfully used in the desired test/analysis (e.g. EEG measurement testing/analysis). As used herein, the terms "electrically-conductive liquid" and variations thereof mean and refer to liquids, gels and other suitable chemical combinations or formulations having properties that allow a component laden therewith to receive useful signals from the subject's head 98 and scalp 102. For example, each cover 50 may include a bottom end 52 that is electrically conductive to an exterior side surface 51 thereof. The exemplary bottom end 52 is configured to electrically-conductively engage the subject's head 98 to receive EEG signals therefrom, and the side surface 51 electrically conducts the received signals to one or more wire leads 70 in the headset 12.

In various embodiments, the electrodes 30 and/or covers 50 may be reusable, disposable or both. In some embodiments, the electrode covers 50 may not be included.

Referring back to FIGS. 1-3, the headset 12 and its related components may be constructed of any suitable material or combination of materials. For example, the cap 12 (e.g. electrode stations 14 and strips 16) and/or its related components or the outer layers thereof, may be constructed at least partially of one or more non-absorbent, water-resistant or water-proof materials (e.g. closed-cell foam) and/or easy-to-clean material. If desired, the cap 12 may be constructed of material that includes antimicrobial and/or biostatic agents. For example, depending upon the particular scenario, the stations 14 and strips 16 may be constructed of plastic, rubber, foam, Croslite™, silicon, Trileon™, any other type of EVA or a combination thereof. Croslite™ is a proprietary closed-cell, anti-microbial, resin material developed for Crocs™, Inc. Trileon™ is a closed-cell copolymer developed by Scott Seamans for SoftScience™, Inc. Such construction of the cap 12 and related components may be useful, for example, to avoid the transfer of sweat, dirt, germs, microbes and/or bacteria from one or more subjects' heads 98 to the cap 12 during use of the headset system 10 and/or to avoid problems caused thereby. For another example, such construction of the cap 12 and related components may render them re-usable on multiple subjects with minimal or no cleaning, to meet sanitary standards or requirements, and/or any other desired purpose(s).

Still referring to FIGS. 1-3, the electrode stations 14 and strips 16 may have any suitable form, configuration, construction and operation. For example, the electrode stations 14 may be integrally formed with the strips 16. In the illustrated embodiment, the electrode stations 14 are shown integral to the strips 16, have an overall generally diamond-shape and an average width that is greater than the average width of the exemplary strips 16. In other embodiments, the stations 14 may have an overall generally round, oval, rectangular, square or any other shape. In some embodiments, the stations 14 and strips 16 may be separate components that are interconnected in any suitable manner, such as with fasteners, adhesive or a combination thereof.

If desired, the strips 16 and/or stations 14 may be constructed of a material or combination of materials that is semi-rigid, conformable, resilient, elastic or a combination thereof. Also if desired, the strips 16 and/or stations 14 may be constructed and shaped to provide a desired mix of compressive, elastic, bending, flexing and conforming properties. For example, the width of the strips 16 may be selected to assist in providing the desired flexibility thereof. In the embodiment of FIGS. 1-5, the average width $W_1$ (FIG. 2) of each illustrated strip 16 ranges from approximately ¼ inch-approximately ¾ inch, and is preferably approximately ½ inch. However, the illustrated strips 16 may have any other desired width.

For another example, some or all of the electrode stations 14 and/or strips 16 may be formed of multiple layers. In this embodiment, the stations 14 and strips 16 are each formed of two layers, the electrode stations 14 having upper and lower layers 14a, 14b and the strips 16 including upper and lower layers 16a, 16b. Multiple layers may be included for any suitable purpose. For example, multiple layers of stations 14 and/or strips 16 may provide the desired combination of stiffness and flexibility of the stations 14 and/or strips 16. In this embodiment, two layers of flexible Croslite™, Trileon™ or other antimicrobial material for the stations 14 and/or strips 16 may provide the desired combination of stiffness and flexibility of the headset 12. For another example, multiple layers may provide the desired protection of internally disposed components of the headset 12, such as the wire leads 70.

Figure 6:
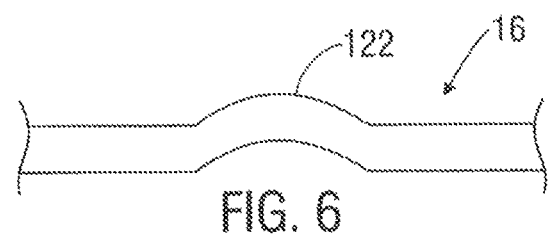
FIG. 6 is a partial side view of an exemplary intermediate portion of an embodiment of a headset system having a fold-type flex point in accordance with an embodiment of the present disclosure.
Figure 7A:
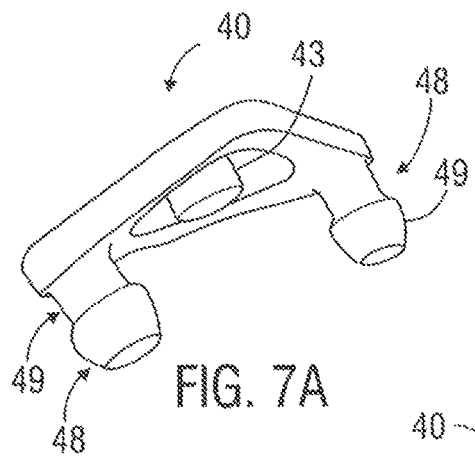
FIG. 7A is a perspective view of an exemplary electrode biasing flap useful in the exemplary headset system shown in FIG. 1 in accordance with an embodiment of the present disclosure.
Figure 7B:
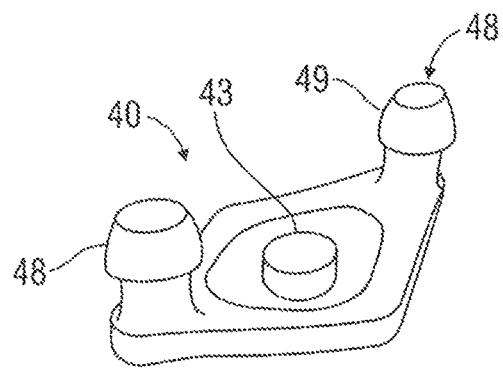
FIG. 7B is another perspective view of the exemplary electrode biasing flap shown in FIG. 7A.
Figure 7C:
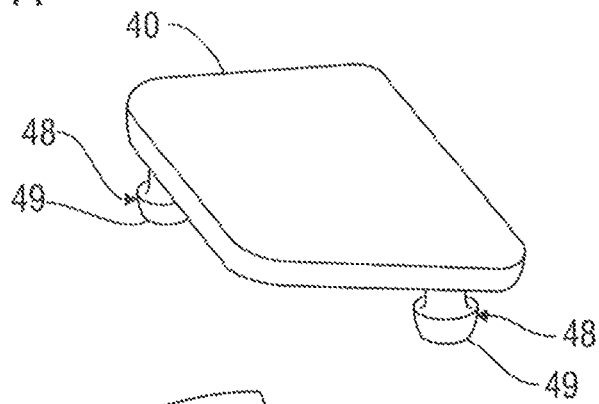
FIG. 7C is yet another perspective view of the exemplary electrode biasing flap shown in FIG. 7A.
Figure 8:
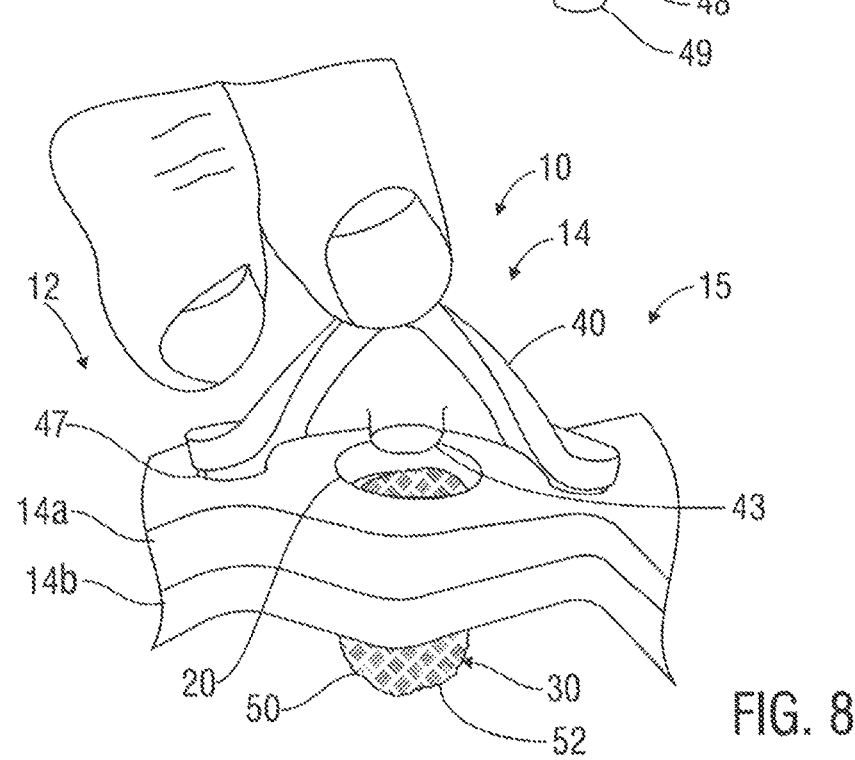
FIG. 8 is a side view of part of the part of the exemplary headset system of FIG. 1 showing an exemplary electrode biasing flap being manually stretched upwardly to show the underside thereof.

In many embodiments, some or all of the strips 16 may be constructed and configured to enhance the flexibility of the strips 16 and headset 12, allow the strips 16 to be compressed or conform to the shape of the subject's head 98 or a combination thereof. For example, one or more of the strips 16 may include one or more flex points 122 formed or provided therein. In the illustrated example, each flex point 122 is a break in the outer layer 16b of some of the strips 16. In other embodiments, such as shown in FIG. 6, the illustrated flex point 122 is a bend or fold in the strip 16. Depending upon the configuration, the exemplary flex point(s) 122 may, for example, allow the strips 16 to displace upwardly or downwardly, such as when one end of the strip(s) 16, or headset 12, is squeezed or pushed towards its other end, avoiding twisting, bulging or buckling and/or assisting in preserving the conformance of the cap 12 to the subject's head 98.

Figure 18:
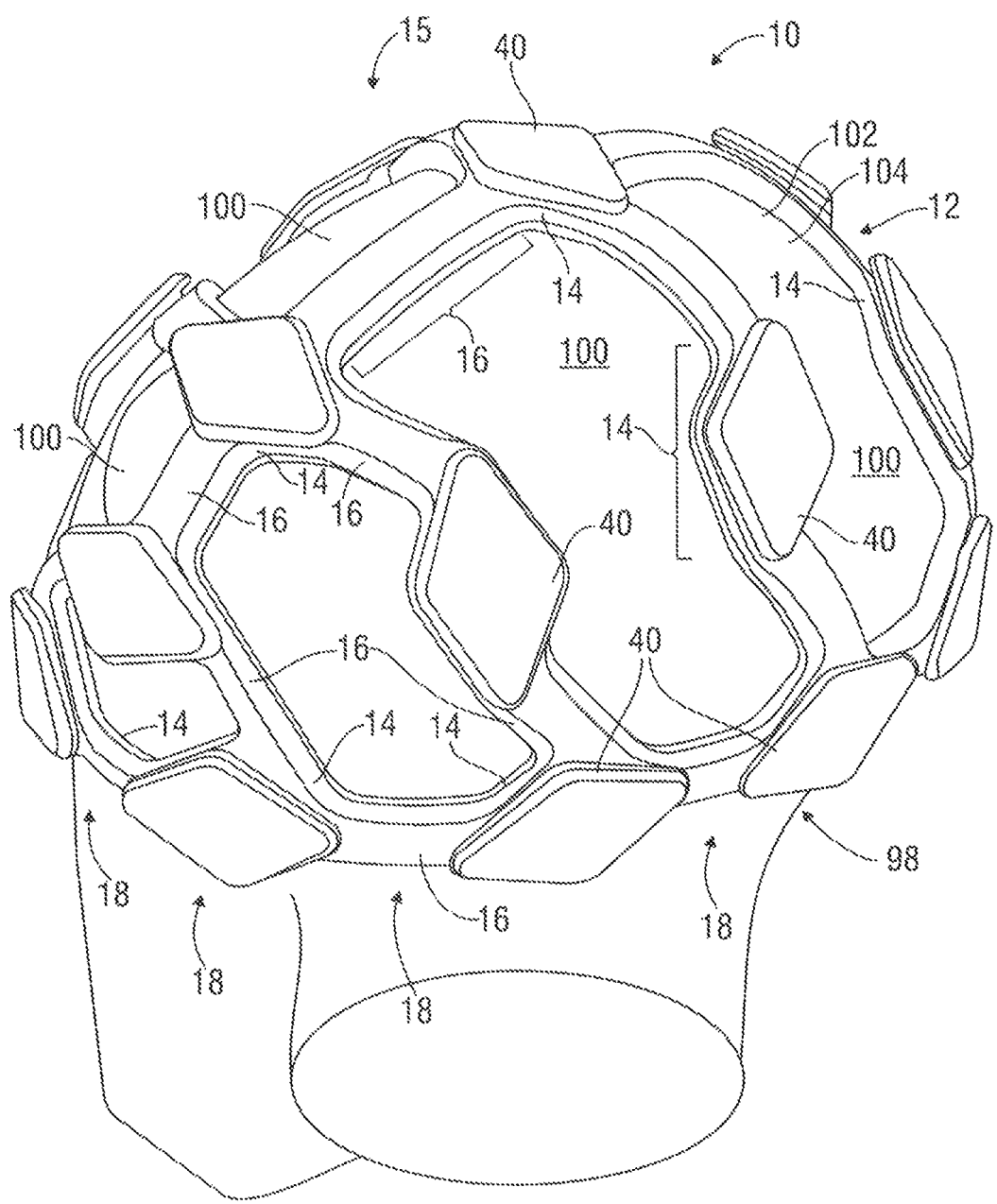
FIG. 18 is a perspective view of an exemplary signal receiving headset system shown positioned on a human subject's head in accordance with another embodiment of the present disclosure.

Still referring to FIGS. 1-3, the electrode biasing flaps 40 may have any suitable form, configuration and operation. For example, the flaps 40 may be constructed at least partially of rubber, foam, foam rubber, a rubbery material, closed-cell foam, Croslite™, impact-absorbing elastic, or any other material suitable for flexing and returning to its original position, resiliently biasing the electrode 30 downwards toward the scalp 102 as desired and is otherwise suitable for use as part of the system 10. The flaps 40 may be positioned to partially, or entirely, cover, or align over, the respective electrode apertures 20 of their associated electrode stations 14. In this embodiment, each flap 40 is unperforated, or solid, above its associated electrode aperture 20 and aligns generally entirely over the aperture 20 (see also, FIG. 18). If desired, the flap 40 may include at least one nipple 43 (e.g. FIGS. 7A-C and FIG. 8) configured to abut and apply biasing forces to the top end 35 of an electrode 30.

In other embodiments, such as shown in FIGS. 12-15, the flap 40 may align over only part of the associated electrode aperture 20. In this example, the solid part of the exemplary flap 40 aligns over only the upper edge 20a of the aperture 20 because the flap 40 includes a flap hole 42. The flap hole 42 may have any suitable form, construction and configuration. In this embodiment, the flap hole 42 aligns over the electrode aperture 20 of the associated electrode station 14 and is configured to also suspend or carry the associated electrode 30. The flap hole 42 may also have any desired operation. For example, the flap hole 42 may be large enough to allow the passage of an electrode 30 therethrough and/or configured to assist in the positioning of the electrode 30 (e.g. FIGS. 16A-C), such as will be described further below.

Referring again to FIGS. 4-5, the flaps 40 may be engaged with the headset 12 in any suitable manner. For example, each flap 40 may be releasably or permanently fastened to an electrode station 14 and/or one or more strips 16 with flap fasteners 48. The flap fasteners 48 may have any suitable form, configuration, construction and operation. In this embodiment, the flap fasteners 48 are barbed, or arrow-shaped, extensions 49 integrally formed in the flap 40 on opposing sides, or corners, thereof (see also, FIGS. 7A-C). For connection with the cap 12, each illustrated extension 49 releasably extends into and engages a barb-receiving hole 47 formed in an electrode station 14 or strip 16 (see also, FIG. 8). In this embodiment, the barb-receiving holes 47 extend through both layers 14a, 14b of the associated station 14 (or layers 16a, 16b of the associated strip 16), such as to ensure a secure fit during stretching, biasing and other movement (e.g. twisting) of the flaps 40 when the headset 12 is in use. Further, the exemplary fasteners 48 are removable from the headset 12. In other embodiments, the flap fasteners 48 may instead be permanently fixed to the headset 12.

In the embodiment of FIGS. 13 and 16A-C, the flap fasteners 48 are removable threaded plastic bolts 56 secured upwardly into receiving nuts 53. The electrode-biasing flaps 40 may instead, or also, be secured to the headset 12 using one or more adhesives. It should be noted that, in some embodiments, the headset 12 may include one or more springs or other forms of elastic elements used in combination with or instead of the flaps 40 for biasing the electrodes 30 downwardly into contact with the subject's head 98.

In another independent aspect of the present disclosure, referring back to FIGS. 4-5, the electrodes 30 may be inserted and removed from the headset 12 in any suitable manner. In some embodiments, the electrodes 30 are configured to be moveable into and out of the electrode apertures 20 in both directions. In the present embodiment, since the electrode biasing flap 40 is solid above the aperture 20, insertion or removal of the electrode 30 from the top, or outer side 15, of the headset 12 would require disengaging at least one of the flap fasteners 48 of each flap 40 to move the flap 40 away from the electrode aperture 20. Thus, the easier and quicker technique for inserting and remove the electrodes 30 in this embodiment is to insert the electrode 30 up into the electrode aperture 20 from below (from the inner side 13 of the headset 12) and remove it back down through the aperture 20 (in the direction of the inner side 13 of the headset 12). Similarly, in the embodiment of FIGS. 19A-C, the electrode 30 is inserted upwardly (arrows 58) into the aperture 20 and can be later removed downwardly in the reverse direction.

In the embodiment of FIGS. 13-16C, the illustrated electrodes 30 are also moveable in both directions into and out of the headset 12 because the flaps 40 each include a flap hole 42 through which the electrode 30 may pass. However, in this particular arrangement, the electrodes 30 are preferably insertable into the headset 12 from the top, or outer side 15, of the headset 12 (arrows 60, FIGS. 16A-B) and removed in the same direction (toward the inner side 13 of the headset 12). The electrodes 30 of this embodiment are thus preferably moveable in one direction only.

Referring back to FIGS. 1-3, in another independent aspect of the present disclosure, in some embodiments, the exemplary headset 12 may include one or more base sections, or cap rims, 18 that at least partially aligns over and around a lower area of the subject's head 98. The cap rim 18 may have any desired form, components and construction and may be configured for any desired purpose. For example, the cap rim 18 may be configured to provide tension to assist in the placement and/or positioning of the electrodes 30 relative to the scalp test area 104.

If desired, the cap rim 18 may include some of the electrode stations 14 interconnected by intermediate sections 16. In some embodiments, the cap rim 18 at the front end 19 of the headset 12 (e.g. FIG. 2) may be open. In this example, two or more intermediate sections 16 and/or electrode stations 14 at the front end 19 along the cap rim 18 of the headset 12 are not connected, such as to provide the desired flexibility of the headset 12, assist in achieving a good fit to the subject's head 98, and/or other suitable purpose. In various embodiments, the cap rim 18 at the rear end 21 or either side 116, 117 of the headset 12, or a combination, thereof may be open (not shown).

Figure 29:
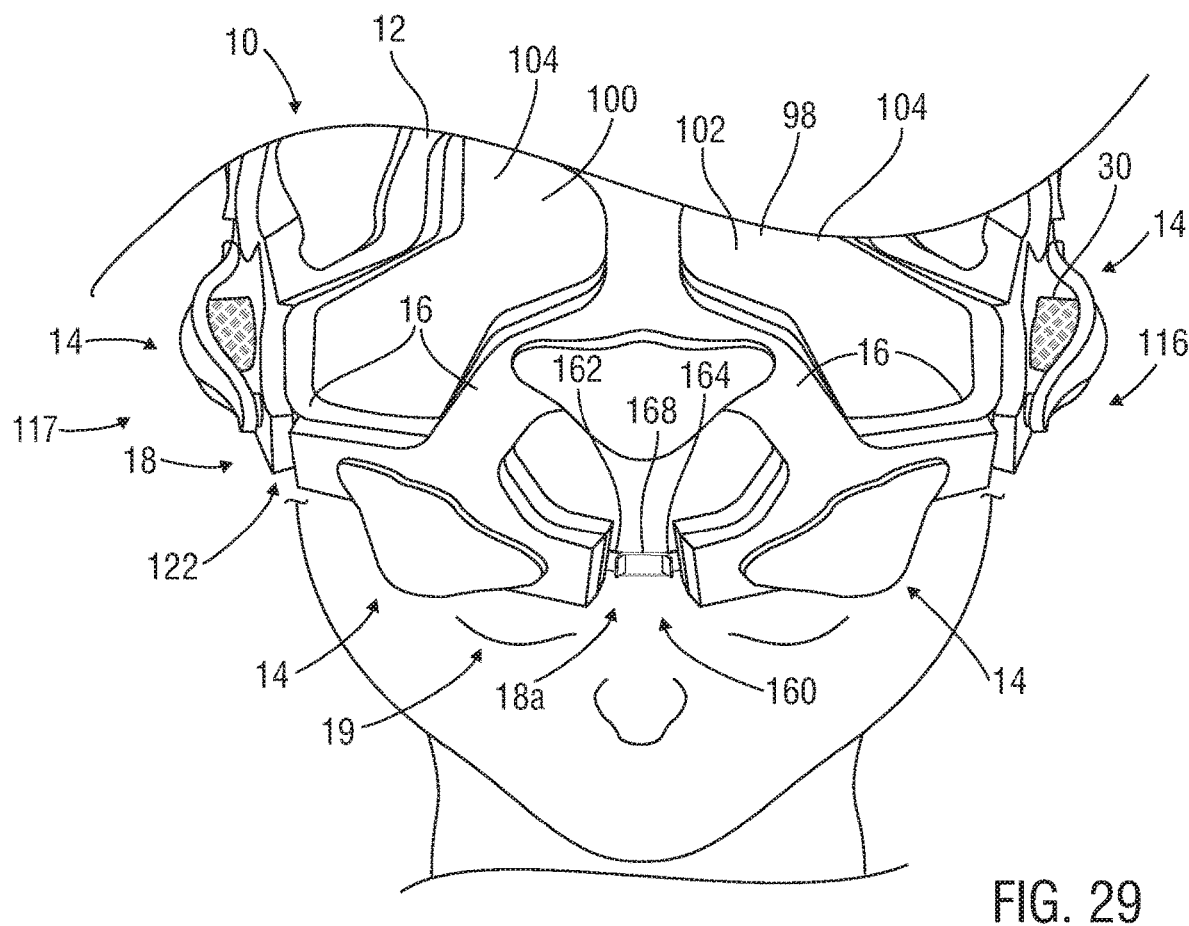
FIG. 29 is a partial front view of the exemplary headset system shown in FIG. 27.

If the cap rim 18 is open at any location, one or more releasable connectors, such as a pair of mateable velcro straps, or snap connectors, may be included to adjustably connect the adjacent open sections of the rim 18, such as to assist in securing the headset 12 to the subject's head 98. For example, in FIG. 29, at least one open section, or space, 18a is formed in the cap rim 18 at the front 19 of the headset 12 (between two or more adjacent, spaced-apart electrode stations 14 and/or intermediate sections 16). In this embodiment, a front tautener 160 is provided proximate to the space 18a to draw the headset 12 (e.g. the spaced-apart two or more adjacent electrode stations 14 and/or intermediate sections 16) at least partially over the at least one space 18a and assist in tightening the front 19 of the headset 12 to the subject's head 12, securing the headset 12 to the subject's head 98, improving contact between one or more parts of the headset 12 and the subject's head 98, other desired purpose or a combination thereof. The front tautener 160 may have any suitable form, configuration and operation. In this embodiment, the front tautener 160 includes first and second clips 162, 164 which are selectively engageable together to draw the cap rim 18 closer together at least partially across the open section 18a. For example, an elastic band 168 (e.g. rubber band) is shown extended between the clips 162, 164. In other embodiments, the clips 162, 164 may be releasably mateable or engageable with one another or coupled together as desired. It should be noted, however, that when the front tautener 160 is included, it may not necessarily be utilized depending upon the particular circumstances (e.g. shape of the subject's head 98, hair style, etc.).

In some embodiments, the cap 12 may be adjustably tightened around the circumference of the subject's head 98 and/or along one or more sides thereof to achieve a desired fit or for any other desired purpose. The cap 12 may be adjustably tightened in any suitable manner. For example, the cap 12 may be adjustably tightened around the cap rim 18. Referring specifically to FIG. 3, in this embodiment, the cap 12 is configured with a closure mechanism, or tightener, 114 useful to assist in tensioning or positioning the headset 12 as desired on the subject's head 98, moving the headset 12 down and around the head, adequately positioning the electrodes 30 (e.g. FIGS. 4-5) as desired (e.g. approximately perpendicular) relative to the scalp test area 104 without the need for a chin strap, any other suitable purpose or a combination thereof.

The tightener 114 may have any suitable form, configuration, components and operation. For example, may one or more wires, or cables, 112 extending from each side 116, 117 of the headset 12, or along the rim 18, may be selectively tightened and/or loosened. In the illustrated example, the tightener 114 includes a ratcheting spool 120 mounted on a platform 110 and upon which a cable 112 coupled to each side 116, 117 is wound. In the illustrated embodiments, the platform 110 is configured to provide a desired combination of stiffness of the platform 110 (e.g. to adequate to support the exemplary tightener 114) and flexibility, such as to allow the platform 110 to flex and/or move to accommodate or fit the shape of the subject's head 98, allow tightening of the headset 12 to subject's head 98 when tightening one or more of the cables 112 or other desired purpose. For example, the platform 110 may be formed of multiple layers (e.g. upper and lower layers 110a, 110b, FIGS. 3 & 32) of the same or similar material as the strips 16 and/or electrode stations 14 (e.g. plastic, rubber, foam, Croslite™, silicon, Trileon™, any other type of EVA) or combination of materials that have any one or more of the possible characteristics that the strips 16 and electrode stations 14 as described above (e.g. conformable, resilient, elastic, non-absorbent, water-resistant, water-proof, antimicrobial, re-usable, easy to clean and/or requires minimal cleaning, meets sanitary standards or requirements or a combination thereof).

Figure 27:
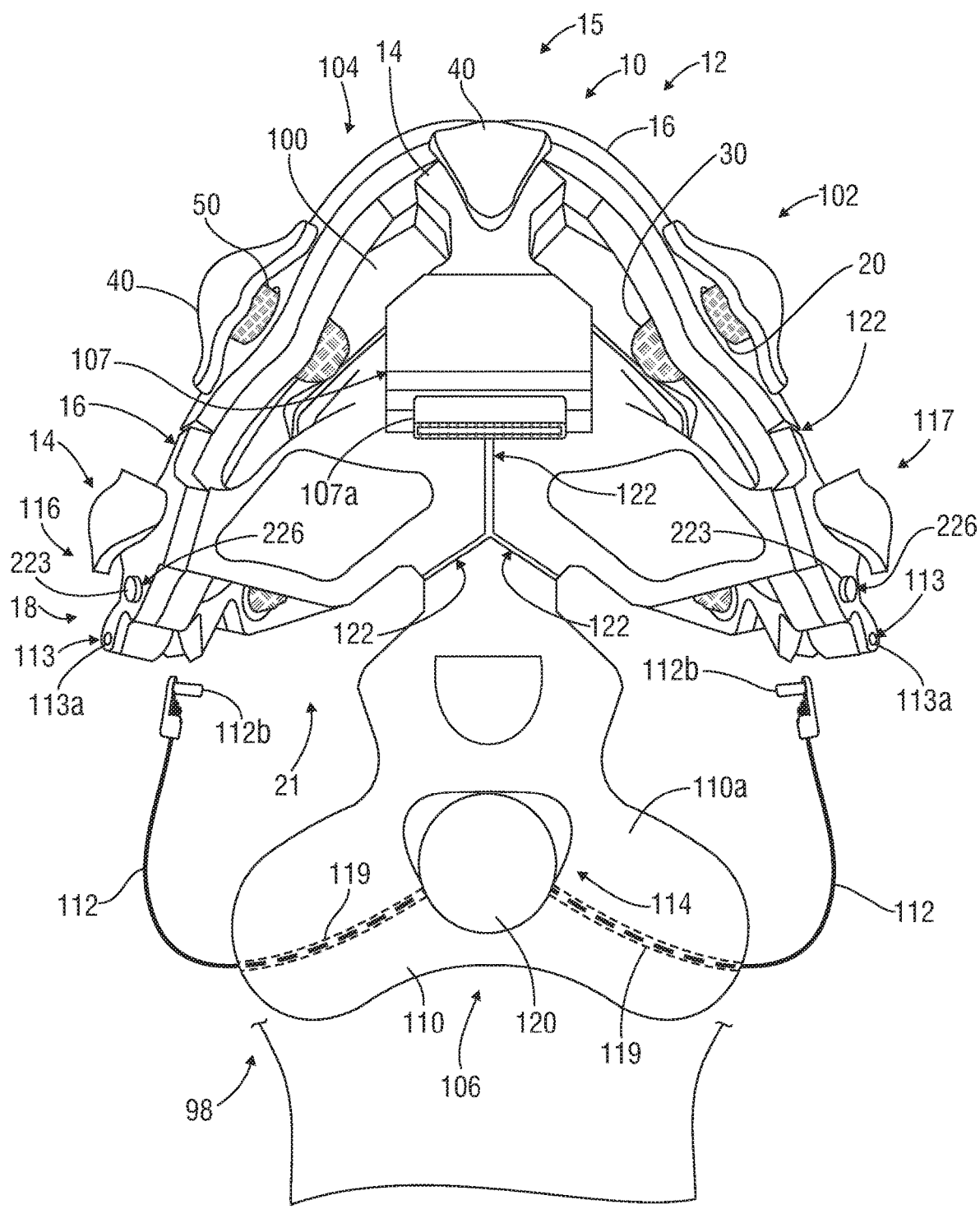
FIG. 27 is a rear view of another embodiment of a signal receiving headset system shown as it would be positioned on a human subject's head in accordance with an embodiment of the present disclosure.

Referring to FIGS. 3 & 27, one or more flex points 122 may be formed in or adjacent to the exemplary platform 110, such as to allow or enhance the flexibility of the platform 110 as described above (e.g. to allow the headset 12 to conform to the shape of the subject's head 98) and/or any other desired purpose. In the illustrated embodiments, the lower layer 110b (e.g. FIG. 32) of the platform 110 is a continuation of the lower layer(s) 14b, 16b of the immediately adjacent electrode stations 14 and/or strips 16, and at least one flex point 122 is provided between the upper layer 110a of the platform 110 (e.g. FIGS. 3 & 27) and the adjacent electrode stations 14 and/or strips 16.

If desired, the platform 110 may be positioned proximate to the occipital area 106 of the subject's head 98, such as for support and comfort. The exemplary ratcheting spool 120 is rotated to draw in and tension the cable 112 and draw the headset sides 116, 117 toward the rear. If desired, the ratcheting spool 120 may be configured to also loosen the cable(s) 112. The ratcheting spool 120 may constructed of any suitable material, such as plastic. For example, the ratcheting spool 120 may be a commercially available spool commonly used in sports equipment (e.g. a bolo, or boa, type ratchet).

Figure 28:
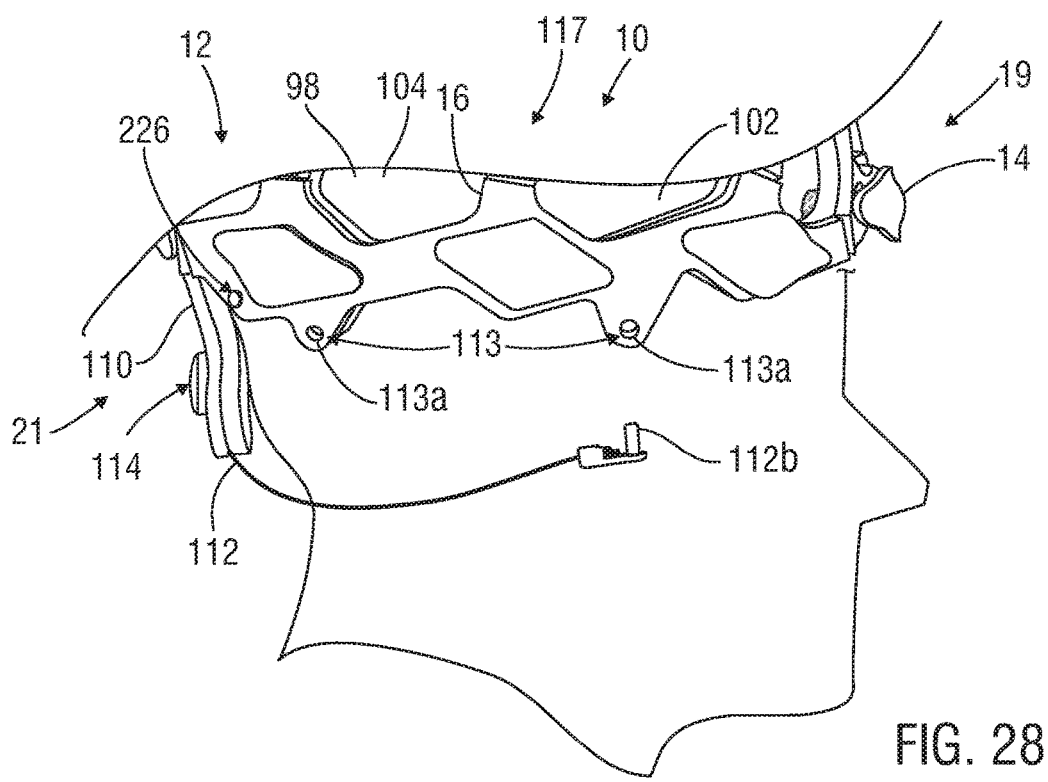
FIG. 28 is a partial side view of the exemplary headset system shown in FIG. 27.

Still referring to the embodiment of FIG. 3, if desired, the cables 112 may be selectively connectable to the headset 12 at different positions to achieve the desired effect. The cables 112 may be connectable to the headset 12 in any suitable manner. In this embodiment, each cable 112 may be snap fit into one among multiple receivers 113 disposed at different positions along the cap rim 18. For example, two receivers 113 are shown provided at different positions along the each side 116, 117 of the headset 12 around the cap rim 18. The illustrated cables 112 each include a clip 112a configured to snap into locking engagement with either receiver 113 on the same respective side of the headset 12 and squeezed and moved away from the associated receiver 113 for disengagement therefrom. In the embodiment of FIGS. 27-28, each receiver 113 includes at least one hole 113a formed in the headset 12, and each cable 112 includes at least one post 112b (e.g. pin) that is configured to be inserted into any of the holes 113a (e.g. on the same side 116, 117 of the headset 12 for engagement therewith.

Referring again to FIG. 3, in some embodiments, one or more cable channels 119 may be formed in the platform 110. Further, if desired, the cables 112 may extend through one or more guides, or pulleys, 118 (e.g. FIGS. 20A-B). In various embodiments, the cable(s) 112 may be connected to a chin strap and/or comprise complementary Velcro® straps fastenable to each other. For example, in FIGS. 34-35, the exemplary cables 112 are connectable to a chin strap 130 extendable around the subject's chin 99, such as to assist in securing the headset 12 to the subject's head 98, tightening the headset 12 around the circumference of the subject's head 98, enhancing the fit of the headset 12 to the subject's head 98 (e.g. pull the headset 12 down and more forward or centered on the subject's head 98 than without the use of the chin strap 130 or similar component), any other desired purpose or a combination thereof. The exemplary chin strap 130 may have any suitable form, configuration, components and operation. In this embodiment, the chin strap 130 includes a chin harness 132 configured to extend over, or fit around, the subject's chin 99 and at least one connector cable 136 associated with each end 132a, 132b of the chin harness 132 and configured to releasably connect the chin harness 132 to the headset 12.

Figure 34:
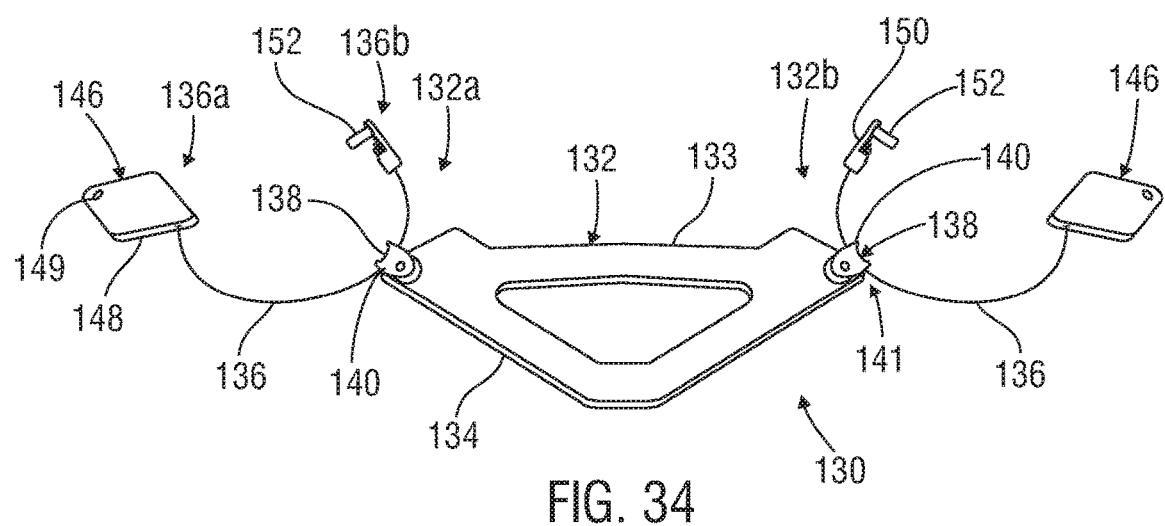
FIG. 34 is a front view of an exemplary chin strap which may be used with a headset system in accordance with any of the embodiments herein.
Figure 35:
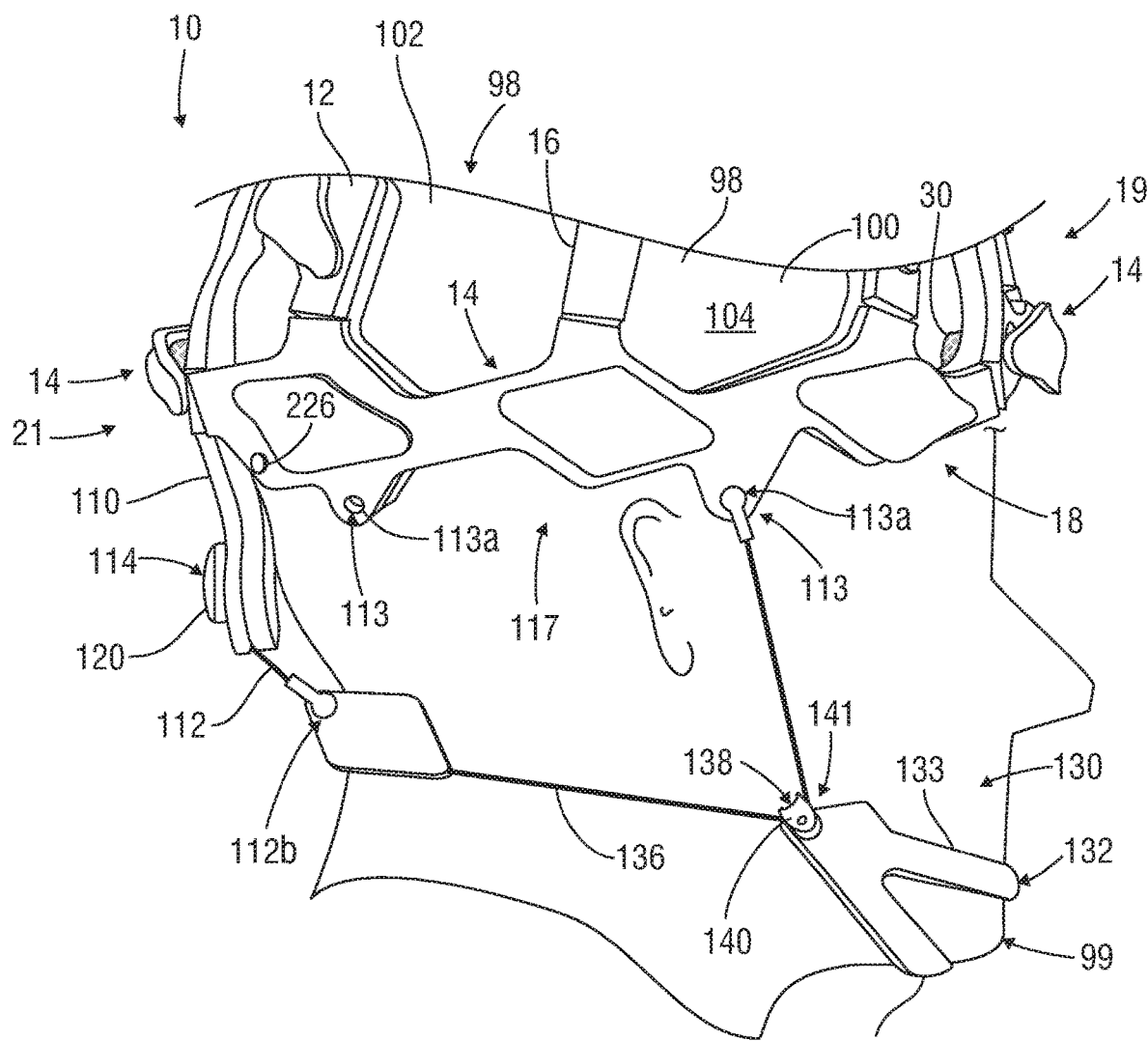
FIG. 35 is a partial side of the exemplary headset system of FIG. 27 with the exemplary chin strap of FIG. 34 coupled thereto.

Still referring to FIGS. 34-35, the chin harness 132 may have any suitable form, configuration and operation. In this embodiment, the chin harness 132 includes upper and lower straps 133, 134 configured to straddle the subject's chin 99 when the chin strap 130 is coupled to the headset 12 and fit over the subject's chin 99. In other embodiments, the chin harness 132 may include be a single strap or another component that fits over the subject's chin 99, or may include more than two straps. If desired, the chin harness 132 may be constructed of a flexible cushioned and/or soft material, such as to assist in comfortably fitting the subject's chin 99, and may have any one or more of the other potential characteristics that the exemplary strips 16 and electrode stations 14 described above (e.g. conformable, resilient, elastic, non-absorbent, water-resistant, water-proof, antimicrobial, re-usable, easy to clean and/or requires minimal cleaning, meets sanitary standards or requirements or a combination thereof). For example, the chin harness 132 may be constructed of the same or similar material as the strips 16 and/or electrode stations 14 (e.g. plastic, rubber, foam, Croslite™, silicon, Trileon™, any other type of EVA) or combination of materials.

Still referring to FIGS. 34-35, the connector cables 136 may likewise have any suitable form, configuration and operation. For example, each cable 136 may include one or more wires, ropes or other elongated components. In this embodiment, a single cable 136 (e.g. wire) extends through a connector 138 disposed at each end 132a, 132b of the chin harness 132. The illustrated connector 138 is a guide, or pulley, 140 having a passageway 141 through which the associated cable 136 extends and is freely movable back-and-forth. The exemplary guide 140 is configured and coupled to the chin harness 132 so that it will withstand substantial pulling forces during use of the chin strap 130 and headset 12. If desired, the illustrated cable 136 may be configured so it is not (at least easily) removable from the associated connector 138. In this embodiment, each end 136a, 136b of the cable 136 is equipped with a respective coupler 146, 150 that is larger than the passageway 141 of the pulley 140 and thus prevents the cable 136 from decoupling entirely from the pulley 140.

The exemplary chin strap 130 may be connectable to the headset 12 in any desired manner. In this embodiment, the coupler 146 at the first end 136a of each cable 136 is releasably engageable with one of the cables 112 extending from the exemplary tightener 114. Thus, when using the exemplary chin strap 130, instead of connecting the cables 112 to the headset 12 (e.g. at receivers 113, FIGS. 3 & 28), each cable 112 is connected to the coupler 146 of the cable 136 on the same side 116, 117 of the headset 12. The coupler 146 may have any desired form, configuration and operation. In this embodiment, the coupler 146 includes at least one pad 148. For example, the pad 148 may include at least one receiver 149 (e.g. orifice, clip, etc.) with which the post 112b (e.g. FIG. 27) of the cable 112 may be releasably secured. If desired, the pad 148 may be constructed of a flexible, cushioned and/or soft material, such as for comfort if the pad 148 contacts the subject's head 98, neck or other body part during use of the chin strap 130, and/or may have any one or more of the other potential characteristics of the exemplary strips 16 and/or electrode stations 14 as described above (e.g. resilient, elastic, non-absorbent, water-resistant, water-proof, antimicrobial, re-usable, easy to clean and/or requires minimal cleaning, meets sanitary standards or requirements or a combination thereof). For example, the pad 148 may be constructed of the same or similar material as the strips 16 and/or electrode stations 14 (e.g. plastic, rubber, foam, Croslite™, silicon, Trileon™, any other type of EVA) or combination of materials. However, the coupler 146 may instead or also include a clip, pin, mateable connector, etc.

Still referring to FIGS. 34 & 35, the coupler 150 at the second end 136b of each cable 136 is configured to releasably engage the headset 12. For example, the coupler 150 may be engageable with the headset 12 similarly as described above with respect to the cable 112. In this embodiment, since each exemplary receiver 113 on the headset 12 includes at least one hole 113a, each coupler 150 includes at least one post 152 (e.g. pin) configured to be inserted into any of the holes 113a on the same side 116, 117 of the headset 12 for engagement therewith. For another example, the coupler 150 may include a clip (e.g. similar to clip 112a of FIG. 3) or other mechanism that is releasably engageable with the any of the corresponding receivers 113 or other desired portions of the headset 12. In FIG. 35, the right side of the exemplary chin strap 130 is shown coupled between the right-side cable 112 coming of the ratcheting spool 120 and a front receiver 113 on the headset 12.

Figure 20B:
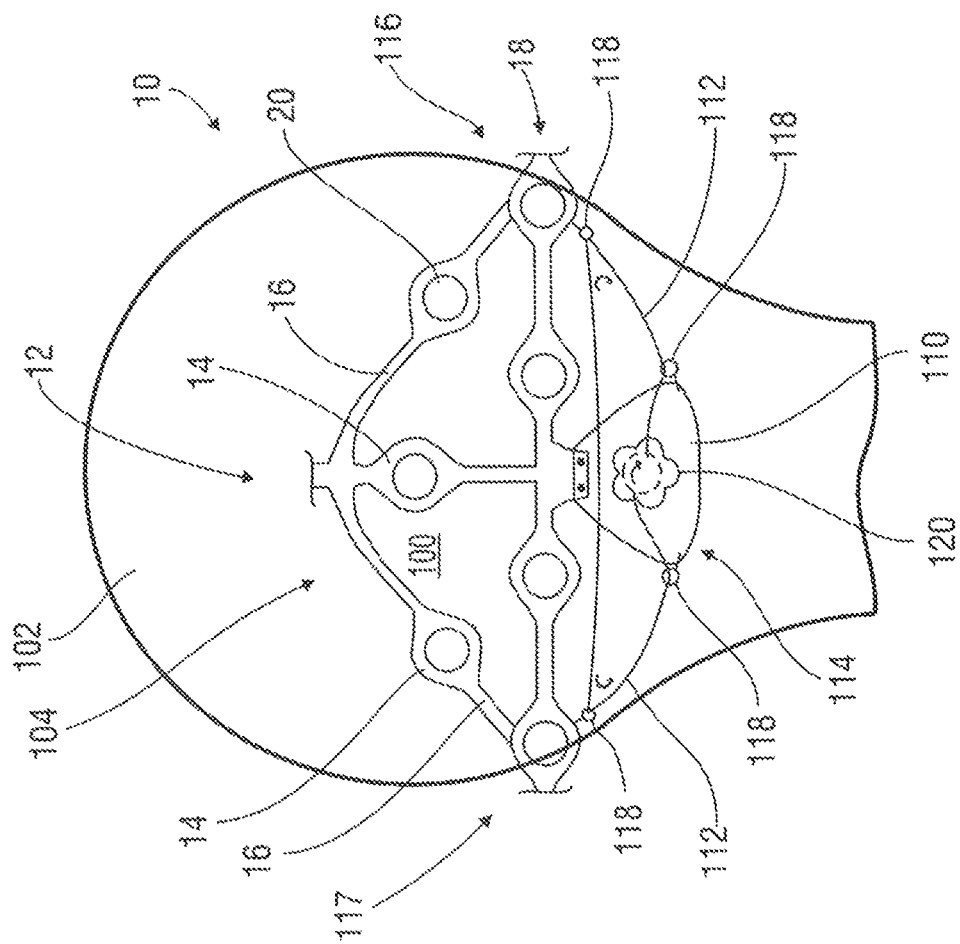
FIG. 20B is a rear view of a portion of the exemplary headset shown in FIG. 20A.
Figure 20A:
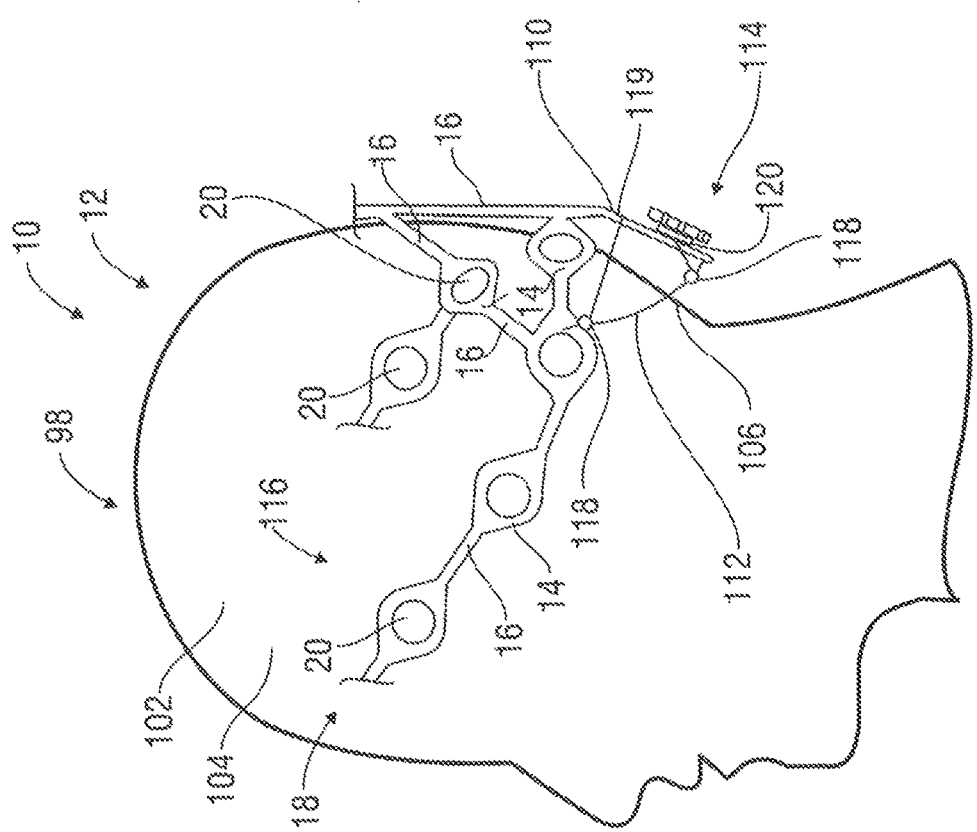
FIG. 20A is a side view of a portion of the exemplary headset system shown in FIG. 12 showing an exemplary tightener in accordance with an embodiment of the present disclosure.

In use of the illustrated chin strap 130 in combination with the exemplary tightener 114, the headset 12 is drawn down and more centered, or forward, on the subject's head 98 than embodiments of the headset 12 having only the exemplary tightener 114, or not employing a chin strap 130 or similar mechanism (e.g. FIGS. 1 & 20A-B). The exemplary chin harness 132 and subject's chin 99 therein essentially act as an anchor for tensioning the cables 136 of the chin strap 130 and the cables 112 of the tightener 114 to the headset 12.

In other embodiments, a helmet strap may be attached to each side 116, 117 of the headset 12 and releasably fastened by mating connectors. In yet other embodiments, a tightener 114 may not be included.

Referring back to FIGS. 1-3, in another independent aspect of the present disclosure, the exemplary cap 12 may have a "webbed" configuration, or arrangement, to form open spaces between some or all of its structural members (e.g. stations 14, strips 16, etc.) for any suitable purpose. For example, the strips 16 (and stations 14) may form one or more web open areas 100 to allow for visual inspection of the scalp test area 104, the position of each electrode 30 relative to the head 98 and/or the contact interface 105 (e.g. FIGS. 4-5) therebetween, to determine if the electrode 30 (or related component(s)) is making sufficient contact with the scalp test area 104 to receive useful signals from the subject's brain, any other suitable purpose or a combination thereof. As used herein, the terms "contact interface" and variations thereof means and refers to the point or area of contact between an electrode 30 or one or more components related thereto (e.g. electrode cover 50) and the scalp 102 where the electrode 30 (or related component(s)) receives signals from the subject's brain. In this illustrated embodiments (e.g. FIGS. 4-5), the exterior side surface 51 of each electrode cover 50 and each contact interface 105 are visible through the open areas 100.

For another example, the web open area 100 may assist in allowing the portions 16 of the headset 12 to bend, conform, stretch, compress, and/or fold without buckling or bulging, such as when the cap 12 is tightened or tensioned around the subject's head 98. Such flexibility of the cap 12 may, in at least some instances, allow the exemplary electrode stations 14 to be positioned substantially parallel to the scalp test area 104 and/or the electrodes 30 to be positioned substantially perpendicularly to the scalp test area 104 (e.g. FIGS. 4-5).

The web open area(s) 100 may have any suitable size, configuration and orientation. In some embodiments, for example, the web open areas 100 of the cap 12 may occupy at least approximately 20%-60% or more of the total area between the various structural members (e.g. strips 16 and stations 14) of the cap 12. In the present embodiment, the web open areas 100 occupy at least approximately 50% of the total space encompassed by the headset 12 (see also, FIGS. 12 and 17-18).

Referring back to FIGS. 4-5, the exemplary headset system 10 may have any suitable arrangement for receiving signals from the subject's brain. As indicated above, the present embodiment includes one or more wire leads 70 (e.g. EEG signal transmission wires) associated with the electrode stations 14 for receiving signals from the electrode 30 or related components (e.g. cover 50) therein and conveying the signals to a desired destination. The wire leads 70 may have any suitable form, configuration, construction and operation, and may receive the signals from the electrode 30 or related component(s) in any suitable manner and convey them to any desired destination. In this embodiment, at least one wire lead 70 is electrically coupled to an electrically-conductive surface 22 provided in each electrode aperture 20 and which conductively engages the associated electrode 30 (or associated component(s)). For example, the illustrated electrically-conductive surface 22 is slideably, electrically-conductively engaged by the exterior side surface 51 of the electrode cover 50 to receive the EEG signals therefrom.

Figure 16A:
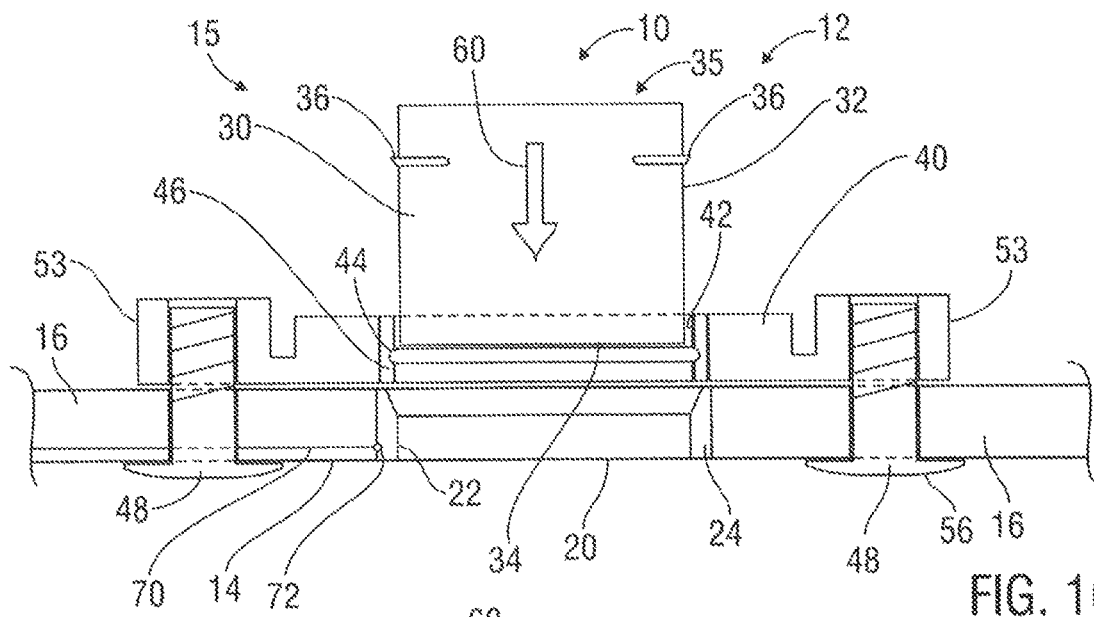
FIGS. 16A-B are side sectional views of part of the exemplary headset system of FIG. 12 showing an exemplary electrode being inserting into an exemplary electrode aperture in accordance with an embodiment of the present disclosure.
Figure 16B:
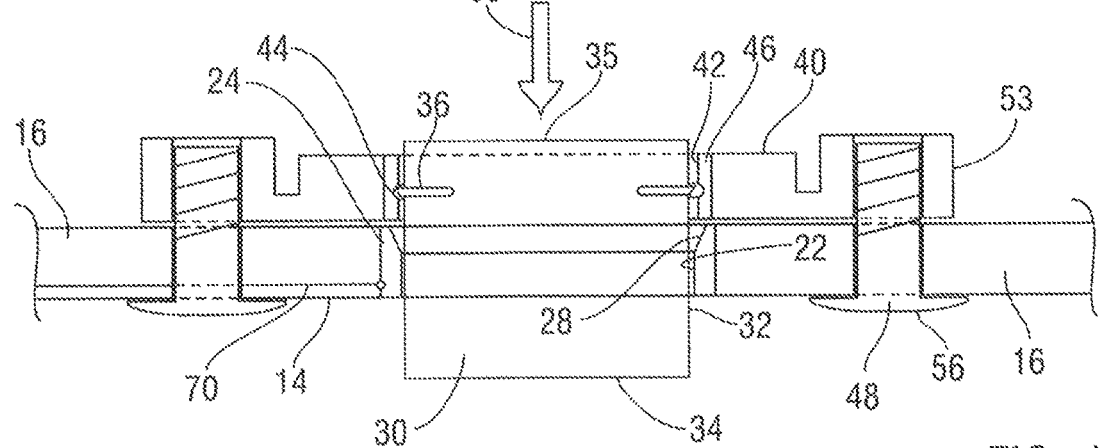
Figure 16C:
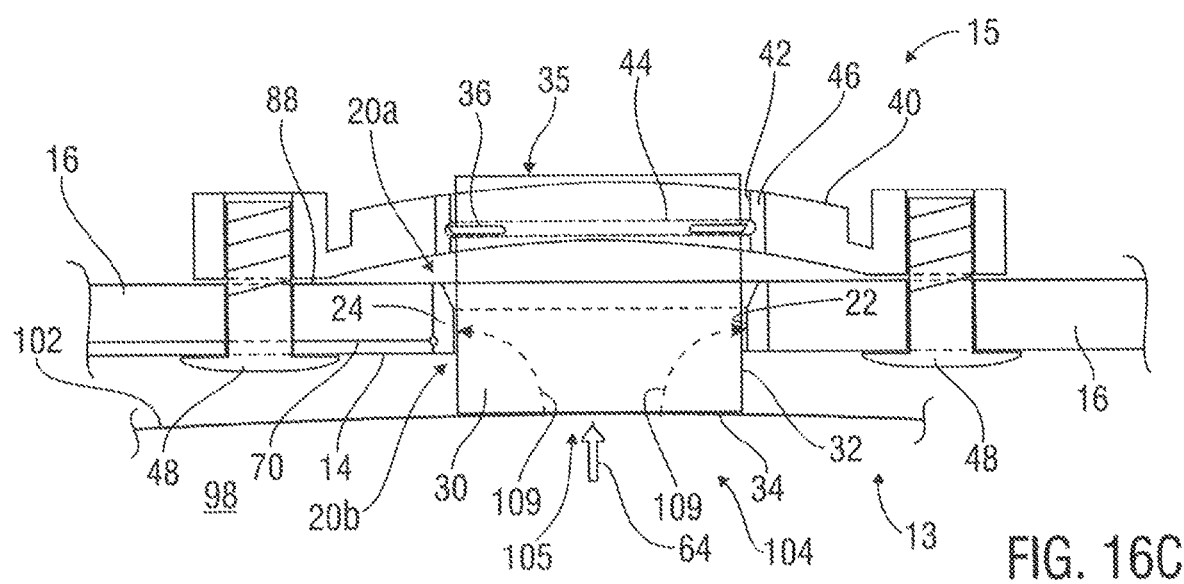
FIG. 16C is a side sectional view of the part of the exemplary headset system of FIG. 12 shown in FIGS. 16A-B showing the illustrated exemplary electrode being biased between an exemplary electrode biasing flap and a subject's head in accordance with an embodiment of the present disclosure.
Figure 17:
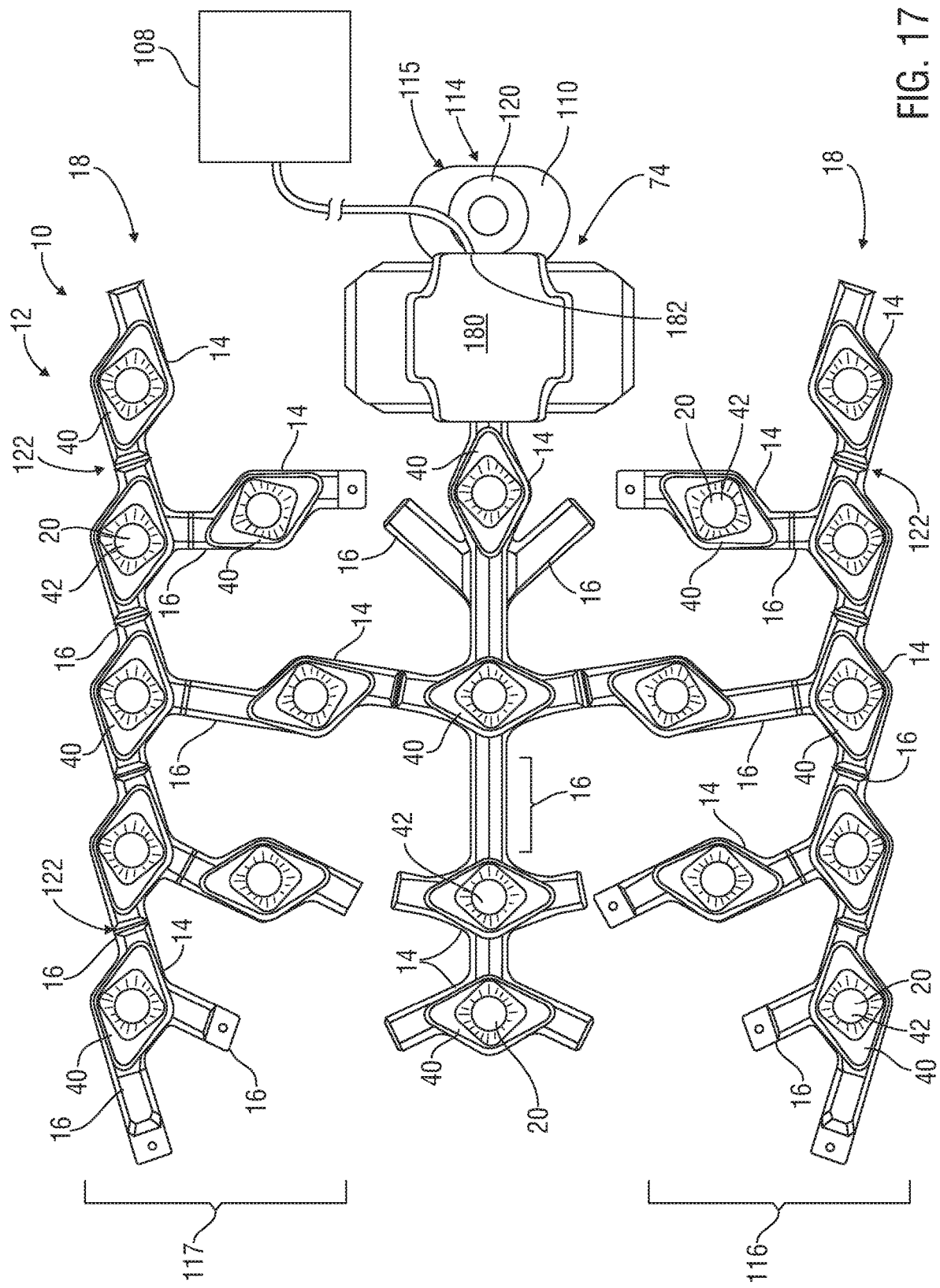
FIG. 17 is a top partially-disassembled view of the exemplary headset system shown in FIG. 12.

As shown in FIGS. 16A-17, the wire lead(s) 70 may include a station end 72 electrically coupled to the electrically-conductive surface 22 and a device end 74 electrically coupled to any suitable desired controller or measuring device(s) 108 (e.g. laptop computer, smartphone, tablet, etc.). If desired, the headset 12 may include numerous wire leads 70, which may be bundled and/or interconnected.

Referring now to FIGS. 3 & 17, the exemplary system 10 may be electrically coupled to one or more controller/measuring devices 108 in any suitable manner. For example, the illustrated system 10 includes at least one connection unit 107 for electrically coupling the wire leads 70 (e.g.

FIGS. 16A-C) to the controller/measuring device(s) 108 via an electronic processing unit (EPU) 180. In other embodiments, the connection unit 107 may directly connect the wire leads 70 to the controller/measuring device(s) 108.

Figure 32:
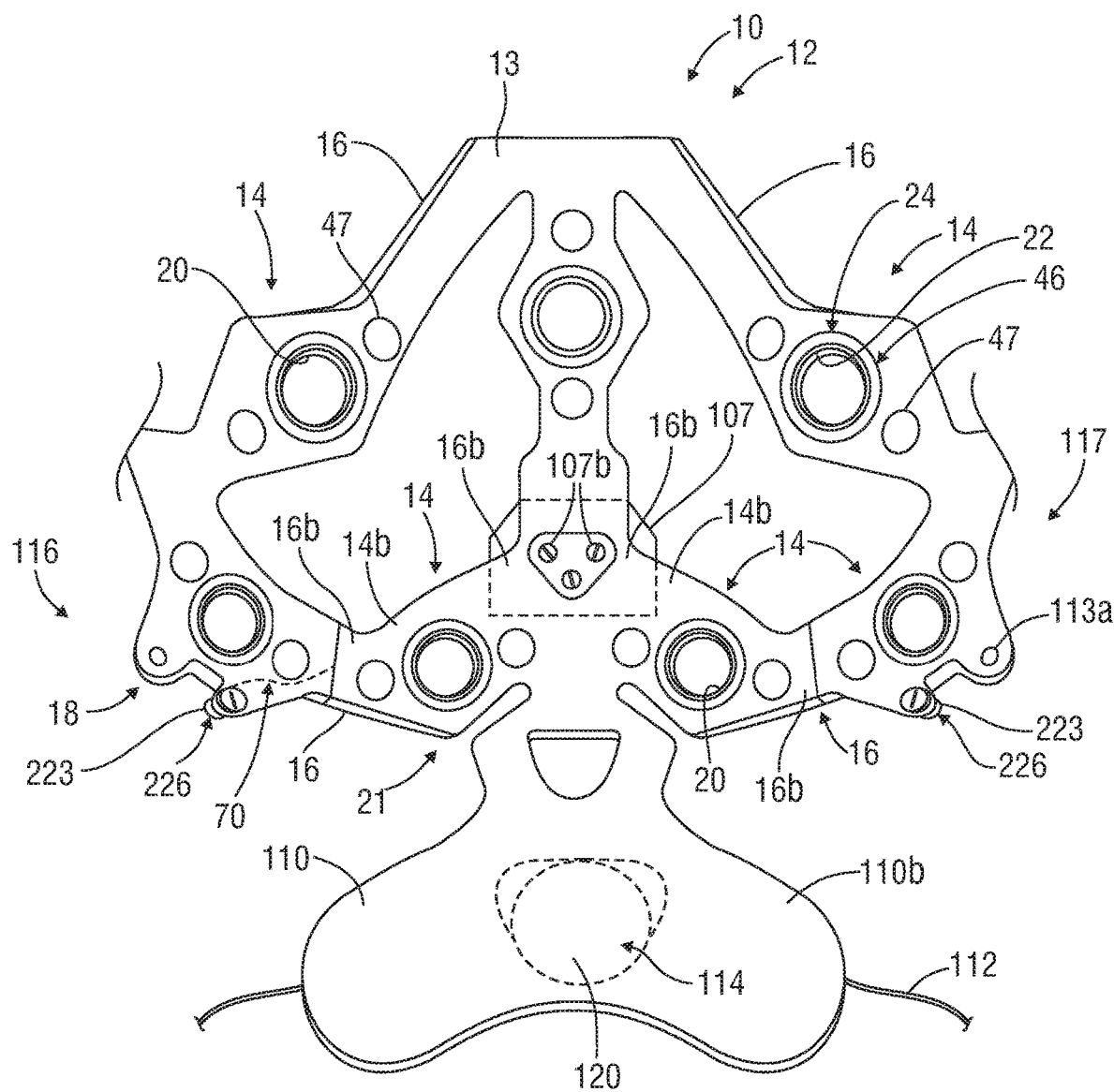
FIG. 32 is a partial front view of the inner side of the back of the exemplary headset system shown in FIG. 27.

Referring to FIGS. 30-32, the exemplary connection unit 107 may have any suitable form, configuration and operation. In the illustrated embodiments, the connection unit 107 is releasably secured to the headset 12, such as with one or more couplers 107b (e.g. bolts, FIG. 32; screws; pins; etc.). In other embodiments, the connection unit 107 may be integral to the headset 12 or secured thereto in any other manner. The exemplary connection unit 107 includes at least one mateable connector 107a for releasable electrical connection to at least one mateable connector 181 of the EPU 180. For example, the mateable connectors 107a, 181 may be mating plug and socket type electrical connectors (e.g. DVI, VGA, serial, parallel, USB, etc.). In this embodiment, the mateable connector 107a faces downwardly (see also, FIG. 27), such as to streamline the overall bulk and arrangement of the system 10, distribute the weight of the EPU 180 downwardly from the rear 21 of the headset 12, reduce the potential for disconnection of components, other desired purpose of a combination thereof. However, the mateable connector 107 may face in any other desired direction or configuration. For example, in FIG. 3, the illustrated connection unit 107 is configured so that the mateable connector 107a faces outwardly away from the rear 21 of the headset 12.

Referring now specifically to FIG. 30, the illustrated exemplary connection unit 107 also includes at least one magnet 184 having an outwardly facing magnetic pole opposite to the outwardly facing magnetic pole of at least one magnet 186 on the EPU 180 to assist in coupling the EPU 180 to the connection unit 107. The magnets 184, 186 may have any suitable form, configuration and operation. In this embodiment, two round, similar-poled, magnets 184 are provided on the connection unit 107 proximate to the mateable connector 107a and one elongated magnet 186 of the opposite magnetic pole is provided proximate to the mateable connection 181 of the EPU 180. However, any other configuration may be used. The magnetic engagement of the EPU 180 and headset 12 may be provided for any desired purpose. In this embodiment, the magnetic attraction of the magnets 184, 186 secures the EPU 180 to the headset 12 in the desired position. For another example, the magnetic engagement may provide an easy, simple and reliable break-away connection of these components. For example, if something unintentionally contacts the EPU 180 or connection unit 107, the magnets 184, 186 may disengage (e.g. break away from one another) without causing any damage to any components. For other examples, the magnetic connection of the EPU 180 to the headset 12 can be simple, unlikely to become damaged when disconnected or over multiple uses, easy and cost-effective to manufacture, made with few components, configured with a magnetic strength to provide a desired and sufficiently strong connection, or a combination thereof. For yet another example, a non-magnetic connection (e.g. mechanical) of the EPU 180 to the headset 12 could include more components which can malfunction, be more complex and/or more costly to manufacture, be more likely to become subject to wear, breakage and/or damage when disconnected and/or over multiple uses, or a combination thereof. For yet another example, the connection and disconnection of the magnets 184, 186 may remove mechanical stress placed upon, and reduce wear-and-tear to, the mateable connectors 107a, 181 of the connection unit 107 and EPU 180 and preserve them from potential damage during use, connection and (intended or accidental) disconnection thereof.

Figure 33:
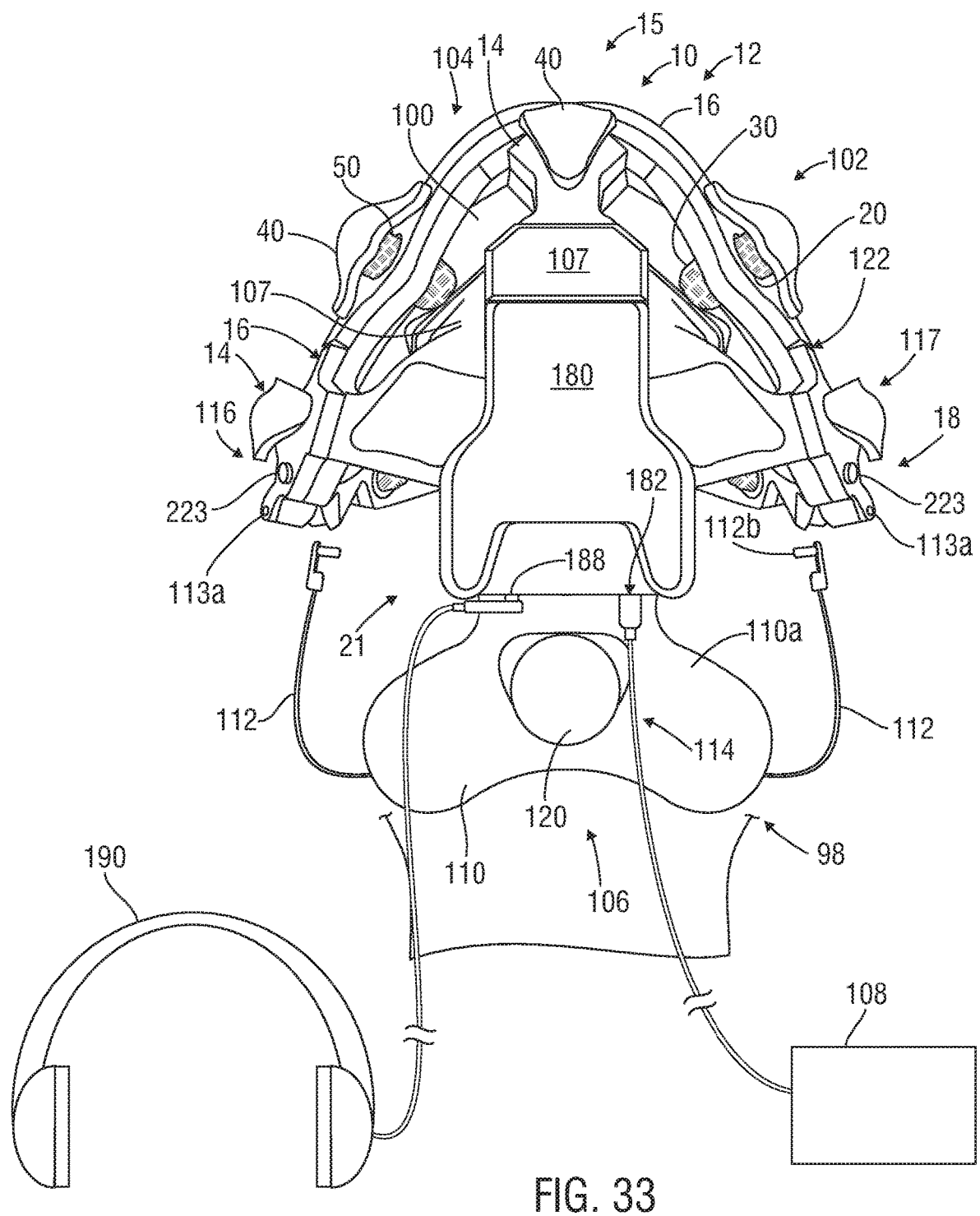
FIG. 33 is a rear view of the exemplary headset system of FIG. 27 shown with the exemplary EPU of FIG. 30 and various other exemplary external devices coupled thereto in accordance with an embodiment of the present disclosure.

Referring now to FIGS. 17 & 33, in the illustrated embodiments, the EPU 180 contains hardware (e.g. printed circuit boards ("PCB")) and/or software (e.g. proprietary firmware of patentee WAVi Co.) useful for conducting tests with the headset 12 and related devices, receiving, collecting, analyzing organizing, merging, compiling or transmitting data, any other capabilities or any combination thereof. The exemplary EPU 180 includes one or more connectors, or connector ports, 182 (e.g. DVI, VGA, serial, parallel, USB, etc.) for releasable engagement with the controller/measuring device(s) 108 (e.g. for exchanging data therewith, receiving power therefrom, etc.). If desired, the EPU 180 may include one or more additional connectors, or connection ports, for engagement with one or more other related or external components. For example, referring to FIGS. 31A-B & 33, the exemplary EPU 180 includes at least one port, or socket, 188 for connecting headphones, or earphones, 190 (e.g. useful for conducting one or more brain wave measurement tests or other tests (e.g. audio response testing)) to the EPU 180, one or more ports, or sockets, 192 for receiving electrical signals from one or more monitors, or devices, coupled to the subject's body (e.g. ECG monitor (e.g. EEG chest strap)), one or more ports, or sockets, 194 for connection with one or more ear-clip assemblies 200 (e.g. described below; see e.g. FIG. 40) or any other devices. Any of the above or other desired connections to the EPU 180 may utilize or include a releasable magnetic connection (e.g. similarly as described above with respect to the connections of the EPU 180 and the connection unit 107 and/or as described below with respect to one or more ear-clip assemblies 200 and with any of the same benefits).

Referring back to the embodiment of FIGS. 4-5, the electrically-conductive surface 22 may have any suitable form, configuration and operation. In some embodiments, the electrically-conductive surface 22 may be provided on a metal tab or other configuration that at least partially lines an interior arc or portion of the aperture 20. In the illustrated embodiment, the electrically-conductive surface 22 is provided on an electrically-conductive ring 24 disposed in, or lining, the electrode aperture 20.

When included, the electrically-conductive ring 24 may have any suitable form, configuration and operation. For example, the illustrated ring 24 is rigid and includes first and second ring portions 24a, 24b which are snapped or friction-fit, and/or glued together. Further, the electrically-conductive ring 24 may have any desired construction as long as it allows the transmission of signals from an electrode 30 or related component(s) to at least one wire lead 70. In this embodiment, the ring 24 is constructed of tin, such as to provide sufficient electrical conductivity with low electrical noise, to minimally tarnish and/or other suitable purpose(s). In other embodiments, the electrically-conductive ring 24 may be made of any other suitable metal, such as gold, silver, copper, or aluminum, or a carbon composite. In some embodiments, the electrically-conductive ring 24 may include a metal plating or surfacing. In various embodiments, the electrically-conductive ring 24 may be constructed of a combination of the aforementioned or other materials.

Figure 9:
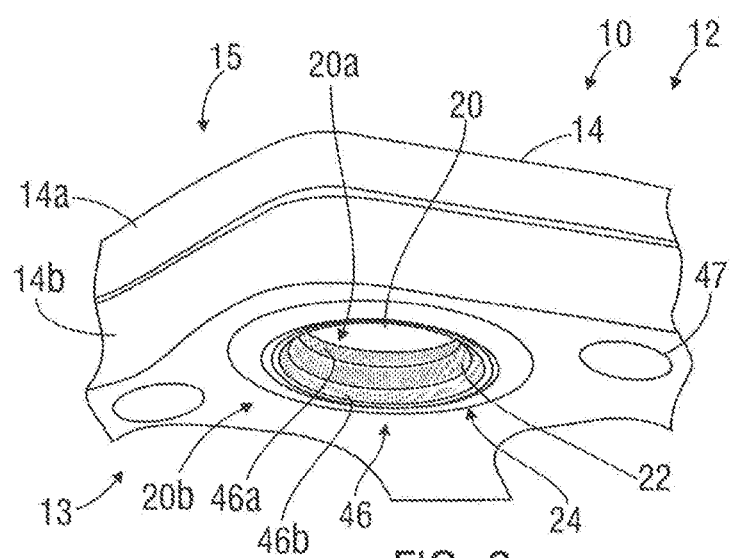
FIG. 9 is a perspective view of part of the exemplary headset system of FIG. 1 showing an exemplary electrode aperture.

It should be noted that the electrically-conductive ring 24 may serve one or more additional purposes. For example, the electrically-conductive ring 24 may also serve as an electrode retention ring (46) for assisting in positioning the associated electrode 30, such as will be described further below (e.g., FIGS. 4-5 and FIG. 9).

Still referring to the embodiment of FIGS. 4-5, the wire lead(s) 70 may conductively engage the electrically-conductive surface 22 in any suitable manner. In this particular configuration, the illustrated wire lead 70 is coupled to the electrically-conductive ring 24 via an electrically-conductive screw 71. However, the wire lead 70 could instead be soldered or coupled to the ring 24 in any other suitable manner, as desired.

Figure 13:
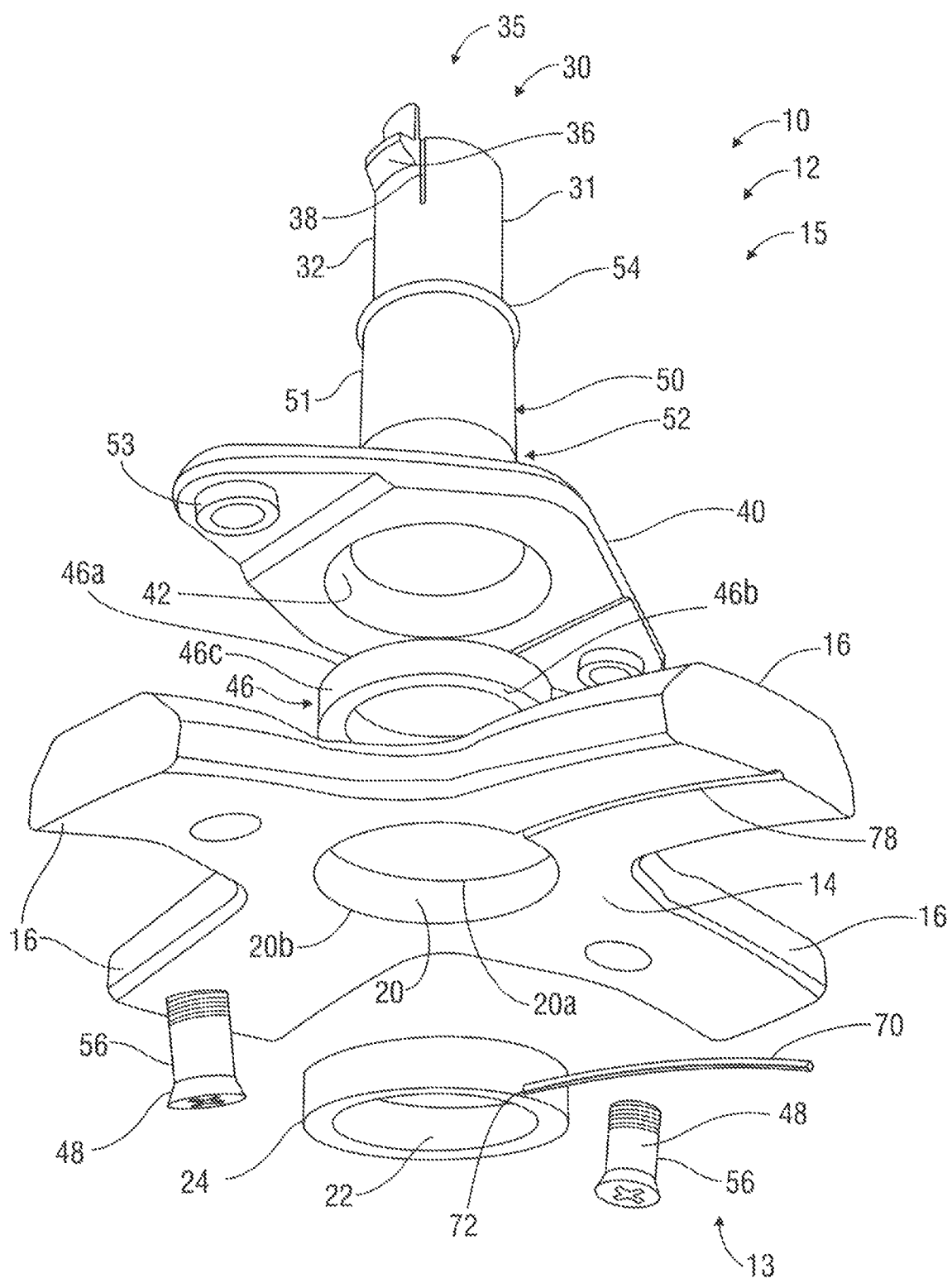
FIG. 13 is an exploded assembly view of part of the exemplary headset system of FIG. 12 showing an exemplary electrode station and related components.

The wire leads 70 may be positioned in or carried by the headset 12 in any suitable manner. In this embodiment, each wire lead 70 is at least partially or substantially hidden or sandwiched between the respective upper and lower layers 14*a*, 14*b* of the electrode stations 14 and the respective upper and lower layers 16*a*, 16*b* of the strips 16. In other embodiments, such as shown in FIG. 13, the wire leads 70 may lie in a series of recessed wire channels 78 formed in the inner side 13 of the cap 12. In yet other embodiments, the wire leads 70 may be carried internally within the stations 14 and strips 16 or otherwise coupled to the cap 12. In yet other embodiments, a wire harness including all the wire leads 70 may be enclosed within the cap 12 or affixed thereto.

In another independent aspect of the present disclosure, referring back to FIGS. 1-5, the electrodes 30 are biased into contact with the subject's head 98 sufficient to receive signals from the subject's brain in any suitable manner. In this embodiment, each electrode 30 is configured to be suspended within its associated electrode aperture 20 so that it effectively floats within a generally defined range of up-and-down motion relative to the aperture 20. At the same time, the exemplary biasing flap 40 provides downward biasing forces on the electrode 30.

During use, each illustrated biasing flap 40 independently places downward biasing forces on its associated electrode 30, while concurrently, the subject's head 98 typically places upward forces (e.g. arrow 64, FIGS. 5, 16C and 19C) on the electrode 30. As each individual exemplary electrode 30 freely floats (e.g. within a range-of-motion) relative to its associated aperture 20, the electrode 30 will automatically move into the appropriate up-and-down position between the biasing flap 40 and the subject's head 98 and relative to the headset 12 independent of all the other electrodes 30 in the headset 12. The position of each illustrated electrode 30 with thus be influenced or determined by the shape of the subject's head 98 at that location. Different electrodes 30 may assume different positions relative to the headset 12. Accordingly, since each exemplary electrode 30 fits the shape of the subject's head 98 at that location, the headset 12 may conform to the unique (typically uneven) shape of each subject's head 98. As compared to prior signal receiving headsets, the exemplary cap 12 may, for example, be more universally fittable and useful, more easily adaptable to the unique shape of different subjects' heads 98, provide better electrode positioning and electrical contact with the subjects' scalp test areas 104, be easier and quicker to successfully use, be more reliable or a combination thereof.

Referring again FIGS. 4-5, in many embodiments, the electrodes 30 may be moveable and positionable relative to the headset 12 between at least one retracted position (or range-of-motion) and at least one extended position (or range-of-motion) to assist in conforming the headset 12 to the shape of each subject's head 98, provide better electrode positioning and electrical contact with the subjects' scalp test areas 104, be easier and quicker to successfully use, be more reliable, any other desired purpose or a combination thereof. It should be noted that during use of this embodiment, in all retracted and extended positions the electrode 30 is biased in the direction of the subject's head 98 by its associated biasing flap 40.

In a retracted position, each exemplary electrode 30 is higher in its associated electrode aperture 20, and the bottom end 34 of the electrode 30 is closer to the inner side 13 of the headset 12, than in its extended position(s). In other words, in a retracted position, more of the illustrated electrode 30 lies above the electrode aperture 20 than in an extended position. The exemplary retracted position(s) may be useful, for example, as the initial position of the electrodes 30 during placement of the cap 12 on the subject's head. In many instances, the retracted position(s) of some, many or all the electrodes 30 may provide sufficient electrical conductivity with the subject's head 98, so that movement into an extended position may not be necessary.

Still referring to FIGS. 3 and 4, an extended position, more of the exemplary electrode 30 sits below the aperture 20 than above the aperture 20. The extended position(s) may be desirable or necessary, for example, for any electrodes 30 not making sufficient electrical contact with the scalp test area 104 after the cap 12 is fitted onto the subject's head 98.

The electrodes 30 may be moveable between retracted and extended positions in any desired manner. For example, to move an exemplary electrode 30 from a retracted position to an extended position, the flap 40 and electrode 30 may be pushed downwardly from above. To move the illustrated electrode 30 from an extended position to a retracted position, the bottom end 34 of the electrode 30 may be pushed upwardly. (See also, FIGS. 18-19C).

Figure 10A:
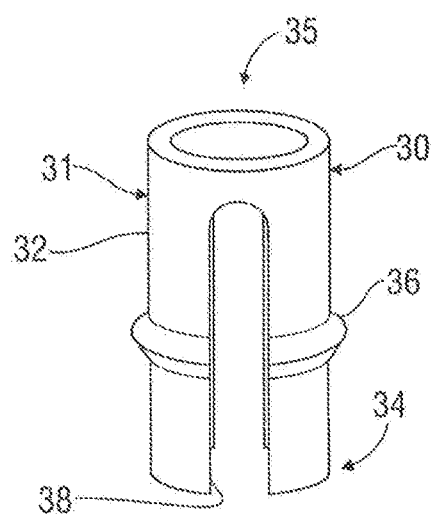
FIG. 10A is a perspective view of the exemplary electrode useful in the exemplary headset system shown in FIG. 1 in accordance with an embodiment of the present disclosure.
Figure 10B:
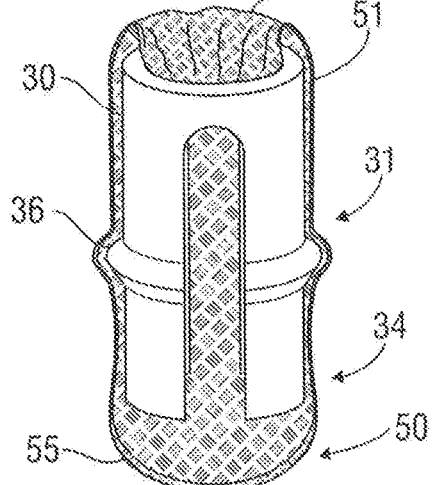
FIG. 10B is a perspective view of the exemplary electrode shown in FIG. 10A with an exemplary electrode cover shown in partial cross-section in accordance with an embodiment of the present disclosure.
Figure 10C:
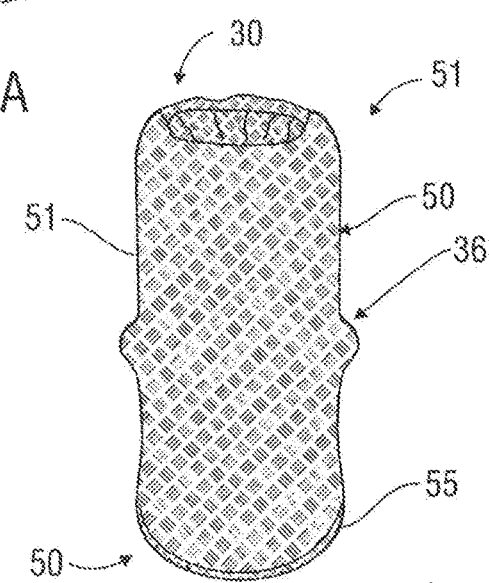
FIG. 10C is a perspective view of the exemplary electrode of FIG. 10B shown encapsulated by the exemplary illustrated electrode cover.

Now referring to FIGS. 10A-C, in some embodiments, the electrode 30 includes one or more protrusions 36 extending outwardly from at least one side 31 thereof. The protrusion(s) 36 (e.g. FIGS. 4-5) may be useful, for example, to assist in selectively positioning the electrode 30 relative to the headset 12 and/or subject's scalp 102 (e.g. height-wise and angle-wise (e.g. to conform substantially perpendicularly to the scalp 102)), provide more flexibility and greater degrees of freedom in the up-and-down movement of the electrode 30, assist in the movement of the electrode 30 between retracted and extended positions, secure the electrode 30 into one or more retracted or extended positions, provide a distinct range-of-motion of the electrode 30 in multiple respective retracted and extended positions, any other suitable purpose or a combination thereof.

The protrusions 36 may have any suitable form, configuration and construction. For example, one or multiple adjacent protrusion(s) 36 may extend partially or entirely around the outer side surface 32 of the electrode 30. In this embodiment, two aligned protrusions 36 form a circular ridge around the outer side surface 32 of the cylindrically-shaped electrode 30 at a desired height on the electrode 30. For example, the protrusion 36 may be spaced upwardly from the bottom end 34 of the electrode 30 by approximately ⅓ of the height of the electrode 30 to achieve the desired result(s) of use of the protrusion 36, such as described above. For some other examples, the protrusions 36 may be or include one or more rims, ledges, shelfs, cut-outs, uneven portions, buttons, hooks, pimples, channels or other-shaped members or portions extending at least partially around the side(s) 31 of the electrode 30. Further, when electrode covers 50 are included, the system 10 may be configured so that the covers 50 conform to the shape of the protrusion(s) 36 of the associated electrodes 30 (e.g. FIGS. 10B-C). In other embodiments, if desired, the protrusion 36 may penetrate through the electrode cover 50.

The protrusions 36 may have any suitable operation. Referring again to FIGS. 4-5, in this embodiment, when an electrode 30 is in a retracted position, the protrusion 36 will be closer to the outer side 15 of the headset 12 than the inner side 13. When the exemplary electrode 30 is in an extended position, the protrusion 36 will be closer to the inner side 13 of the headset 12 than the outer side 15.

If desired, the protrusion 36 may be useful to establish and/or secure the desired position of the electrode, such as in the extended and/or retracted positions. For example, the protrusion 36 may be engageable with the electrode aperture 20, or other component(s), in one or more positions. In some embodiments, the protrusion 36 may be configured to releasably selectively engage the upper edge 20a of the aperture 20 and/or the lower edge 20b of the aperture 20 (see also, FIGS. 13, 19B), one or more grooves 44 (e.g. FIGS. 16B-C) or other protrusion-engagement surface(s) provided in the aperture 20 or other component (e.g. upper and lower edges 46a, 46b of an electrode retention ring 46 (see also, FIG. 19B)), or a combination thereof.

In the embodiment of FIGS. 16A-C, the protrusion 36 is selectively, releasably engageable with a groove, or catch, 44 provided in the flap hole 42 of the biasing flap 40. In this example, the electrode 30 is insertable downwardly (arrow 60, FIGS. 16A-B) into the illustrated flap hole 42 to snap the protrusion 36 into releasable engagement with the illustrated groove 44. In this position, the exemplary electrode 30 is effectively anchored to the flap 40. As the illustrated flap 40 flexes, the electrode 30 moves, or floats up and down in and relative to the electrode aperture 20 in response to upward forces from the subject's scalp 102 during use (e.g. arrow 64, FIG. 16C).

In this embodiment, the electrode 30 is thus movable into only one engaged position, and the exemplary flap 40 serves the dual-purpose of biasing and retaining the electrode 30. However, in other embodiments, additional engaged positions may be provided, such as with multiple grooves 44 or other engagement surfaces in the flap hole 42 or other component. The use of one or more grooves 44 or other protrusion engagement surface(s) may be useful to selectively positioning the electrode 30 relative to the headset 12 and/or subject's scalp 102 (e.g. height-wise and angle-wise (e.g. to conform substantially perpendicularly to the scalp 102)), provide a distinct range-of-motion of the electrode 30 relative to the headset 12, any other suitable purpose or a combination thereof.

Figure 26A:
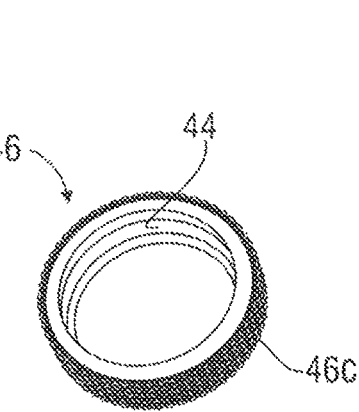
FIG. 26A is a perspective view of an exemplary electrode retention ring useful in various embodiments of headset systems in accordance with one or more embodiments of the present disclosure.
Figure 26B:
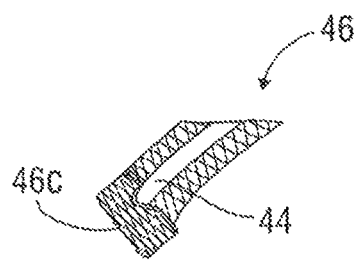
FIG. 26B is a perspective view of part of the exemplary electrode retention ring shown in FIG. 26A.

Still referring to FIGS. 16A-C, if desired, the groove 44 or other protrusion engagement surface of the flap hole 42 may be formed in an electrode retention ring 46 disposed within, or lining, the flap hole 42. The retention ring 46 may have any suitable form, configuration and operation. In this embodiment, for example, the retention ring 46 is rigid, constructed of plastic, molded into the flap 40 and includes a textured outer surface 46c (e.g. FIGS. 26A-B) for gripping the flap hole 42 to secure them together.

In some embodiments, the groove, or catch, 44 may be configured (e.g. with one or more angled edges or may be polarized) to assist in selectively positioning the electrode 30 relative to the headset 12 and/or subject's scalp 102 (e.g. height-wise and angle-wise (e.g. to conform substantially perpendicularly to the scalp 102)), promote movement of the electrode 30 in a desired direction for removal (such as downwardly) or other purpose. In this example, once the electrode 30 is inserted and snapped into the groove 44 from above (from the outer side 15 of the headset 12), the electrode 30 may be easily, or only, removed by pushing downwardly on the electrode 30 to release it from the groove 44, flap hole 42 and electrode aperture 20. In other embodiments, the groove, or catch, 44 may be configured to promote or require (i) upward insertion and removal of the electrode 30 from underneath (from the inner side 13 of the headset 12), (ii) upward insertion and downward removal, (iii) downward insertion and upward removal, or (iv) unidirectional insertion and removal.

Referring back to the embodiment of FIGS. 4-5, in this example, the illustrated electrically-conductive ring 24 also serves as the electrode retention ring 46 and does not include a groove 44. In this example, the relationship of the illustrated electrode protrusion 36 relative to the electrode retention ring 46 determines whether the electrode is in a retracted or extended position. For example, the protrusion 36 may be shaped and sized so that it sits above the electrode retention ring 46 (closer to the upper edge 46a of the ring 46 than the lower edge 46b) when the electrode 30 is in a retracted position, and below the electrode retention ring 46 (closer to the lower edge 46b of the ring 46 than the upper edge 46a) when the electrode 30 is in an extended position. From either position, with sufficient pressure on the exemplary electrode 30, the protrusion 36 is moveable between a retracted position and an extended position. Thus, the illustrated protrusion 36 is forcibly, selectively, slideable up and down through the retention ring 46. For example, the protrusion 36 may be designed to be movable through the ring 46 under only certain applied pressure. For example, when the protrusion is below the retention ring 46 (the electrode 30 in an extended position), the system 10 may be designed so that the typical or expected upward forces from the subject's head 98 during fitting and use of the headset 12 will not dislodge the protrusion 36 upwardly through the ring 46.

Still referring to FIGS. 4-5, in some embodiments, the protrusion 36 and/or the upper and/or lower edges 46a, 46b of the electrode retention ring 46 may be shaped to complement each other, such as to assist in selectively positioning the electrode 30 relative to the headset 12 and/or subject's scalp 102 (e.g. height-wise and angle-wise (e.g. to conform substantially perpendicularly to the scalp 102)), assist in the desired direction of insertion/removal of the electrode 30 into/from the headset 12, other suitable purpose or a combination thereof. For example, the outer curvature of the protrusion 36 (e.g. FIG. 10A), may match the curvature of the edges 46a, 46b (e.g. FIG. 9) of the ring 46 so that the protrusion will seat in the upper and lower edges 46a, 46b in respective retracted and extended positions. In the illustrated embodiment, the upper and/or lower edges 46a, 46b of the electrode retention ring 46 are beveled (e.g. FIG. 9) to compliment the shape of the protrusion(s) 36.

Also if desired, the movement of the protrusion 36 above or below the electrode retention ring 46 may provide additional positions for the electrode 30. In the present embodiment, the electrode 30 can freely move within a defined up and down range-of-motion above the electrode retention ring 46 among multiple retracted positions and below the electrode retention ring 46 among multiple extended positions.

Figure 19A:
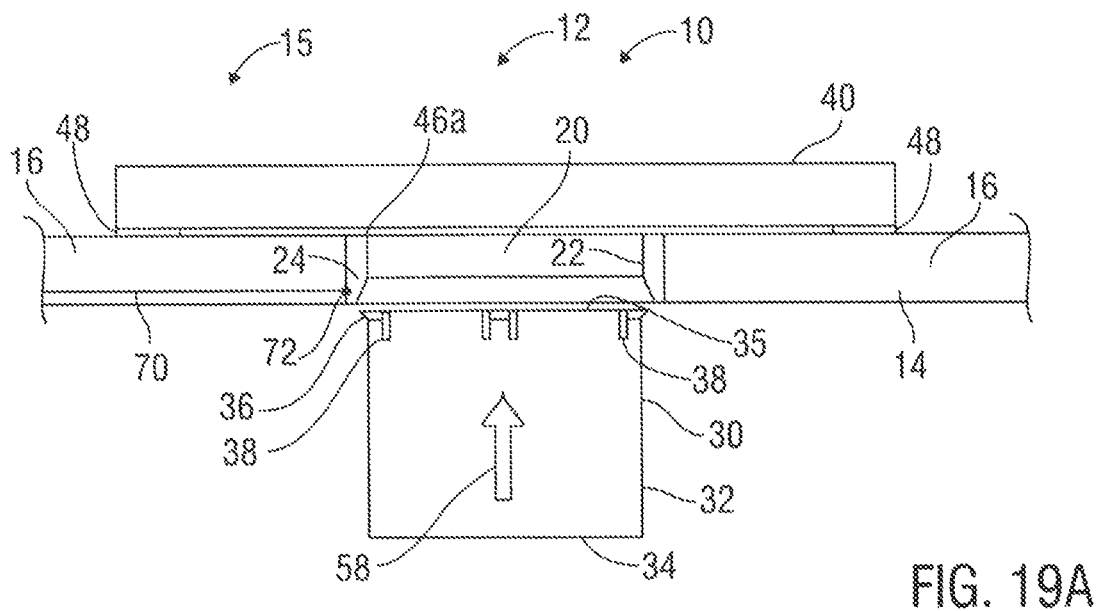
FIGS. 19A-B are side sectional views of part of the exemplary headset system of FIG. 18 showing an exemplary electrode being inserting into an exemplary electrode aperture in accordance with an embodiment of the present disclosure.
Figure 19B:
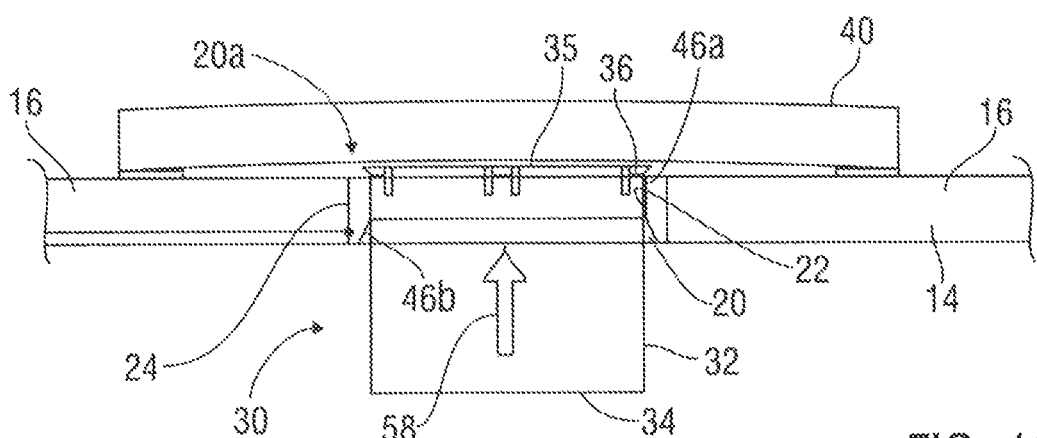
Figure 19C:
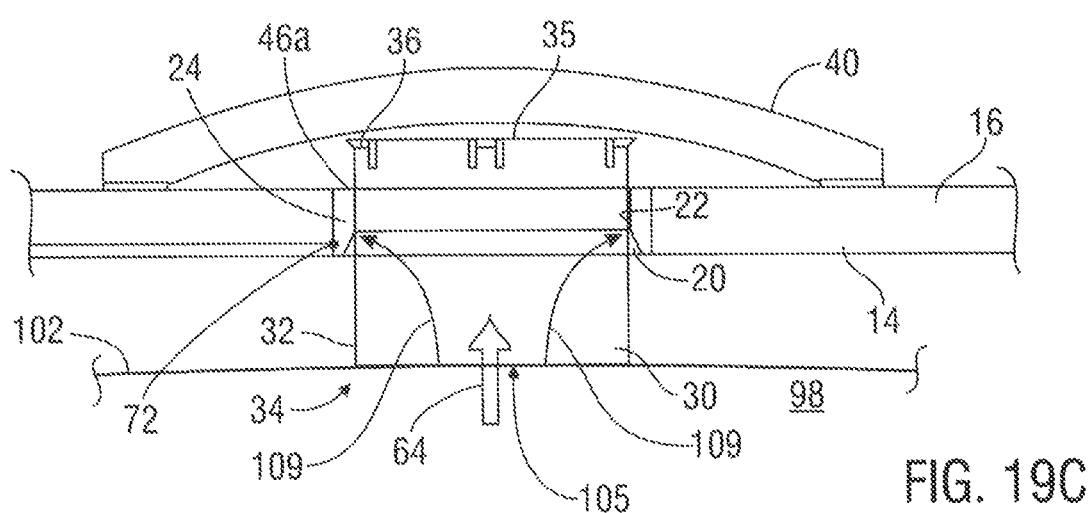
FIG. 19C is a side sectional view of the part of the exemplary headset system of FIG. 18 shown in FIGS. 19A-B showing the illustrated exemplary electrode being biased between an exemplary electrode biasing flap and a subject's head in accordance with an embodiment of the present disclosure.

In the embodiment FIGS. 19A-C, the protrusion 36 is located proximate to the top end 35 of the electrode 30 and releasably engageable with the upper edge 46a of the retention ring 46 into and out of one extended position. In this embodiment, the electrode 30 is moveable within a defied range-of-motion in multiple extended positions (above the electrode aperture 20) due to the upward forces (arrow 64, FIG. 19C) placed upon it by the subject's head 98.

Figure 21A:
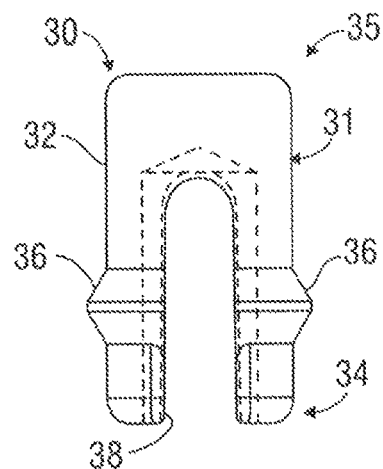
FIG. 21A is a side view of the exemplary electrode shown in FIG. 10A.
Figure 21B:
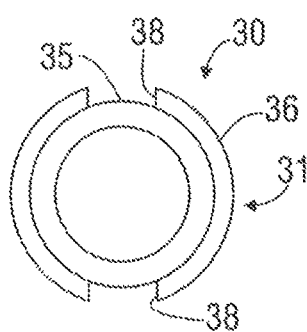
FIG. 21B is a top view of the exemplary electrode of FIG. 21A.
Figure 23:
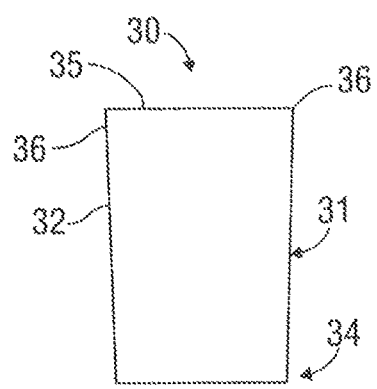
FIG. 23 is a side view of an exemplary electrode in accordance with another embodiment of the present disclosure.

Referring now to FIGS. 21A-B, the electrodes 30 may have any suitable form, configuration, components and operation. The electrode 30 may be a single unitary component or multiple interconnected units. For example, in the exemplary embodiment, the electrode 30 is a single unit having a generally cylindrical outer shape. Some other exemplary outer shapes of electrodes 30 are square, triangular, oval, stepped and rectangular. In FIG. 23, the exemplary electrode 30 has an upwardly-angled, or flared, outer shape, such as for ease or insertion from above into the flap hole 42 and/or electrode aperture 20. In other embodiments, the electrode 30 may have a downwardly-angled, or flared outer shape, such as for ease or insertion from below into the electrode aperture 20 and/or flap hole 42.

In some embodiments, the electrode 30 is at partially formed of memory foam (e.g. FIG. 23). Memory foam electrodes 30 may have any desired form, configuration and operation. For example, memory foam electrodes 30 may be useful at certain location on the head 98, such as portions with no hear (e.g. the forehead or on the entire head 98 of a bald subject).

In some embodiments, some or all of the electrodes 30 may be configured to be useful without electrode covers 50. For example, the bottom end 34 of the electrode 30 may be electrically conductive to the outer side surface 32 thereof. In such embodiments, the bottom end 34 may electrically conductively contact the scalp 102 and receive signals from the subject's brain. Those signals may then be electrically communicated to the outer side surface 32 of the electrode 30, then to the electrically-conductive surface 22 in the electrode aperture 20, and then to the wire lead 70.

Still referring to FIGS. 21A-B, the electrode 30 may be constructed of any suitable material, such as plastic, rubber, paper, fiberglass, wood, material tolerant of one or more conductive solutions, carbon-containing material, or a combination thereof. In some embodiment, the electrodes 30 are constructed of fluid absorbing material, such as foam and/or electrically-conductive material, such as conductive polymer material.

Figure 22:
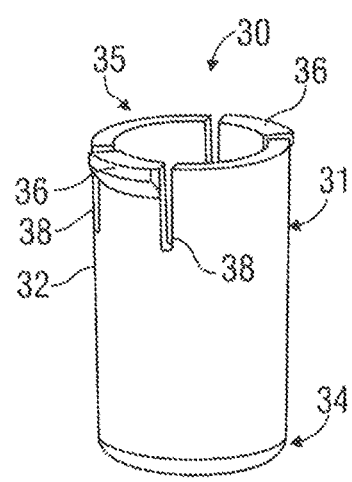
FIG. 22 is a perspective view of an exemplary electrode in accordance with another embodiment of the present disclosure.

In various embodiments, the top and/or bottom ends 35, 34 of the electrode 30 may be open, include one or more perforations or be closed. In the present embodiment, both the top end 35 and bottom end 34 are open. In the embodiment of FIGS. 13 and 22, the top end 35 of the electrode 30 is open, while the bottom end 34 is at least substantially closed (e.g. may include one or more perforations for engagement with an internally-located flexible electrode stabilizing insert). In some embodiments, the bottom end 34 of the electrode 30 may be textured or rough, such as to improve contact and electrical conductivity with the scalp 102, be rubbed against the scalp 102 to exfoliate the skin to assist in attaining good electrical conductivity, other suitable purpose or a combination thereof.

Figure 14:
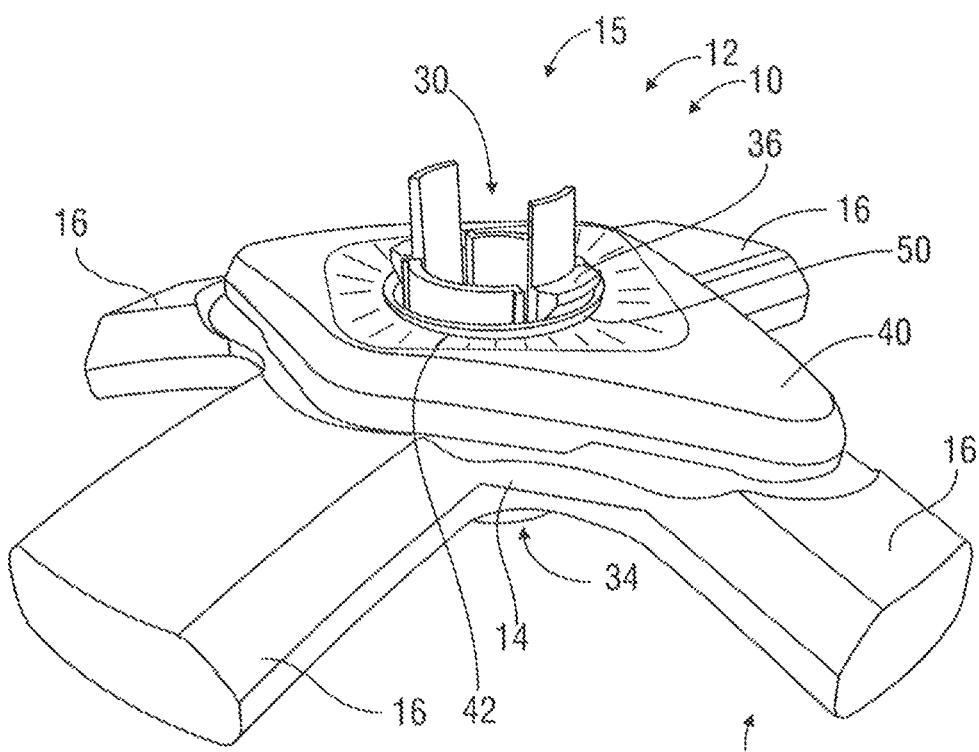
FIG. 14 is a perspective view of the exemplary electrode station and related components of FIG. 13.
Figure 15:
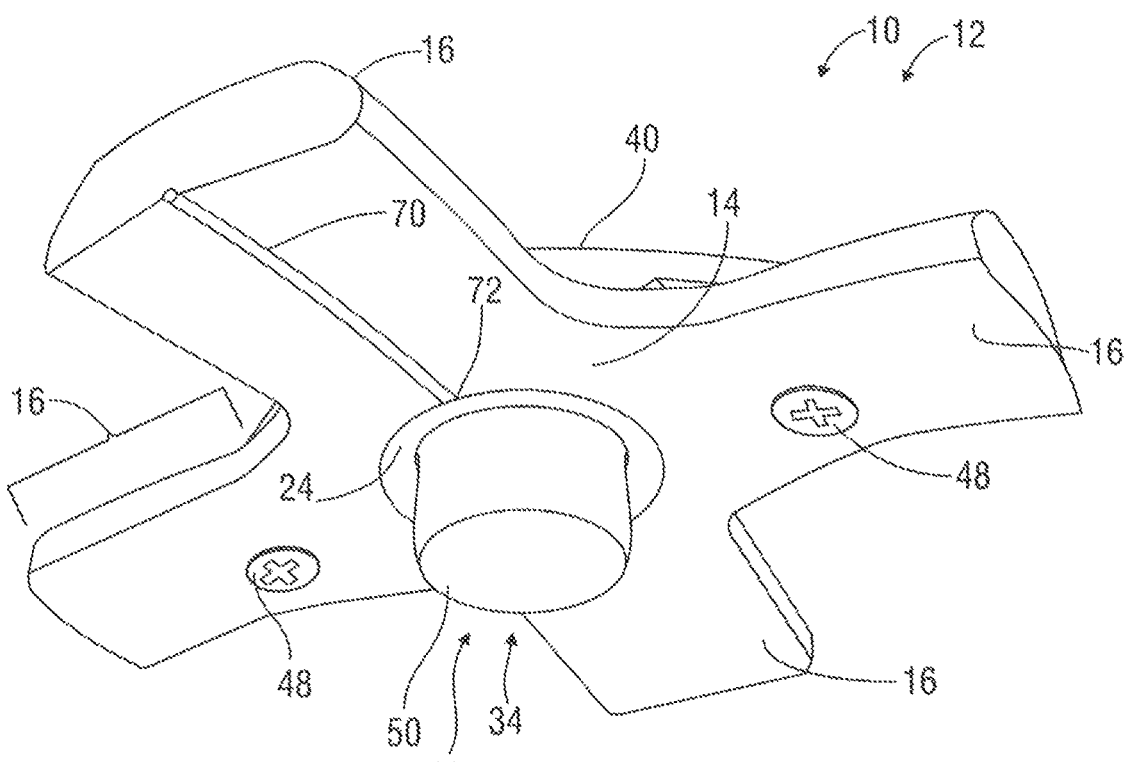
FIG. 15 is another perspective view of the exemplary electrode station and related components of FIG. 13.

Still referring to FIGS. 21A-B, in some embodiments, the electrode 30 includes one or more cut-outs, or flex slots, 38. The cut-out(s) 38 may be included for any purpose, such as to allow the electrode 30 to flex during insertion and/or removal from the electrode aperture 20 and/or flap 40. For example, the cut-out(s) 38 may allow the electrode 30 to be easily squeezed and snapped into place, and once in place in the headset 12, squeezed to be removed therefrom. The flex slots 38 may have any suitable form, configuration and operation. In the present embodiment, two cut-outs 38 extend from the bottom end 34 of the electrode 30 up to a desired location along the height of the side 31 (see also, FIGS. 4-5, 10A-B). The illustrated flex slots 38 may be useful, for example, for squeezing the electrode 30 proximate to its bottom end 34, or allowing the electrode 30 to flex thereabouts, during upward insertion and downward removal of the electrode 30 into/from the electrode aperture 20. In the embodiment of FIGS. 14 and 22, four cut-outs 38 are shown extending from the top end 35 of the electrode 30 to a desired location along the height of the side 31. The flex slots 38 in this embodiment may be useful, for example, for squeezing the electrode 30 proximate to its top 35, or allowing the electrode 30 to flex thereabouts, during downward insertion and downward removal of the electrode 30 into/from the electrode apertures 20.

Now referring to FIGS. 10B-C, the electrode cover 50 may have any suitable form, configuration, construction and operation. The cover 50 may or may not completely encapsulate the electrode 30 and may or may not be glued or otherwise secured to the electrode 30, as desired. When it is desired to secure the cover 50 to the electrode 30, any suitable technique may be used. For example, the cover 50 may include a draw string, elastic band(s) or the like that may be tightened to assist in retaining the cover 50 on the electrode 30. For another example, the cover 50 may be glued and/or heat-welded to the electrode 30. In some embodiment, the cover 50 may tightly fit and grip the electrode 30 without glue or any coupling mechanism.

Figure 24A:
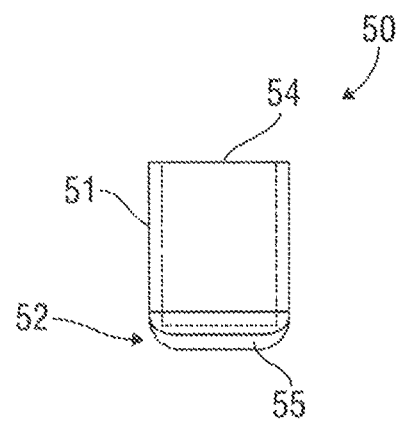
FIG. 24A is a side view of an exemplary electrode cover in accordance with an embodiment of the present disclosure.
Figure 24B:
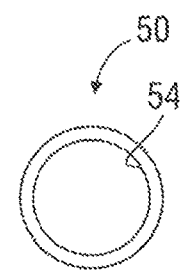
FIG. 24B is a top view of the exemplary electrode cover of FIG. 24A.

In the present embodiment, the exemplary cover 50 completely encapsulates the electrode. The illustrated cover 50 has an upper sock opening 54 for slipping the cover 50 over the bottom end 34 of electrode 30 that is tucked into the open top end 35 of the electrode 30. The illustrated cover 50 is glued or heat-welded around the opening 54 to close off the opening 54 and may also be glued or heat-welded thereabout to the inside of the electrode 30. In the embodiment of FIGS. 24A-B, the cover 50 will not completely encapsulate, and is not secured to, the electrode 30.

When the cover 50 is constructed of electrically-conductive liquid 90 absorbing material, the cover 50 may be constructed at least partially of cotton, natural or synthetic conductive material, fibers or fabric, any other liquid-absorbing and electrically-conductive material or a combination thereof. In some embodiments, multiple conductive fibers (not shown) may be woven into the cover 50 for lowering contact and/or path resistance. In various embodiments, the cover 50 may be at least partially constructed of exfoliating material (e.g. nylon), as is known and used in beauty industry, and/or have a textured or rough surface at the bottom end 52 thereof.

Figure 25:
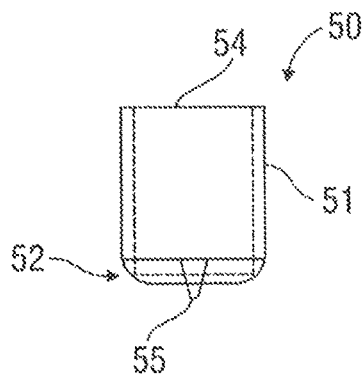
FIG. 25 is a side view of an exemplary electrode cover in accordance with another embodiment of the present disclosure.

Still referring to FIGS. 10B-C, if desired, the cover 50 may have a seam 55 disposed at the bottom end 52 of the cover 50 (see also, FIG. 25). The seam 55 may have any suitable form, configuration and operation. For example, the seam 55 may accumulate more electrically-conductive liquid 90 than the remainder of the cover 50, extend further into the subject's hair and against the scalp 102 than the body of the cover 50, be coarse or thick and useful to exfoliate the subject's scalp 102 if the electrode 30 is rotated or otherwise moved while in contact with the scalp 102, any other suitable purpose or a combination thereof.

Referring again to FIGS. 4-5, 12 and 18, in other independent aspects of the present disclosure, in some embodiments, the electrode 30 may be movable within the electrode aperture 20 as it engages the subject's scalp 102. For example, the electrode 30 may be rotatable to maneuver through the subject's hair and/or scrub, abrade or exfoliate one or more epidermal layers of the scalp 102 for improving electrical conductivity. As the exemplary electrode 30 is rubbed against the subject's scalp 102, the electrode 30 (or cover 50 thereon) may be used to rub, scrub, clean or abrade the scalp 102 to exfoliate the scalp 102 or remove dead skin therefrom, such as to assist in achieving better electrical contact and conductivity. The use of an electrode 30 (with our without cover 50) to rub, exfoliate or prepare the scalp for use of the headset system 10, such as described above, could be used instead of a blunt needle typically rubbed against the scalp to remove dead skin, exfoliate or otherwise prepare the scalp for use during such testing.

The electrodes 30 may be formed in different sizes, shapes and configurations. In some embodiment, the electrodes 30 may be replaceable on a per patient basis, such as for cleanliness, optimizing electrical conductivity (if they dry out or are calibrated for wetness) or other purpose. In various embodiments, different electrodes 30 may be used on the headset 12 for a particular subject and/or at different locations in the cap 12, such as to improve electrical conductivity or for other reasons. For example, different sized, shaped or configured electrodes 30 may be provided to accommodate different electrode positions on the cap 12 for a particular subject to improve or optimize electrical conductivity at each location. For another example, electrodes 30 constructed of different materials and/or some with and some without covers 50 may be used for a particular subject.

For use of the exemplary systems 10, the electrodes 30 (or covers 50, when included) are laden with one or more electrode wetting agents to provide or enhance electrical conductivity.

Referring back to FIGS. 1-5, in another independent aspect of the present disclosure, an electrically-conductive liquid, or formula, 90 may be placed upon each electrode 30 (and/or cover 50, when included) as the electrode wetting agent. For example, the electrically-conductive liquid 90 may be useful to lower contact resistance at the scalp and/or to lower path resistance for signal flow (e.g. arrows 109, FIG. 19C) from the bottom end 34 of the electrode 30 to wire lead 70 to a desired level. In many embodiments, the electrically-conductive liquid 90 may be designed to possess electric conductivity attributes that will allow or match the input impedance specified for the particular signal amplifier of the test (EEG or other brainwave measurement) system being used. In some embodiments, for example, the electrically-conductive liquid 90 may be designed to possess electrical conductivity attributes that allow the electric path resistance for signal flow (e.g. arrows 109, FIG. 16C) to be maintained at less than 80 k ohms, and, in some instances, less than 40 k ohms and, in some instances, less than 5 k ohms impedance.

The electrically conductive liquid 90 may have any suitable composition and properties. In accordance with various embodiments, the electrically-conductive liquid 90 includes a hair conditioner and/or an optical/contact lens solution. In some embodiments, such as when a gel would normally be used during the test, the electrically-conductive liquid 90 may include the hair conditioner, such as, for example a "leave-in" hair conditioner. This form of electrically-conductive liquid 90 may be combed into the hair after the test and the hair may be returned to its normal appearance. The use of hair conditioner in the electrically-conductive liquid 90 may also, in at least some situations, serve the function of nourishing the hair. The use of hair conditioner in the electrically-conductive liquid 90 may also allow typical subjects to resume their day or nighttime activities without having to wash their hair. For example, if the test is conducted during a routine physical exam, the subject may be able to immediately return to work or his/her other activities, as opposed to having to first wash his/her hair.

When used in the electrically-conductive liquid 90, the hair conditioner may have any suitable ingredients and liquid properties. One example presently commercially available leave-in conditioner that could be included in, or used as, the electrically-conductive liquid 90 in some embodiments is "PAUL MITCHELL® THE CREAM® Leave-in Conditioner and Styler", having the following ingredients: Water, PVP, Glycerin, Yeast (Faex) Extract, Methyl Gluceth 10, Stearalkonium Chloride, *Simmondsia chinensis* (Jojoba) Seed Oil, Carthamus Tinctorius (Safflower) Seed Oil, Amodimethicone, Bisamino PEG/PPG 41/3 Aminoethyl PG Propyl Dimethicone, Panthenol, Ethylhexyl Methoxycinnamate, Benzophenone 4, Guar Hydroxypropyltrimonium Chloride, Cetearyl Alcohol, Hydroxyethylcellulose, Polysorbate 60, Phenoxyethanol, C11 15 Pareth 7, Trideceth 12, Laureth 9, Citric Acid, Methylparaben, Propylparaben, Disodium EDTA, Diazolidinyl Urea, Fragrance, Hexyl. In various embodiments, an exemplary electrically-conductive liquid 90 may include any particular two or more of the above-listed ingredients.

Another example presently available leave-in conditioner that could be included in, or used as, the electrically-conductive liquid 90 in various embodiments is "Generic Value Products Cream", presently available at Sally Beauty Supply, LLC as Sally Item No. SBS-264043 and having the following ingredients: Water (Aqua), PVP, Glycerin, Yeast Extract, Methyl Gluceth-10, Stearalkonium Chloride, *Simmondsia chinensis* (Jojoba) Seed Oil, Carthamus Tinctorius (Safflower) Oil, Amodimethicone, Bisamino PEG/PPG-41/3 Aminoethyl PG-Propyl Dimethicone/*Hedychium coronarium* (White Ginger)/PEG-12 Dimethicone, Panthenol, Ethylhexyl Methoxycinnamate, Benzophenone-4, Guar Hydroxypropyltrimonium Chloride, Cetyl Alcohol, Cetearyl Alcohol, Hydroxyethylcellulose, Polysorbate-60, Phenoxyethanol, C11-15 Pareth-7, Trideceth-12, Laureth-9, Citric Acid, Fragrance(Parfum), Methylparaben. In many embodiments, an exemplary electrically-conductive liquid 90 may include any particular two or more of the above-listed ingredients. However, the present disclosure is not limited to these particular examples.

In some embodiments, the electrically-conductive liquid 90 include optical/contact lens solution. In various embodiments, the optical/contact lens solution may provide eye soothing and/or disinfecting benefits and/or be less sticky.

When included in the electrically-conductive liquid 90, the optical/contact lens solution may have any suitable ingredients and liquid properties. For example, one presently commercially available optical/contact lens solution that could be included in some embodiments of the electrically-conductive liquid 90 is "Renu Sensitive Multi-Purpose Solution" by Bausch & Lomb Incorporated and having the ingredients of a sterile, isotonic solution that contains boric acid, edetate disodium, poloxamine, sodium borate and sodium chloride; preserved with DYMED® (polyaminopropyl biguanide) 0.00005%. In many embodiments, an exemplary electrically-conductive liquid 90 may include any particular two or more of the above-listed ingredients. However, the present disclosure is not limited to this particular example.

Figure 11A:
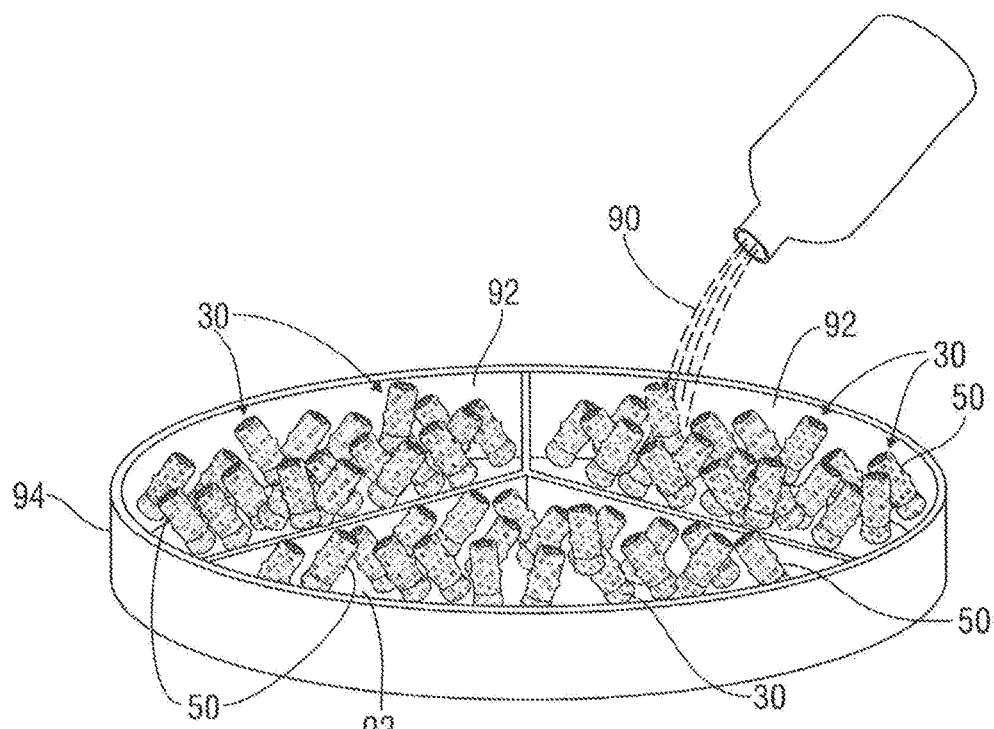
FIG. 11A is a perspective view of an exemplary tray of an exemplary electrode storage system in accordance with an embodiment of the present disclosure.
Figure 11B:
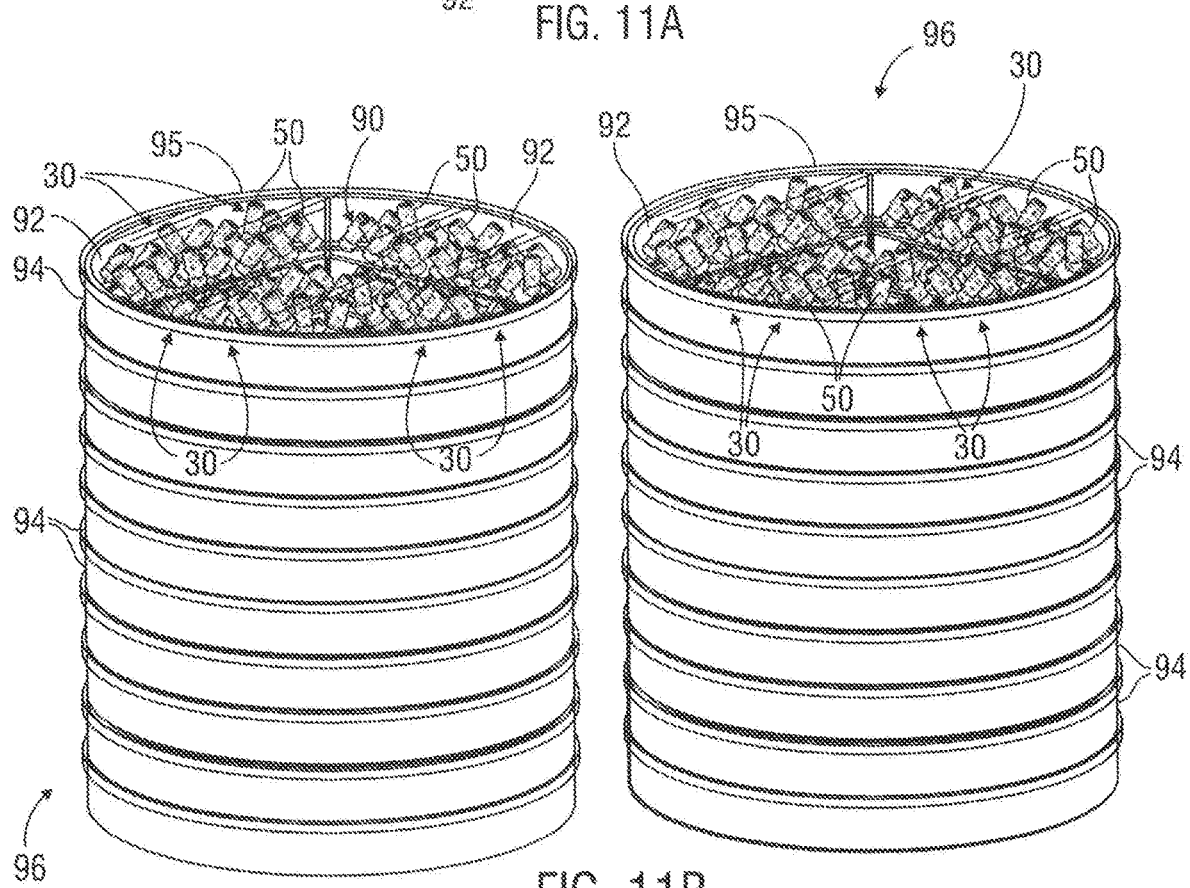
FIG. 11B is a perspective view of an exemplary electrode storage system in accordance with an embodiment of the present disclosure.
Figure 12:
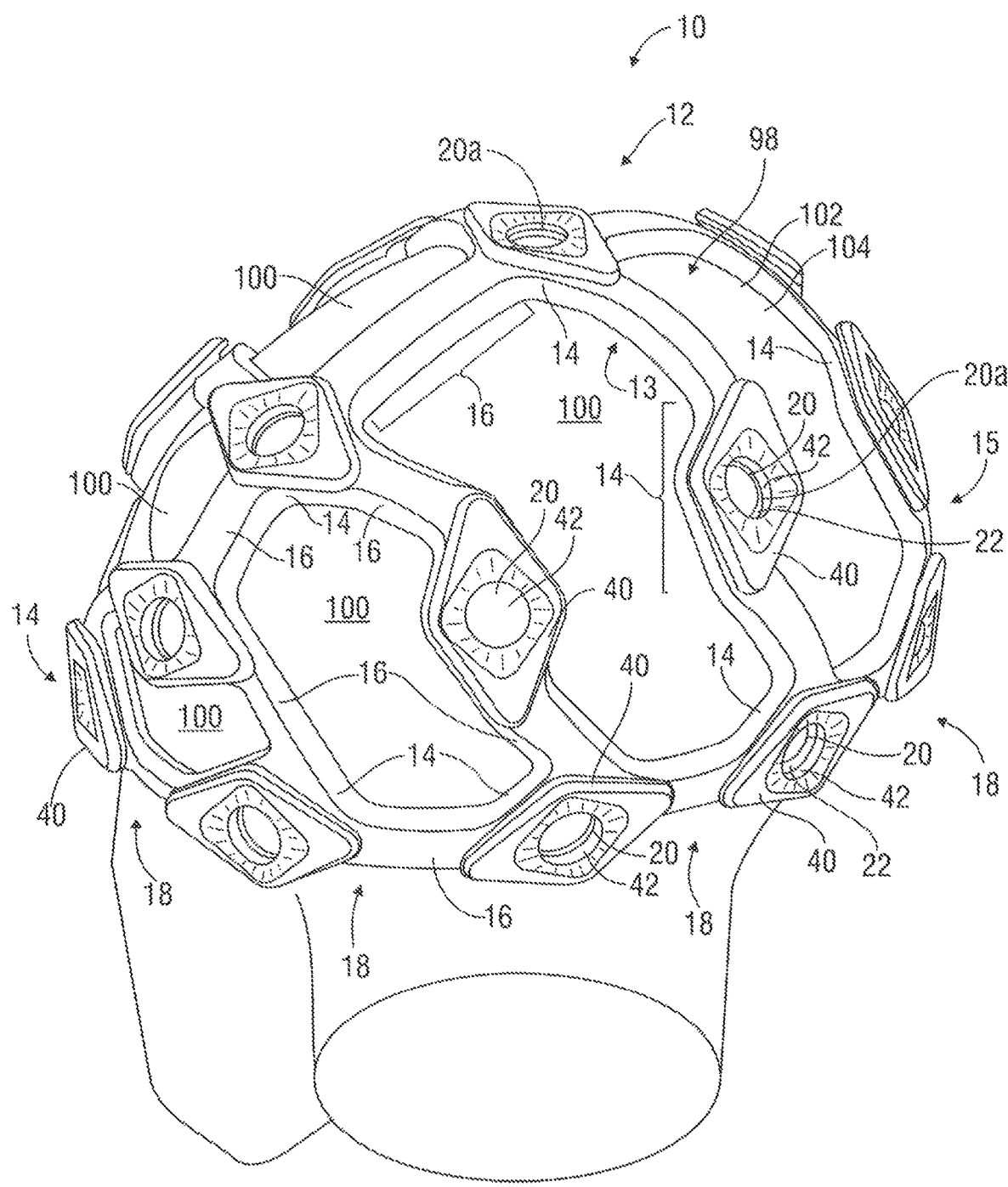
FIG. 12 is a perspective view of an exemplary signal receiving headset system shown positioned on a human subject's head in accordance with another embodiment of the present disclosure.

The electrodes 30 (or covers 50) may be laden with the electrically-conductive liquid 90 in any suitable manner. In some embodiments, the electrodes 30 may be first inserted into the headset 12 and then laden with electrically-conductive liquid, such as with a squirt bottle or other applicator. In other embodiments, for example, the electrodes 30 (with our without the covers 50) may be pre-packaged wet with the electrically-conductive liquid 90. For example, the presoaked electrodes 30 may be stored in a sealed plastic pouch. For another example, in the embodiment of FIGS. 11A-B, the necessary quantity of electrodes 30 for the desired test is prepackaged in separate sections 92 of distinct plastic electrode trays 94 of an electrode storage system 96. In this example, three distinct tray sections 92 each hold twenty electrodes 30 (for a typical EEG test), and ten trays 94 are shown stacked and releasably engaged upon one another for ease of storage, delivery, transport, etc. When the associated headset 12 needs to be fitted with a set of electrodes 30, a tray 94 is uncovered (e.g. by removal of a cover 95 or an upper tray 94) and the electrically-conductive liquid 90 is squirted, sprayed or poured onto the electrodes 30 in a first tray section 92, preserving the dry status of the other electrodes 30 in the tray 94 and storage system 96 for future use.

Figure 41:
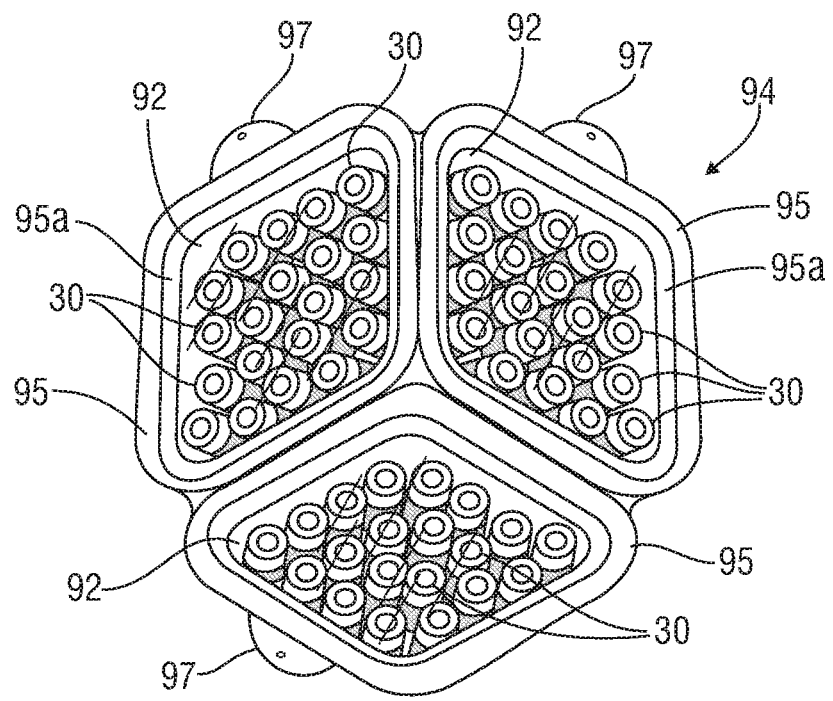
FIG. 41 is a front view of an exemplary tray of an exemplary electrode storage system in accordance with an embodiment of the present disclosure.
Figure 42:
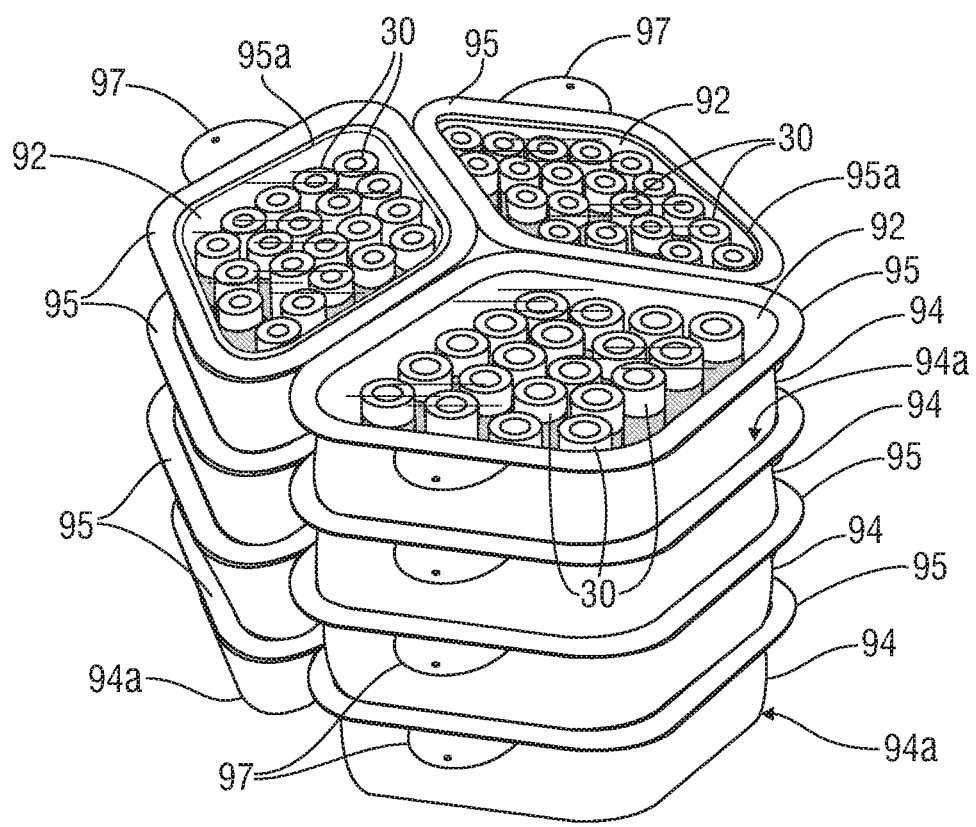
FIG. 42 is a perspective view of an exemplary electrode storage system having numerous of the exemplary trays of FIG. 41 in accordance with an embodiment of the present disclosure.

In the embodiment of FIGS. 41-42, the exemplary tray 94 (e.g. constructed of plastic) has a hexagonal shape and its distinct sections 92 are diamond-shaped, such as to provide a streamlined, easy to stack and store electrode packaging and preparation system, for ease of manufacture, other desired purpose or a combination thereof. However, the tray 94 and its sections 92 may have any other desired shape, such as oval, oblong, square, triangular, octagonal, etc. If desired, different sections 92 of the same exemplary tray 94 may have different shapes. Further, while three sections 29 each holding twenty electrodes 30 are provided in the exemplary tray 94, the tray 94 may include any desired number of sections (e.g., 1, 2, 4, 5 or more) for holding any desired number of electrodes 30 (e.g. 1-19, 21 or more).

Still referring to FIGS. 41-42, the illustrated tray 94 includes a distinct, separately removable cover 95 for each tray section 92. The covers 95 may have any suitable form, configuration and operation. For example, each cover 95 may include at least one tab 97 for easy gripping of the cover 95. For another example, each cover 95 may be at least partially transparent so the contents (e.g. electrodes 30) therein are visible. For still a further example, the cover 95 may be formed with a recess 95a to allow seating therein of part of the lower end 94a of another tray 94 (e.g. one of its sections 92) for stacking or nesting of multiple trays 94.

Referring to FIGS. 1-5, the electrically-conductive liquid laden electrodes 30 may then be inserted in to the headset 12 (see also, FIGS. 12-19C). The exemplary headset system 10 may then be placed and/or fitted on the subject's head 98 so that each (electrically-conductive liquid laden) electrode 30 is positioned to contact the scalp 102 as desired. However, if the contact between any electrode 30 is not satisfactory or for any other suitable reason, the administrator of the test may add additional electrically-conductive liquid 90 between the electrode 30 and the scalp 102. For example, additional electrically-conductive liquid 90 containing optical/contact lens solution may be inserted between the electrode 30 and scalp 102, such as with a squirt bottle, blunt needle, plastic syringe or other applicator. For another example, electrically-conductive liquid 90 containing hair conditioner may be inserted between the electrode 30 and scalp 102, such as with a squirt bottle, tube, blunt needle, plastic syringe or other applicator.

In some scenarios, electrically-conductive liquid 90 in the form of both the optical/contact lens solution and hair conditioner may be added between an electrode 30 and the scalp 102. For example, if the optical/contact lens solution is added and does not sufficiently enhance the desired electrical conductivity, the hair conditioner may then be added. For another example, if it is desirable to avoid dripping of the electrically-conductive liquid 90 at or around a particular electrode site, the hair conditioner (or an electrically-conductive liquid 90 with a mixture of ingredients that includes hair conditioner) may be preferred. It may be desirable to avoid dripping of the electrically-conductive liquid 90, for example, at electrode sites at locations that may be more prone to dripping, such as along the side of the subject's head 98. For example, if added electrically-conductive liquid 90 would be likely drip onto an area of the scalp 102 between adjacent electrodes 30, the dripped electrically-conductive liquid 90 could cause the signal measurements of adjacent electrodes 30 to be distorted. At such electrode sites, it may thus be desirable to use the hair conditioner as the (added) electrically-conductive liquid 90 because it is less likely to drip.

In some scenarios, the subject may have a preference as to which electrically-conductive liquid 90 to use on their head 98. For example, subject's having hair that has been straightened may have a heightened desire not to wet their hair because wetting may reverse or remove the straightening. In such instances, the subject may prefer the use of the hair conditioner-type electrically-conductive liquid 90 to preserve the straightening of their hair. Another exemplary situation where it may be preferred to add the hair conditioner instead of optical/contact lens solution is when the viscosity or thickness of the electrically-conductive liquid 90 is important. This may be the case, for example, when the headset 12 is placed or fitted onto the subject's head 98 and a gap exists between one or more of the electrodes 30 and the scalp 102. For example, the subject's hair style (e.g. cornrows) may not allow an electrode 30 to get close enough to the scalp 102 to sufficiently receive signals from the subject's brain. In such instance, the thickness or viscosity of the hair conditioner may fill the gap between the electrode 30 and scalp 102 sufficient to provide acceptable conductivity between the head and the electrode 30.

In some embodiments, the electrodes 30 (laden with electrically-conductive liquid) may be first positioned in the headset 12 in a retracted position. Thereafter, the headset 12 may be fitted onto the subject's head 98 without dripping the electrically-conductive liquid all over the head 98 or dragging the moist electrodes 30 across or along the subject's head 98. After the headset 12 is positioned on the subject's head 98, each electrode 30 may then, if necessary, be moved into an extended positioned into contact with or proximate to the subject's scalp 102 without dripping or dragging. In some instances, good contact is made with the scalp 102 and the signal transmission path from the scalp 102 to the electrode 30 is acceptable. However, after the test is initiated, if the electrical impedance or conductivity is insufficient, additional electrically-conductive liquid 90 (e.g. optical/contact lens solution, hair conditioner or a combination thereof) may be added as needed.

Referring now to FIGS. 36A-37, the exemplary system 10 may include one or more ear clips, or ear-clip assemblies, 200 to be used as an EEG reference electrode and/or a ground for EEG testing with the headset 12 utilizing EEG principals as are and become further known. The ear-clip assembly 200 may have any suitable form, configuration and operation. In this embodiment, left and right side ear-clip assemblies 200a are configured to be coupled between the headset 12 and the subject's respective ear lobes 101 for serving as EEG reference electrodes. However, other embodiments may utilize any combination of one or two ear-clip assemblies 200 to serve as one or more EEG reference electrodes and/or one or more grounds for EEG testing.

The ear clip 200 may engage the subject's ear lobe in any suitable manner. Each exemplary ear-clip assembly 200a includes a clamp 204 having at least first and second prongs 208, 210 which releasably clamp onto the subject's left or right earlobe 101 and place squeezing forces on opposite sides of the earlobe 101 sufficiently tightly to make electrical contact with and be able to receive electrical signals from the earlobe 101 (e.g. to allow reliable referencing and/or grounding of the EEG system) and retain the clamp 204 on the earlobe 101 as desired. One or both prongs 208, 210 and associated handle(s) 206 of the illustrated clamp 204 are at least partially constructed of electrically conductive material (e.g. metal) sufficient to make electrical contact with and be able to receive electrical signals from the earlobe 101 (e.g. typically zero voltage) and cause reliable referencing and/or grounding of the EEG system. In the illustrated embodiments, both prongs 208, 210 and their handles 206 (e.g. FIG. 38) are constructed of metal and are able to receive electrical signals from the subject's earlobe 101.

Referring to FIG. 36A, if desired, one or both prongs 208, 210 of the exemplary clamp 204 may at least partially include a comfort coating 211 (e.g. rubber, plastic, fabric) for comfort, so long as there is sufficient metal-to-skin contact between at least one prong (e.g. prong 210) and the subject's earlobe 101. For example, the first prong 208, which abuts the back of the subject's earlobe 101 and may rub against the subject's head 98 or neck behind the ear during use of the headset 12, may include one or more comfort coatings 211. In this embodiment, a rubber sheath 212 at least partially covers the first prong 208 of the clamp 204. In other embodiments, the coating 211 may be constructed of the same or similar material as the strips 16 and/or electrode stations 14 (e.g. foam, Croslite™, silicon, Trileon™, any other type of EVA) or a combination of materials that have any one or more of the potential characteristics of the strips 16 and electrode stations 14 as described above.

Referring now FIGS. 36A-37, the exemplary ear-clip assembly 200a also includes at least one connection wire 214 extending between the clamp 204 and a conductive interface 218. These components may have any suitable form, configuration and operation. In this embodiment, each ear-clip assembly 200a includes a single electrically conductive, connection wire 214 having first and second ends 214a, 214b and a protective outer sheath 216 (e.g. rubber or plastic) extending therebetween. The exemplary conductive interface 218 is provided proximate to the second end 214b of the wire 214 and is configured to be releasably engaged with the headset 12 and electrically coupled to at least one of the signal transmission wires 70 (e.g. FIG. 32) in the headset 12. For example, the ear-clip assembly 200a may include a protective housing 220 at least partially surrounding the conductive interface 218 at the second end 214b of the wire 214 and releasably engageable with the headset 12. In this embodiment, the housing 220 includes a connection portion 222 that at least partially surrounds and/or protects the conductive interface 218 and is releasably engageable with at least one conductive receiver 226 on the headset 12 (e.g. FIGS. 27 & 35). The exemplary housing 220 also includes a base portion 230 (e.g. FIG. 36B), such as for gripping and handling the housing 220 and/or protecting the conductive interface 218 and the electrical interconnection of the wire 214 and conductive interface 218 and/or other desired purpose(s).

The ear clip 200 may be coupled to the headset 12 in any suitable manner. In the embodiment of FIG. 3, for example, the second end 214b of the connection wire 214 includes a plug 215 (or other connector) engageable within a receiver, or socket, 234 associated with the headset 12 and electrically coupled to at least one of the signal transmission wires 70. In FIGS. 36A-37, the connection portion 222 of the housing 220 of the ear-clip assembly 200a is magnetically, releasably coupled to the conductive receiver 226 (e.g. FIGS. 27 & 35) of the headset 12. For example, each conductive receiver 226 of the illustrated headset 12 includes at least one magnet 223 secured to the headset 12 on one, or the other, side 116, 117 of the headset 12 and electrically coupled to at least one of the signal transmission wires 70 (e.g. FIG. 32) in the headset 12. The exemplary connection portion 222 of the housing 220 also includes at least one magnet 224, having the opposite magnetic pole facing outwardly as the outwardly facing magnetic pole of the conductive receiver 226, so that the connection portion 222 and conductive receiver 226 are releasably, magnetically engageable when the housing 220 is placed adjacent to the receiver 226.

Magnetic connection of the exemplary ear-clip assembly 200 and headset 12 may be provided for any desired purpose(s). For example, the magnetic connection of the ear-clip assembly 200 and headset 12 may be configured to provide an easy and reliable break-away connection of the ear-clip assembly 200 from the headset 12. For example, when the subject forgets to disconnect each clamp 204 from his/her ears when removing the headset 12, or moves and unintentionally places stress upon one or both of the ear-clip assemblies 200 or their connection wires 214, the magnetic connection can be configured to disengage before the clamp 204 bends, breaks or substantially pulls on or tears the subject's ear, hopefully avoiding at least substantial discomfort to the subject and damage to the ear-clip assembly 200 and subject's ear. If desired, the magnetic connection may be configured so that a desired amount of tension or pulling on the ear-lip assembly 200 or its connection wire 214 will disconnect the ear-clip assembly 200 from the headset 12. For another example, a magnetic connection of the ear-clip assembly 200 and the exemplary headset 12 can be simple, unlikely to become damaged when disconnected or over multiple uses, long lasting, durable, easy and cost-effective to manufacture, made with few components, configured to provide a sufficiently strong connection, or a combination thereof. For yet another example, a non-magnetic connection (e.g. mechanical) of the ear-clip assembly 200 to the exemplary headset 12 may include more components that can malfunction, be more complex and/or more costly to manufacture, be more likely to become subject to wear, breakage and/or damage when disconnected and/or over multiple uses, or a combination thereof.

Figure 38:
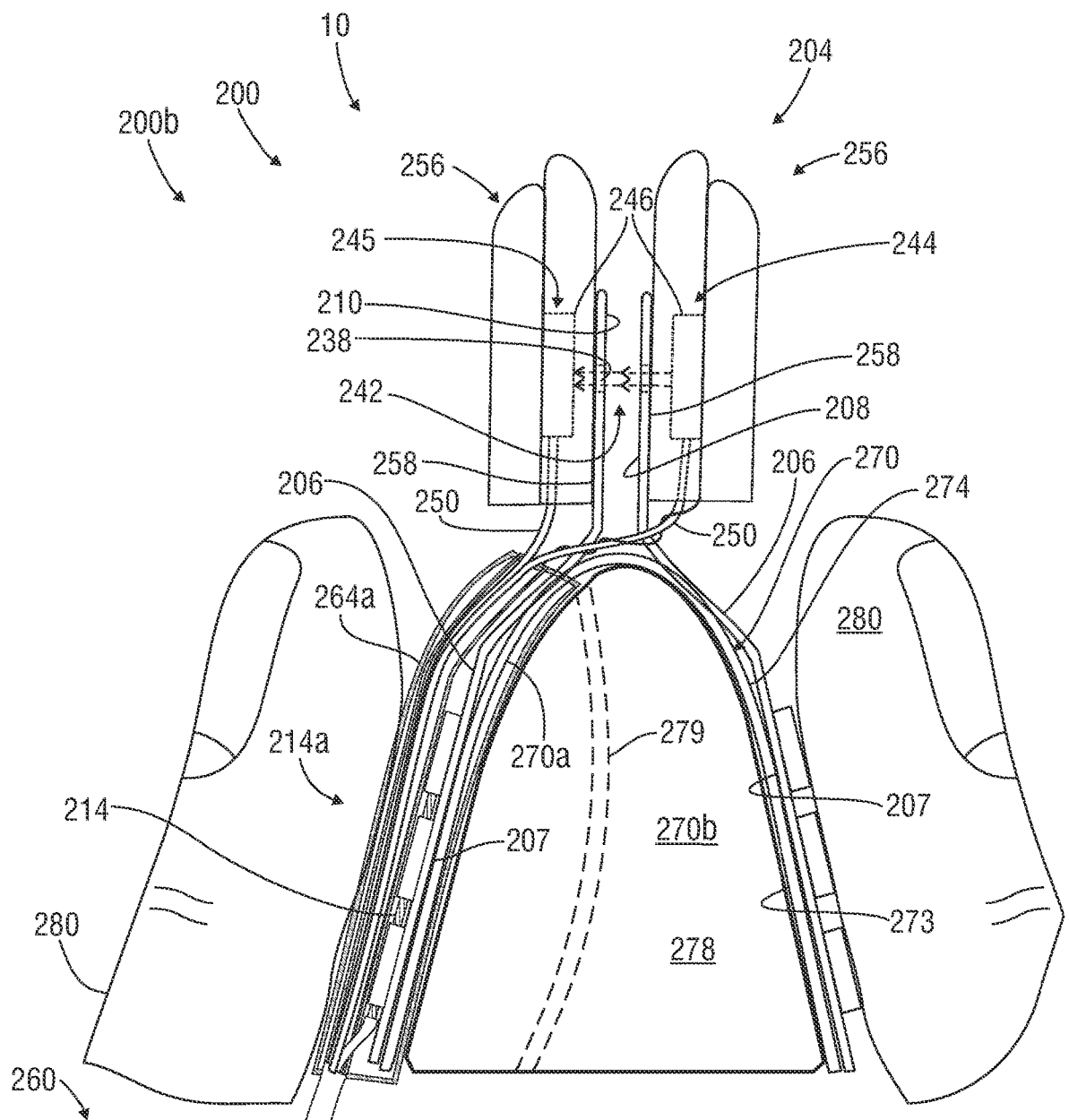
FIG. 38 is an exploded side view of another embodiment of an ear-clip assembly useful with a headset system in accordance with one or more embodiments herein.
Figure 39:
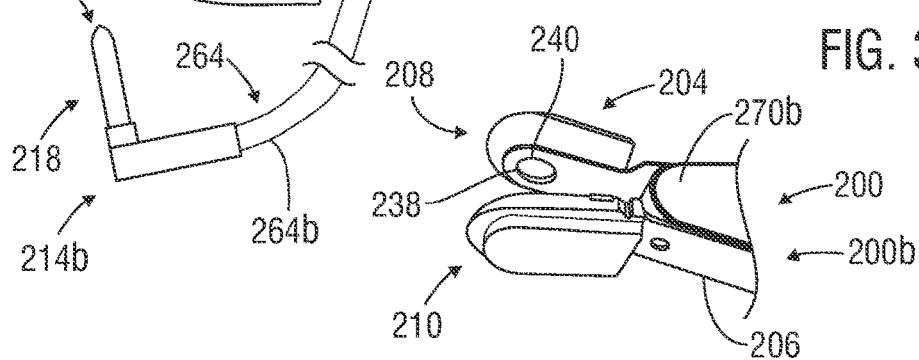
FIG. 39 is a perspective view of part of the ear-clip assembly of FIG. 38.
Figure 40:
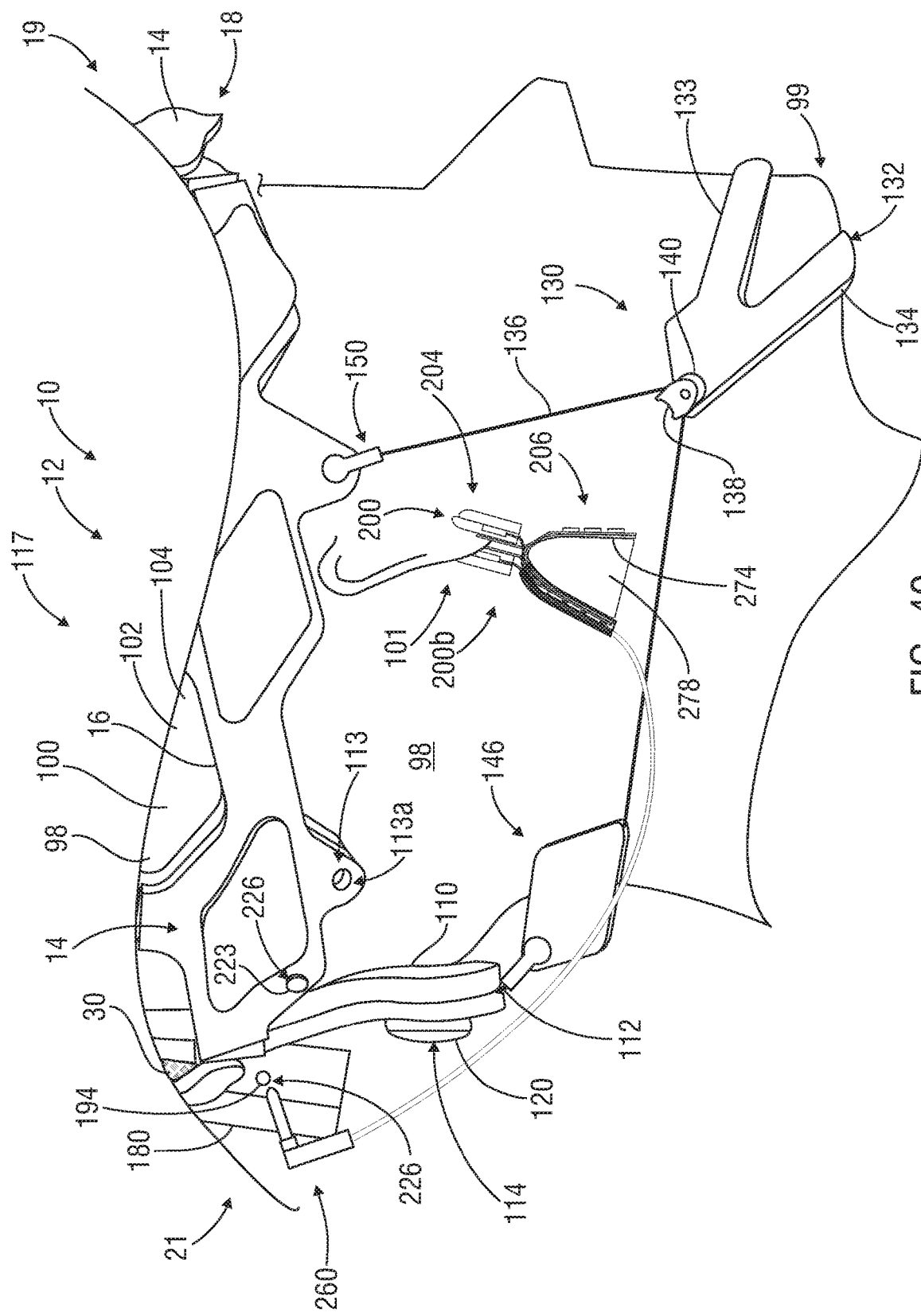
FIG. 40 is a partial side of the exemplary headset system of FIG. 27 with the exemplary ear-clip assembly of FIG. 39 being coupled thereto.

Now referring to FIGS. 38-40, in some embodiments, the headset 12 may be used for any additional forms of human diagnostic or physiological testing (other than taking brainwave measurements). For example, the headset 12 may be used for measuring or obtaining one or more vascular parameters. As used herein and in the appended claims, the terms "vascular parameter" and variations thereon means any vascular, or cardiac, variable or measurement that may be taken, measured or derived based upon information from a human subject, such as, without limitation, one or more among the pulse, heart rate, blood oxygen content, heart rate variability, pulse rate variability, pulse transit time, blood pressure, pulse wave amplitude and the like. For example, the system 10 may be capable of taking a PPG of the subject (e.g. to measure pulse, heart rate, heart rate variability, pulse rate variability, etc.). The system 10 may include any suitable mechanism(s) and technique(s) for obtaining the PPG as are and become further known. For example, one or more ear-clip assemblies 200b may be used for obtaining the PPG. In this embodiment, left and right side ear-clip assemblies 200b are each multi-configured for obtaining PPG measurements and to be used (such as described above) as an EEG reference electrode and also, if desired, a ground, for EEG testing. The illustrated ear-clip assembly 200b is thus an example of a combination, or multi-purpose, ear-clip assembly 200. However, in other embodiments, only one of the ear-clip assemblies 200 could be used for any one or more of those capabilities, both ear-clip assemblies 200 may be used for only PPG testing, only EEG grounding or as an EEG reference electrode or any combination or variation thereof. As used herein and the appended claims, the terms "multi-purpose ear clip", "multi-purpose ear-clip assembly" and variations thereof mean an ear-clip useful for performing PPG testing and serving as an EEG reference electrode and/or a ground for EEG testing.

Still referring to FIGS. 38-40, the illustrated ear-clip assembly 200b may be configured to incorporate all, or any combination, of the features of the ear-clip assembly 200a described above. Further, the first and second prongs 208, 210 of the illustrated clamp 204 are configured and gaged to provide squeezing forces on opposite sides of the subject's earlobe 101 sufficiently tightly to make electrical contact with or receive electrical signals from the earlobe 101 and retain the clamp 204 on the earlobe 101 as desired, but without substantially disturbing, suppressing, arresting or cutting-off the pulse of blood vessels in the earlobe 101 between the prongs 208, 210 to allow the ear clip 200b to be used to take at least one PPG measurement of the subject and as an EEG reference electrode, and if desired, as an EEG system ground.

The ear clip 200b may be configured to take PPG measurements in any suitable manner and with any PPG technology as is and becomes further known. In this embodiment, at least one window 238 is associated with at least one of the prongs 208, 210 of the clamp 204 to receive one or more light signals 242 passed through the patient's earlobe 101 to enable one or more PPG measurements. For example, at least one window 238 may be associated with each prong 208, 210. In this embodiment, a circular aperture 240 is formed in each prong 208, 210. In other embodiments, one or more apertures 240 in each prong 208, 210 may have any other shape (square, triangular, oblong, etc.) and the window (s) 238 may take any other the form or configuration (e.g. as cut-outs in one or more of the prongs 208, 210, spaces adjacent to the prongs 208, 210, etc.). Thus, the present disclosure and appended claims are not limited by the form, configuration and quantities of windows 238, except and only to the extent as may be expressly recited and explicitly required in a particular claim hereof and only for such claim(s) and any claim(s) depending therefrom.

Still referring to FIGS. 38-40, the light signal(s) 242 may be passed through one or more windows 238 of one or both prongs 208, 210 of the exemplary clamp 204 and subject's earlobe 101 in any suitable manner. For example, at least one light transmitter 244 may be associated with one prong 208, 210 and at least one light receiver 245 associated with the other respective prong 208, 210. If desired, either the light transmitter 244 or light receiver 245 may be capable of both transmitting and receiving light signals 242. The light transmitter 244 and light receiver 245 may have any suitable form, configuration and operation. In this embodiment, the light transmitter 244 and receiver 245 each include at least one PCB 246 positioned proximate to the corresponding windows 238 in the corresponding prong 208, 210 and configured to send and/or receive one or more light signals 242. The PCBs 246 may have any suitable form, configuration, components and operation. For example, the PCBs 246 may each include at least one diode for sending and/or receiving a light signal and/or performing other related functions (e.g. send or receive multiple pulsed light signals and/or other data, organize, interpret, convert or send data, or a combination thereof).

The exemplary light transmitter 244 and light receiver 245 may communicate with any desired electronic controller, data processor, measuring device or the like. In this embodiment, the light transmitter 244 and light receiver 245 are electrically (or electronically) coupled to the EPU 180 with one or more connection wires 250 for the receipt of and/or transmission of signals and/or data therebetween. In this embodiment, a single connection wire 250 is shown extending to each of the light transmitter 244 and light receiver 245, but other embodiments may include two or more wires 250 to each or either the light transmitter 244 and light receiver 245. For example, a first wire 250 to the light transmitter 244 may activate one or more LEDs (e.g. provide power) to transmit the light signal(s) 242; if pulsing is desired, a second wire 250 to the light transmitter 244 may cause desired pulsing of the light signal (e.g. power off); and a third wire 250 to the light receiver 245 may affect the receipt of the light signal(s) 242 and/or transmit data to the EPU 180 or other destination. (Other embodiments may instead utilize wireless or other modes of communication and/or transmission of data.) In use of the exemplary embodiment, for example, the PCB 246 associated with the first prong 208 of the clamp 204 may serve as the light transmitter 244 and the PCB 246 associated with the second prong 210 may serve as the light receiver 245. In this particular arrangement, the light transmitter 244 will be configured to selectively project one or more light beams through the window 238 in the first prong 208 of the clamp 204, then through the subject's earlobe 101 and the window 238 in the second prong 210 to the light receiver 245, which receives the projected light beam(s), conducts any desired functions and transmits data to the EPU 180. If desired, the ear-clip assembly 200b may be configured to project multiple light beams or pulses in the same direction as described above, in the opposite direction or in both directions. Thus, the above exemplary configuration and functioning of the transmitter 244 and receiver 245 may be reversed, applicable to the other or varied in any other way. The present disclosure is not limited to this exemplary configuration and sequence, except and only to the extent as may be expressly recited and explicitly required in a particular claim hereof and only for such claim(s) and any claim(s) depending therefrom.

Still referring to FIGS. 38-40, the exemplary light transmitter(s) 244 and light receiver(s) 245 may be associated with the corresponding prongs 208, 210 of the clamp 204 in any suitable manner. In this embodiment, the light transmitter(s) 244 and light receiver(s) 245 (e.g. PCB's 246) are each mounted within a respective housing 256 associated with the prongs 208, 210. The housings 256 may have any suitable form, configuration and construction and may be associated with the prongs 208, 210 in any suitable manner. For example, the housings 256 may be constructed of plastic (rubber, etc.) and glued to the outer side 258 of the respective prong 208, 210, slid over the respective prong 208, 210, mechanically coupled to the clamp 204, integral to the clamp 204 or a combination thereof.

The connection wires 250 may be electrically coupled to the EPU 180 or other controller or data processor in any suitable manner. In this embodiment, for each ear-clip assembly 200b, all of the connection wires 250 and the connection wire 214 may be bundled together and terminate at a single plug 260 (e.g. five-pin connector) engageable with a respective socket, or port, 194 (e.g. five-pin receiver) in the EPU 180. For example, with respect to the connection wire 214, the plug 260 may serve as the conductive interface 218 and/or the protective housing 220 to protect at least part of the conductive interface 218 and/or the electrical interconnection of the wire 214 and conductive interface 218 and the port 194 serve as the conductive receiver 226. In other embodiments, only the connection wires 250 may be bundled together and terminate at the plug 260, and the connection wire 214 and associated conductive interface 218 coupled to the headset 12 separately (e.g. as described above with respect to the exemplary ear-clip assembly 200a). If desired, a magnetic connection may be used, such as similarly as described above with respect to the connection of the EPU 180 to the headset 12 and/or the connection of the ear-clip assemblies 200a to the headset 12 and provide any of the same potential benefits.

Referring now specifically to FIG. 38, if desired, one or more protective outer sheaths (e.g. rubber or plastic) 264 may be included to bundle and/or protect any desired combination of the wires 214, 250. In this embodiment, a first outer sheath 264a secures the wires 214, 250 to one of the handles 206 of the clamp 204 and a second outer sheath 264b encases the wires 214, 250 to the plug 260.

One or more biasing members 270 may be used to assist in retaining the clamp 204 in an engaged position with the subject's earlobe 101, providing the desired pressure on the earlobe 101 by the clamp 204, preventing the clamp 204 from undesirably disengaging from the subject's earlobe 101, other desired purpose or a combination thereof. The biasing member(s) 270 may have any suitable form, configuration and operation. In this embodiment, a first biasing member 270a is a spring 274 (e.g. elongated metallic rod) acting on the inner sides 207 of the respective handles 206 of the clamp 204 and biasing them outwardly to bias the prongs 208, 210 in the closed direction or position. The exemplary spring 274 is sufficiently spring-loaded and elastic to temporarily bend upon the application of sufficient squeezing pressure to the clamp handles 206 to open the clamp 204. If desired, the first biasing member 270a may also serve as an electrically conductive path for the EEG reference and also, if desired, serve as an EEG system ground.

Still referring to FIG. 38, a second biasing member 270b is also included in this embodiment to add resiliency to the first biasing member 270a, assist in preventing weakening and ineffectiveness of the first biasing member 270a, assist in retaining the clamp 204 in an engaged position with the subject's earlobe 101 (e.g. FIG. 40), assist in providing the desired pressure on the earlobe 101 by the clamp 204, assist in preventing the clamp 204 from undesirably disengaging from the subject's earlobe 101, other desired purpose or a combination thereof. In this embodiment, the second biasing member 270b is a removable, semi-rigid insert 278 that is releasably insertable along the inner side 273 of the first biasing member 270a. The illustrated insert 278 is wedge-shaped (e.g. to generally correspond with the shape of the first biasing member 270a) and constructed of foam, but may have any desired shape and construction (e.g. plastic, rubber, etc.). The exemplary insert 278 and will compress upon the application of sufficient squeezing pressure to the clamp handles 206 to open the clamp 204. It should be noted that in FIG. 38, the exemplary clamp 204 is shown in an open position as if squeezing pressure were being applied to the handles 206 (e.g. by a person's fingers 280). If desired, the second biasing member 270b may be configured to seat or hide one or more of the wires 214, 250. For example, instead of all or some of the wires 214, 250 passing on the outside of the clamp 204 (e.g. along the outside of one or more of the prongs 208, 210), the wires 214, 250 could pass through one or more passageways 279 provided in the second biasing member 270b.

For another example, the system 10 may be capable of taking an ECG of the subject (e.g. to assist in measuring or determining pulse transit time, blood pressure, pulse wave amplitude, etc.). The system 10 may include any suitable mechanism(s) and technique(s) for obtaining the ECG using ECG technology is and becomes further known. For example, referring to FIGS. 31A-B, the EPU 180 may be releasably coupled to an ECG measurement device 300 (e.g. traditional ECG lead set, an ECG chest strap, wrist band/watch and/or other forms of ECG devices releasably coupled to the subject), such as at ports 192. If desired, the exemplary EPU 180 may be configured with hardware and/or software for communicating with the ECG device(s) coupled thereto, receiving, processing, analyzing or organizing data, or a combination thereof and/or providing data relating thereto to the controller/measuring device(s) 108.

In some embodiments, the EEG and one or more other human medical diagnostic or physiological tests (e.g. measuring a vascular parameter) may be obtained simultaneously. In the present embodiment, this capability may be useful, for example, to measure both brain (e.g. EEG) and vascular (e.g. via PPG, ECG) responses during a cognitive test conducted with the use of the headset 12 or any other suitable purpose.

In the illustrated embodiments, the headset 12 is configured to perform all of the functions described above (e.g. EEG and PPG testing, data communication, etc.) without the need for batteries or other internal power source and to receive any necessary power from one or more controllers or measuring devices 108 (e.g. laptop computer, smartphone, tablet, etc.) coupled thereto. However, other embodiments may obtain power from batteries or any other suitable internal (e.g. solar power) or external sources. If desired, the above-described hard-wired examples of communication and/or data transmission between components may instead utilize wireless or other modes of communication and data transmission as are and become further known.

In various embodiments, the present disclosure may include any of the features mentioned above and/or one or more of the following features: a lightweight headset system 10 that adjustably conforms to a wide range of head sizes and shapes; a headset system 10 having electrodes 30 that may be visibly inspected and adjusted for one or more purposes, such as to make adjustments or changes to improve electrical conductivity and signal transmittal (e.g. accommodate a wide range of hair types, skin dryness, patient sensitivities to pressure, etc.); a headset system 10 that may be inexpensively reused and shared with multiple patients with less risk of transfer dirt, oil, germs. etc.; electrodes 30 that are replaceable and/or may be replaced with another style, size or configuration electrode 30; an electrically-conductive liquid 90 useful between the electrodes 30 and the subject's head 98, may be used to provide sufficient electrical conductivity for subjects with different hair styles and conditions, does not require washing or cleaning the hair and scalp after the test or any combination thereof; or a combination thereof.

Preferred embodiments of the present disclosure thus offer advantages over the prior art and are well adapted to carry out one or more of the objects of this disclosure. However, the claimed invention of any particular claim(s) does not require each of the components and acts described above and is in no way limited to the above-described embodiments or methods of operation, except and only to the extent as may be explicitly recited in one or more of the appended claims and only for those claims and any claims depending therefrom. Any one or more of the above components, features and processes may be employed in any suitable configuration without inclusion of other such components, features and processes. Moreover, the present invention includes additional features, capabilities, functions, methods, uses and applications that have not been specifically addressed herein but are, or will become, apparent from the description herein, the appended drawings and claims. All structural and functional equivalents to components of the above-described embodiments and additional embodiments as regarded by those of ordinary skill in the art are hereby expressly incorporated by reference and are intended to be encompassed by the present claims.

The methods that may be described above or claimed herein and any other methods which may fall within the scope of the appended claims can be performed in any desired suitable order and are not necessarily limited to any sequence described herein or as may be listed in the appended claims. Further, the methods of the present invention do not necessarily require use of the particular embodiments shown and described herein, but are equally applicable with any other suitable structure, form and configuration of components.

While exemplary embodiments of the invention have been shown and described, many variations, modifications and/or changes of the system, apparatus and methods of the present invention, such as in the components, details of construction and operation, arrangement of parts and/or methods of use, are possible, contemplated by the patent applicant(s), within the scope of the appended claims, and may be made and used by one of ordinary skill in the art without departing from the spirit or teachings of the invention and scope of appended claims. Thus, all matter herein set forth or shown in the accompanying drawings should be interpreted as illustrative, and the scope of the disclosure and the appended claims should not be limited to the embodiments described and shown herein. Furthermore, no component, method step or detail thereof made or shown in the present disclosure is intended to be dedicated to the public regardless of whether it is explicitly recited in the claims. In addition, the various changes and modifications in form, material and other details of the disclosed embodiments as may be apparent to those of ordinary skill in the art without departing from the spirit and scope of the present disclosure are also encompassed by the present disclosure.

The invention claimed is:

1. A system for use in connection with receiving electroencephalographic (EEG) signals from a human subject's head and taking one or more photoplethysmograms (PPG) of the subject, the subject having at least one ear, each ear having an earlobe with blood vessels passing therethrough and from which the subject's pulse may be detected, the system comprising:
   a removable headset arranged and adapted to extend at least partially around the subject's head over at least part of the subject's scalp, said headset including a plurality of electrode stations and at least one electrical signal transmission wire;
   a plurality of EEG electrodes engageable with said electrode stations of said headset and, during use of said headset, extending between said headset and the subject's scalp and being electrically coupled to at least one said electrical signal transmission wire;
   a plurality of non-conductive electrode biasing flaps, each said electrode biasing flap being releasably engageable with said headset and associated with at least one of said EEG electrodes; and
   at least one ear clip releasably engageable with one of the subject's earlobes and including at least one light transmitter and at least one light receiver positioned on opposite respective sides of the earlobe when said at least one ear clip is engaged with the earlobe.

2. The system of claim 1 wherein at least one of said EEG electrodes is configured to receive electrical signals from the subject's head and at least one said ear clip is configured to take at least one PPG measurement of the subject simultaneously.

3. The system of claim 2 wherein said headset includes at least one electronic processing unit, whereby said at least one said electrical signal transmission wire and said at least one ear clip electrically communicate with at least one said electronic processing unit.

4. The system of claim 2 wherein at least one said ear clip is at least partially electrically conductive and serves as an EEG reference electrode configured to receive one or more electrical signals from the earlobe simultaneously with said at least one ear clip taking at least one PPG measurement of the subject.

5. The system of claim 1 wherein at least one said light transmitter is configured to emit at least one light signal through the earlobe and at least one said light receiver is configured to receive at least one light signal emitted from at least one said light transmitter through the earlobe to take at least one PPG measurement of the subject.

6. The system of claim 5 wherein at least one said ear clip is at least partially electrically conductive and serves as an EEG reference electrode and said headset further includes at least one electronic processing unit, whereby said at least one electrical signal transmission wire and said at least one ear clip electrically communicate with at least one said electronic processing unit.

7. The system of claim 1 wherein at least some of said electrode biasing flaps are configured to bias said at least one associated EEG electrode in the direction of the subject's head independent of said other electrode biasing flaps and their said associated EEG electrodes.

8. A method of receiving electroencephalographic (EEG) signals from a human subject's head and taking one or more photoplethysmograms (PPG) of the subject, the subject having at least one ear, each at least one ear having an earlobe with blood vessels passing therethrough and from which the subject's pulse may be detected, the method comprising:
   placing a removable headset onto the subject's head so that the headset will extend at least partially around the subject's head over at least part of the subject's scalp, the headset including a plurality of EEG electrodes;
   at least one non-conductive electrode biasing flap biasing at least one EEG electrode between the headset and the subject's head;
   at least one EEG electrode facilitating the transmission of one or more electrical EEG signals from the subject's head to at least one electrical signal transmission wire of the headset;
   releasably clamping an ear clip to one of the subject's earlobes; and the ear clip taking one or more photoplethysmograms (PPG) measurements of the subject.

9. The method of claim 8 further including
at least one light transmitter on the ear clip emitting at least one light signal through the earlobe, and
at least one light receiver on the ear clip receiving at least one light signal emitted from the light transmitter through the earlobe.

10. The method of claim 8 further including at least one EEG electrode receiving one or more electrical signals from the subject's head simultaneously with the ear clip taking one or more PPG measurements of the subject.

11. The method of claim 8 further including the ear clip receiving one or more electrical EEG reference signals from the earlobe simultaneously with the ear clip taking one or more PPG measurements of the subject.

12. The method of claim 11 further including
transmitting one or more electrical EEG reference signals and one or more PPG measurements from the ear clip to at least one electronic processing unit of the headset, and
the at least one electronic processing unit transmitting the received at least one EEG reference signals and PPG measurements to at least one computer.

13. The method of claim 8 further including at least one of the electrode biasing flaps biasing at least one EEG electrode associated therewith between the headset and the subject's head independent of any other electrode biasing flaps and EEG electrodes.

14. A system for use in connection with receiving electroencephalographic (EEG) signals from a human subject's head through the scalp thereof, the subject having at least one ear, each at least one ear having an earlobe with blood vessels passing therethrough and from which the subject's pulse may be detected, the system comprising:
a removable headset arranged and adapted to extend at least partially around the subject's head over at least part of the subject's scalp;
a plurality of removable EEG electrodes releasably engageable with said headset and, during use of said headset, extending between said headset and the subject's scalp and being electrically coupled to said headset;
at least one electrode biasing flap constructed at least partially of flexible material and associated with at least one said EEG electrode, wherein electric signals are not transmittable though each said electrode biasing flap; and
at least one ear clip releasably engageable with one of the subject's earlobes, and including an at least partially metallic EEG reference electrode electrically coupled to said headset during use of said at least one ear clip.

15. The system of claim 14 wherein at least one of said ear clips includes first and second earlobe clamping members, at least said first earlobe clamping member having a handle at a first end thereof and a prong at a second end thereof, at least said handle and prong of said first earlobe clamping member being entirely metallic, whereby electrical signals received from the earlobe by said prong of said first earlobe clamping member are transmittable through said handle of said first earlobe clamping member to said headset.

16. The system of claim 15 wherein each said earlobe clamping member is a unitary metallic plate.

17. The system of claim 14 wherein at least one said ear clip further includes at least one light transmitter and at least one light receiver positioned on opposite respective sides of the earlobe when said at least one ear clip is engaged with the earlobe, wherein at least one said light transmitter is configured to emit at least one light signal through the earlobe and at least one said light receiver is configured to receive least one light signal emitted from at least one said light transmitter through the earlobe to take at least one photoplethysmogram of the subject.

18. A method of using the system of claim 14, the method comprising:
placing the headset onto the subject's head so that the headset will extend at least partially around the subject's head over at least part of the subject's scalp; and
at least some of the EEG electrodes facilitating the transmission of EEG signals from the subject's head to the headset.

19. The method of claim 18 further including
releasably engaging at least one ear clip of the headset with one of the subject's earlobes,
at least one light transmitter on the at least one ear clip transmitting at least one light signal through the earlobe, and
at least one light receiver on the ear clip receiving at least one light signal transmitted by the light transmitter through the earlobe to take at least one photoplethysmogram of the subject.

20. A system for use in connection with receiving electroencephalographic (EEG) signals from a human subject's head, the subject having at least one ear, each at least one ear having an earlobe with blood vessels passing therethrough and from which the subject's pulse may be detected, the system comprising:
a removable headset arranged and adapted to extend at least partially around the subject's head over at least part of the subject's scalp, said headset including at least one electrical signal transmission wire;
a plurality of removable EEG electrodes releasably engageable with said headset and, during use of said headset, extending between said headset and the subject's scalp and being electrically coupled to at least one said electrical signal transmission wire;
a plurality of non-conductive electrode biasing flaps, each said electrode biasing flap being separate and distinct from, and releasably engageable with, said headset, wherein each said biasing flap is associated with at least one of said EEG electrodes; and
at least one ear clip electrically coupled to at least one said electrical signal transmission wire of said headset and releasably engaged with one of the subject's earlobes to serve as an EEG reference electrode as desired during use of said at least one ear clip.

21. The system of claim 20 wherein the subject's head includes a lower area extending therearound and at least one eye socket below the lower area, further wherein said headset includes a front end, a rear end and a cap rim configured to at least partially align over and around the lower area of the subject's head, said cap rim including at least one open section proximate to said front of said headset, further including at least one front tautener disposed at said front end of said headset and configured to at least partially draw said cap rim over said at least one open section and tighten said headset to the subject's head.

22. The system of claim 20 further including at least one connection wire having first and second ends, said first end of a first said connection wire being coupled to a first said ear clip and said second end thereof being releasably, magnetically connectable to said headset.

23. The system of claim 20 further including at least one connection wire having first and second ends, said first end of at least a first said connection wire being coupled to a first said ear clip and said second end thereof having at least one magnet having a distinct magnetic polarity, further wherein said headset includes at least one magnet having the opposite magnetic polarity of said at least one magnet of said first connection wire so that said first ear clip is releasably engageable with said headset when said at least one magnet of said first connection wire is placed adjacent to and magnetically engages said at least one magnet of said headset.

24. The system of claim 20 further including a plurality of electrode covers constructed at least partially of flexible, liquid-absorbing material and arranged and adapted to be electrically conductive, receive EEG signals from the subject's head and transmit such signals to at least one said electrical signal transmission wire of said headset during use of said headset, at least one of said electrode covers at least partially encapsulating each said removable EEG electrode, respectively, and being laden with electrically-conductive liquid during use of said headset.

25. The system of claim 20 wherein at least one said ear clip includes at least first and second prongs that releasably engage an earlobe of the subject, at least said first prong being electrically coupled to at least one said electrical signal transmission wire of said headset, said first prong, in its entirety, being electrically conductive to serve as an EEG reference electrode.

26. The system of claim 20 wherein at least one said ear clip includes at least one light transmitter and at least one light receiver positioned on opposite respective sides of one of the subject's earlobes when said at least one ear clip is engaged with the earlobe.

27. The system of claim 26 wherein at least one said light transmitter is configured to emit at least one light signal through the earlobe and at least one said light receiver is configured to receive least one light signal emitted from at least one said light transmitter through the earlobe to take at least one photoplethysmogram of the subject.

28. A method of using the system of claim 20, the method comprising:
placing the headset onto the subject's head so that the headset will extend at least partially around the subject's head over at least part of the subject's scalp;
at least one electrode biasing flap biasing at least one EEG electrode between the headset and the subject's head;
at least some of the EEG electrodes facilitating the transmission of EEG signals from the subject's head to at least one electrical signal transmission wire of the headset;
releasably engaging at least one ear clip with at least one of the subject's earlobes; and
the at least one ear clip receiving at least one electrical EEG reference signal from the earlobe and transmitting it to at least one electrical signal transmission wire of the headset.

29. The method of claim 28 further including
at least one light transmitter on at least one ear clip transmitting at least one light signal through the earlobe, and
at least one light receiver on the at least one ear clip receiving at least one light signal transmitted by the light transmitter through the earlobe to take at least one photoplethysmogram of the subject.

30. The method of claim 28 further including each electrode biasing flap biasing the at least one EEG electrode associated therewith in the direction of the subject's head independent of the other electrode biasing flaps and their associated EEG electrodes.

31. The system of claim 20 wherein said headset includes a front end, a rear end and a plurality of interconnected intermediate web portions extending therebetween, wherein at least two of said intermediate web portions at said front end are not directly interconnected together and form at least one space therebetween, further including at least one front tautener disposed at said front end of said headset and configured to selectively releasably draw said at least two intermediate web portions toward one another at least partially within said at least one space and tighten said headset to the subject's head.

32. The system of claim 20 wherein said headset further includes at least one electronic processing unit, whereby said at least one electrical signal transmission wire and said at least one ear clip are electrically coupled to at least one said electronic processing unit.

33. The system of claim 20 wherein each said electrode biasing flap is configured to bias said at least one associated EEG electrode in the direction of the subject's head independent of said other electrode biasing flaps and their said associated EEG electrodes.

34. A system for use in connection with receiving electroencephalographic (EEG) signals from a human subject's head, the subject having at least one ear, the system comprising:
a removable headset arranged and adapted to extend at least partially around the subject's head over at least part of the subject's scalp;
a plurality of removable EEG electrodes releasably engageable with said headset and, during use of said headset, extending between said headset and the subject's scalp and being electrically coupled to said headset;
a plurality of non-conductive electrode biasing flaps, each said electrode biasing flap being associated with at least one said EEG electrode and directly releasably engaged with said headset separate from said at least one associated EEG electrode; and
at least one ear clip electrically coupled to said headset and releasably engaged with one of the subject's ears to receive electrical signals directed through or received from the earlobe during use of said at least one ear clip.

35. The system of claim 34 wherein each said electrode biasing flap is constructed at least partially of resilient material and releasably coupled to said headset by at least one biasing flap fastener, whereby each said electrode biasing flap may be at least partially disconnected from said headset by disengaging at least one said associated biasing flap fastener.

36. The system of claim 34 wherein at least one said ear clip is at least partially electrically conductive and serves as an EEG reference electrode configured to receive one or more electrical signals from the subject's ear.

37. The system of claim 34 wherein each said ear clip includes at least one light transmitter and at least one light receiver positioned on opposite respective sides of one of the subject's ears when said ear clip is engaged with the ear wherein at least one said light transmitter is configured to emit at least one light signal through the ear and at least one said light receiver is configured to receive least one light signal emitted from at least one said light transmitter through the ear to take at least one photoplethysmogram of the subject.

38. A method of using the system of claim 34, the method comprising:
- placing the headset onto the subject's head so that the headset will extend at least partially around the subject's head over at least part of the subject's scalp;
- at least one electrode biasing flap biasing at least one EEG electrode between the headset and the subject's head; and
- at least some of the EEG electrodes receiving electrical signals from the subject's head.

39. The method of claim 38 further including
- at least one light transmitter on at least one ear clip transmitting at least one light signal through at least one of the subject's ears, and
- at least one light receiver on the at least one ear clip receiving at least one light signal transmitted by the light transmitter through the ear to take at least one photoplethysmogram of the subject.

40. The method of claim 38 further including
- at least some of the electrode biasing flaps biasing at least one EEG electrode associated therewith in the direction of the subject's head independent of the other electrode biasing flaps and EEG electrodes.

* * * * *